US012612451B2

(12) United States Patent
Allen et al.

(10) Patent No.: US 12,612,451 B2
(45) Date of Patent: Apr. 28, 2026

(54) METHOD OF TREATING NEUROMYELITIS OPTICA SPECTRUM DISORDER (NMOSD) COMPRISING ADMINISTERING AN ANTI-C5 ANTIBODY

(71) Applicant: Alexion Pharmaceuticals, Inc., Boston, MA (US)

(72) Inventors: Kerstin Allen, Natick, MA (US); Marcus Yountz, Needham, MA (US); Stephan Ortiz, Wellesley, MA (US); Fanny O'Brien, Norwell, MA (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 905 days.

(21) Appl. No.: 17/783,106

(22) PCT Filed: Dec. 8, 2020

(86) PCT No.: PCT/US2020/063781
§ 371 (c)(1),
(2) Date: Jun. 7, 2022

(87) PCT Pub. No.: WO2021/118999
PCT Pub. Date: Jun. 17, 2021

(65) Prior Publication Data
US 2023/0043034 A1     Feb. 9, 2023

Related U.S. Application Data

(60) Provisional application No. 62/945,644, filed on Dec. 9, 2019.

(51) Int. Cl.
| | |
|---|---|
| *C07K 16/18* | (2006.01) |
| *A61K 31/436* | (2006.01) |
| *A61K 31/519* | (2006.01) |
| *A61K 31/52* | (2006.01) |
| *A61K 31/5377* | (2006.01) |
| *A61K 39/00* | (2006.01) |
| *A61K 39/395* | (2006.01) |
| *A61P 25/00* | (2006.01) |
| *A61P 37/06* | (2006.01) |

(52) U.S. Cl.
CPC ........... *C07K 16/18* (2013.01); *A61K 31/436* (2013.01); *A61K 31/519* (2013.01); *A61K 31/52* (2013.01); *A61K 31/5377* (2013.01); *A61K 39/3955* (2013.01); *A61P 25/00* (2018.01); *A61P 37/06* (2018.01); *A61K 2039/505* (2013.01); *A61K 2039/54* (2013.01); *A61K 2039/545* (2013.01); *A61K 2039/55* (2013.01); *C07K 2317/24* (2013.01); *C07K 2317/565* (2013.01); *C07K 2317/92* (2013.01)

(58) Field of Classification Search
CPC ................ C07K 16/18; C07K 2317/24; C07K 2317/565; C07K 2317/52; C07K 2317/94; C07K 2317/76; C07K 2317/56; A61K 31/436; A61K 31/519; A61K 31/52; A61K 31/5377; A61K 39/3955; A61K 2039/505; A61K 2039/54; A61K 2039/545; A61K 2039/55; A61P 25/00; A61P 37/06

See application file for complete search history.

(56) References Cited

U.S. PATENT DOCUMENTS

| | | | |
|---|---|---|---|
| 5,135,916 | A | 8/1992 | Sims et al. |
| 6,355,245 | B1 | 3/2002 | Evans et al. |
| 8,088,376 | B2 | 1/2012 | Chamberlain et al. |
| 8,241,628 | B2 | 8/2012 | Diefenbach-Streiber et al. |
| 8,883,158 | B2 | 11/2014 | Diefenbach-Streiber et al. |
| 9,079,949 | B1 | 7/2015 | Andrien, Jr. et al. |
| 2009/0220508 | A1 | 9/2009 | Bell et al. |
| 2012/0225056 | A1 | 9/2012 | Rother et al. |
| 2015/0299305 | A1 | 10/2015 | Andrien, Jr. et al. |
| 2017/0355757 | A1 | 12/2017 | Hu et al. |
| 2018/0142010 | A1 | 5/2018 | Bell et al. |
| 2020/0031913 | A1 | 1/2020 | Ruike et al. |
| 2020/0095307 | A1 | 3/2020 | O'Brien |
| 2021/0285964 | A1 | 9/2021 | Mcknight et al. |
| 2023/0416344 | A1 | 12/2023 | Barr et al. |
| 2026/0022164 | A1 | 1/2026 | Allen et al. |

FOREIGN PATENT DOCUMENTS

| | | | |
|---|---|---|---|
| WO | WO-95/29697 | A1 | 11/1995 |
| WO | WO-2011/137362 | A1 | 11/2011 |
| WO | WO-2014/160129 | A2 | 10/2014 |
| WO | WO-2015/134894 | A1 | 9/2015 |
| WO | WO-2017/123636 | A1 | 7/2017 |
| WO | WO-2018/183449 | A1 | 10/2018 |
| WO | WO-2020/061496 | A1 | 3/2020 |
| WO | WO-2022/066774 | A1 | 3/2022 |
| WO | WO-2023/215443 | A1 | 11/2023 |
| WO | WO-2025/221479 | A1 | 10/2025 |

OTHER PUBLICATIONS

Lee JW, et al. (Dec. 3, 2018) Blood. 133(6):530-539. (doi: 10.1182/blood-2018-09-876136).*
U.S. Appl. No. 15/595,890, Bedrosian et al.
U.S. Appl. No. 16/577,703, O'Brien et al.
"A Randomized Controlled Trial of Eculizumab in AQP4 Antibody-positive Participants with NMO (PREVENT Study)," U.S. National Library of Medicine, ClinicalTrials.gov. <https://clinicaltrials.gov/study/NCT01892345?tab=history&a=24>, updated Jun. 26, 2019 (18 pages).
Ortiz et al., "Immediate and sustained terminal complement inhibition with ravulizumab in patients with anti-aquaporin-4 antibody-positive neuromyelitis optica spectrum disorder," Front Neurol. 15:1332890 (Jan. 2024) (9 pages).

(Continued)

*Primary Examiner* — Robert S Landsman
(74) *Attorney, Agent, or Firm* — Clark & Elbing LLP

(57) ABSTRACT

Provided are methods for clinical treatment of neuromyelitis optica spectrum disorder (NMOSD) using an anti-C5 antibody, or antigen binding fragment thereof.

20 Claims, 30 Drawing Sheets

Specification includes a Sequence Listing.

(56)           References Cited

OTHER PUBLICATIONS

Pittock et al., "Eculizumab in Aquaporin-4-Positive Neuromyelitis Optica Spectrum Disorder," N Engl J Med. 381(7):614-625 (Epub May 3, 2019) (Aug. 2019) (12 pages).

Zelek et al., "Compendium of current complement therapeutics," Mol Immunol. 114:341-352 (Oct. 2019).

Pittock et al., "Eculizumab in AQP4-IgG-positive relapsing neuromyelitis optica spectrum disorders: an open-label pilot study," Lancet Neurol. 12(6):554-62 (Jun. 2013) (10 pages).

Ikeda et al., "Inpatient Multidisciplinary Rehabilitation Intervention Outcomes for Neuromyelitis Optica Spectrum Disorder: A Retrospective Observational Study," Prog Rehabil Med. 1:20160007 (Nov. 2016) (7 pages).

Qiu et al., Journal of Clinical Neuroscience Volume 22, Issue 7, Jul. 2015, pp. 1178-1182. Azathioprine plus corticosteroid treatment in Chinese patients with neuromyelitis optica (Year: 2015).

Kelly et al., "Modification of the Eculizumab Dose to Successfully Manage Intravascular Breakthrough Hemolysis in Patients with Paroxysmal Nocturnal Hemoglobinuria," Blood. 112(11 ):1180-1181 (Nov. 2008).

Lathia et al. "Population Pharmacokinetic and Pharmacodynamic Analysis of Eculizumab to Support Phase III Dosing Regimen in Patients with Refractory Generalized Myasthenia Gravis" presented at the American Society for Clinical Pharmacology and Therapeutics annual Meeting, Atlanta, GA, (Mar. 2015) (1 page).

"History of Changes for Study: NCT01997229: Safety and efficacy of Eculizumab in Refractory Generalized Myasthenia Gravis," ClinicalTrials.gov. Earliest record date: Nov. 22, 2013, accessed Jan. 29, 2019 (7 pages).

European Medicines Agency, Scientific Discussion—Soliris, Inn: Eculizumab. 2007 (retrieved on Oct. 2, 2017); pp. 1-41.

Gatault et al., "Therapeutic Drug Monitoring of Eculizumab: Rationale for an Individualized Dosing Schedule." mAbs 7(6):1205-11 (Sep. 2015).

NCT00670774, STEGALL, "Dosing Regimen of Eculizumab Added to Conventional Treatment in Positive Cross Match Living Donor Kidney Transplant." ClinicalTrials.gov last updated Jun. 8, 2015 (retrieved on Oct. 2, 2017); pp. 1-6.

"Eculizumab (Soliris) for Refractory Myasthenia Gravis", NIHR HSRIC ID: 6090, Mar. 2016 (Mar. 2016), pp. 1-7.

European Medicines Agency, Committee for Medicinal Products for Human Use (CHMP); CHMP extension of indication variation assessment report—SOLIRIS, eculizumab; dated Aug. 1, 2017, pp. 1-109.

Howard et al., "A randomized, double-blind, placebo-controlled phase II study of eculizumab in patients with refractory generalized myasthenia gravis," Muscle Nerve 48(1):76-84 (Jul. 2013; Epub Apr. 3, 20130).

Howard et al., "Dual Responder Analyses of Both Muscle Strength and Activities of Daily Living, Eculizumab Versus Placebo, in Refractory Generalized Myasthenia Gravis (gMG) Patients: Results from the REGAIN Study" Abstract, Poster and Presentation from the 69th Annual Meeting of the American Academy of Neurology (AAN), Apr. 22, 2017, pp. 1-5.

Howard et al., "Eculizumab Results in Improvement in Activities of Daily Living and Muscle Strength in Refractory Generalized Myasthenia Gravis Patients Compared with Placebo" Abstract and Presentation from The New York Academy of Sciences (NYAS) 13th International Conference on Myasthenia Gravis and Related Disorders, May 15, 2017, pp. 1-12.

Howard et al., "REGAIN: A Phase 3 Randomized, Double-Blind, Placebo-Controlled, Multi-Center Study to Evaluate the Safety and Efficacy of Eculizumab in Subjects with Refractory Generalized Myasthenia Gravis (gMG)" Abstract and Presentation from the American Associate of Neuromuscular & Electrodiagnostic Medicine (AANEM), Sep. 14, 2016, pp. 1-19.

Howard et al., "REGAIN: A Randomized, Double-Blind, Placebo-Controlled Multi-Center Phase 3 Study of the Safety and Efficacy of Eculizumab in Subjects with Refractory Generalized Myasthenia Gravis" Abstract and Presentation from the International Congress on Neuromuscular Diseases, Jul. 5, 2016, pp. 1-16.

Peng et al., "Role of C5 in the development of airway inflammation, airway hyperresponsiveness, and ongoing airway response," J. Clin. Invest. 115(6):1590-600 (Jun. 2005; Epub May 12, 2005).

Vakeva et al., "Myocardial infarction and apoptosis after myocardial ischemia and reperfusion: role of the terminal complement components and inhibition by anti-C5 therapy," Circulation 97(22): 2259-67 (Jun. 1998).

Vidarsson et al., "IgG subclasses and allotypes: from structure to effector functions," Frontiers in Immunology, vol. 5 Article 520, published Oct. 20, 2014, pp. 1-17.

Wang et al., "A Randomized, Double-Blind, Placebo-Controlled, Phase 3, Multi-Center Study to Evaluate the Safety and Efficacy of Eculizumab in Subjects with Refractory Generalized Myasthenia Gravis: REGAIN" Poster from The Muscle Study Group Society Scientific Meeting, Sep. 19, 2015, one page.

Wang et al., "Complement inhibition with an anti-C5 monoclonal antibody prevents hyperacute rejection in a xenograft heart transplantation model," Transplantation 68(11): 1643-51 (Dec. 1999).

Wurzner et al., "Inhibition of terminal complement complex formation and cell lysis by monoclonal antibodies." Complement. Inflamm. 8(5-6):328-40 (1991).

Fuzakawa, T. et al., Long lasting neutralization of C5 by SKY59, a novel recycling antibody, is a potential therapy for complement-mediated diseases. Sci. Rep., 7:1080, 2017 (Apr. 2017).

Dall'Acqua et al., "Properties of human IgG1s engineered for enhanced binding to the neonatal Fc receptor (FcRn)," J Biol Chem. 281(33):23514-24 (2006).

Hinton et al., "Engineered human IgG antibodies with longer serum half-lives in primates," J Biol Chem. 279(8):6213-6 (2004).

Hinton PR et al., An engineered human IgG1 antibody with longer serum half-life. J Immunol;176(1):346-56. (Jan. 2006).

Petkova et al., "Enhanced half-life of genetically engineered human IgG1 antibodies in a humanized FcRn mouse model: potential application in humorally mediated autoimmune disease," Int Immunol. 18(12):1759-69 (2006).

Datta-Mannan et al., "Monoclonal antibody clearance. Impact of modulating the interaction of IgG with the neonatal Fc receptor," J Biol Chem, vol. 282(3):1709-17 (2007) (10 pages).

Wingerchuk DM et al., Revised diagnostic criteria for neuromyelitis optica. Neurology. 23;66(10):1485-9 (May 2006).

Wingerchuk DM et al., A secondary progressive clinical course is uncommon in neuromyelitis optica. Neurology; 68(8):603-5. Feb. 2007. (9 pages).

Alexion Pharmaceuticals, "An Open Label Extension Trial of Eculizumab in Relapsing NMO Patients—NCT02003144", ClinicalTrials.gov, Dec. 6, 2013 http://clinicaltrials.gov/ct2/show/NCT02003144?term=eculizumab&cond=nmo&draw=2&rank=1.

Alexion Pharmaceuticals, "An Open Label Study of the Effects of Eculizumab in Neuromyelitis Optica—Study Results—NCT00904826", ClinicalTrials.gov, May 20, 2009 https://clinicaltrials.gov/ct2show/results/NCT00904826?term=eculizumab&cond=nmo&draw=2&rank=3.

Whittam et al., "What's new in neuromyelitis optica? A short review for the clinical neurologist", Journal of Neurology, vol. 264, No. 11, Mar. 13, 2017 doi: 10.1007/S00415-017-8445-8.

Frampton et al., "Eculizumab: A Review in Neuromyelitis Optica Spectrum Disorder," Drugs. 80(7):719-727 (Epub Apr. 7, 2020) (May 2020) (9 pages).

Alexion Pharmaceuticals, "An Efficacy and Safety Study of Ravulizumab in Adult Participants with NMOSD—NCT04201262", ClinicalTrials.gov, Dec. 17, 2019. https://clinicaltrials.gov/study/NCT04201262 (10 pages).

Patriquin et al., "Eculizumab and Beyond: The Past, Present, and Future of Complement Therapeutics", Transfusion Medicine Reviews. 33(4):256-265. (Oct. 2019).

Zhu et al., "Human C5-specific single-chain variable fragment ameliorates brain injury in a model of NMOSD", Neurology: Neuroimmunology & Neuroinflammation. 6(3). Apr. 2019. (9 pages).

Zhang et al., "Longitudinal treatment responsiveness on plasma neurofilament light chain and glial fibrillary acidic protein levels in

(56) References Cited

OTHER PUBLICATIONS neuromyelitis optica spectrum disorder," Ther Adv Neurol Disord. 14(1-3):17562864211054952 (Nov. 2021) (13 Pages).

Schindler et al., "Serum GFAP and NfL as disease severity and prognostic biomarkers in patients with aquaporin-4 antibody-positive neuromyelitis optica spectrum disorder," J Neuroinflammation. 18:105 (May 2021) (14 Pages).

Liu et al., "Serum neurofilament light chain and glial fibrillary acidic protein in AQP4-IgG-seropositive neuromyelitis optica spectrum disorders and multiple sclerosis: A cohort study," J Neurochem. 159(5):913-922 (Jul. 2021).

Jasiak-Zatonska et al., "The Immunology of Neuromyelitis Optica-Current Knowledge, Clinical Implications, Controversies and Future Perspectives," Int J Mol Sci. 17:273 (Mar. 2016) (31 Pages).

Aktas et al., "Serum Glial Fibrillary Acidic Protein: A Neuromyelitis Optica Spectrum Disorder Biomarker," Ann Neurol. 89(5):895-910 (Mar. 2021).

Sellner et al., "Targeting interleukin-6 to treat neuromyelitis optica spectrum disorders: Implications from immunology, the FcRn pathway and clinical experience," Drug Discov Today. 26(7):1591-1601 (Mar. 2021).

Mader et al., "Pathomechanisms in demyelination and astrocytopathy: autoantibodies to AQP4, MOG, GFAP, GRP78 and beyond," Curr Opin Neurol. 35(3):427-435 (Jun. 2022).

Melamed et al., "Update on biomarkers in neuromyelitis optica," Neurol Neuroimmunol Neuroinflamm. 2(4):e134 (Jul. 2015) (8 Pages).

* cited by examiner

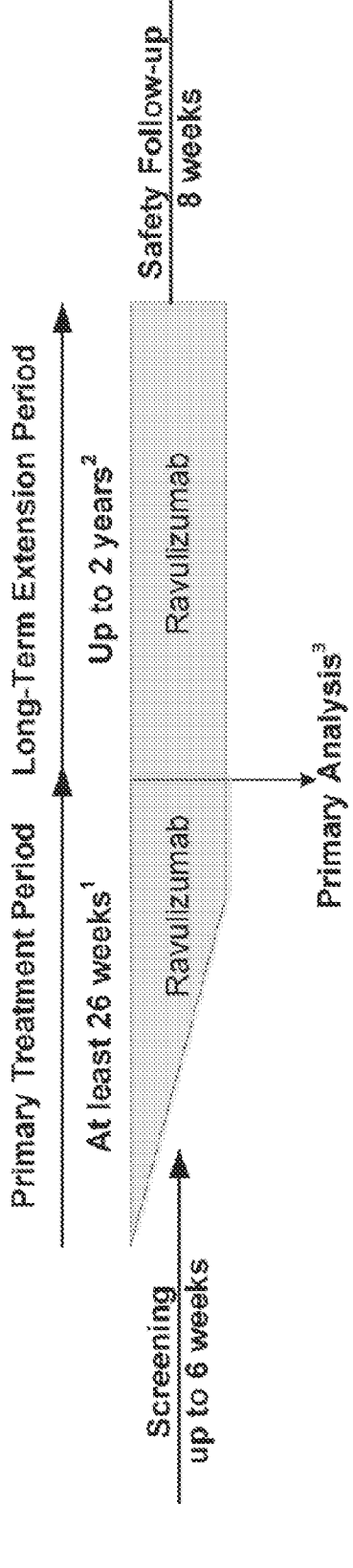

¹All eligible patients will receive open-label ravulizumab during the Primary Treatment Period. The Primary Treatment Period ends when all patients have completed the Week 26 Visit or discontinued early, and then completed their End of Primary Treatment (EOPT) Visit. Based on the estimated enrollment rate, the Primary Treatment Period for each patient will be between 26 weeks and 2 years (inclusive).

²The Long-Term Extension Period starts when all patients complete their EOPT Visit. Patients will continue to receive ravulizumab during the Long-Term Extension Period for up to 2 years, or until ravulizumab is approved and/or available (in accordance with country-specific regulations), whichever occurs first.

³The primary analysis for regulatory submission will be conducted at the end of the Primary Treatment Period, and will include all available efficacy, safety, and PK/PD/ADA data collected from the Primary Treatment Period.

FIGURE 1

| Visit[2] | Screening | Treatment | | | | | | | | | | Notes |
|---|---|---|---|---|---|---|---|---|---|---|---|---|
| Days and Window | W-6 to -1 | D1 | W2<br>D15 ±2 | W6<br>D43 ±2 | W10<br>D71 ±2 | W18<br>D127 ±2 | W26<br>D183 ±2 | W34<br>D239 ±7 | W42<br>D295 ±7 | W50<br>D351 ±7 | W58<br>D407 ±7 | Additional evaluation visits can be scheduled at the discretion of the Investigator. An ED Visit should be performed if patients discontinue early |
| General Assessments/Procedures | | | | | | | | | | | | |
| Informed Consent | X | | | | | | | | | | | |
| Medical History | X | | | | | | | | | | | |
| NMOSD History/Diagnosis | X | | | | | | | | | | | |
| Anti-AQP4 Ab Test (Serum) | X | | | | | | | | | | | Refer to Section 2.1 for testing requirements |
| Inclusion/Exclusion | X | | | | | | | | | | | |
| Demographics | X | | | | | | | | | | | |
| Weight | X | X | X | | X | X | X | X | X | X | X | |
| Height | X | | | | | | | | | | | |
| N. meningitidis Vaccination | X | | | | | | | | | | | Patients must be vaccinated against meningococcal infection, and revaccinated during the study if needed (Section 5.1.4) |
| HIV Test | X | | | | | | | | | | | Test includes HIV-1 and HIV-2 |
| Pregnancy Test (WOCBP only) | X | X | X | | X | X | X | X | X | X | X | Serum test at baseline is required. Urine test at indicated visits and when necessary at Investigator's discretion |
| Dispense Patient Safety Card and NMO Symptom Card | X | | | | | | | | | | | Instruct patients to carry safety card at all times and bring both cards to scheduled visits (Section 5.2.2; Section 5.3.5) |
| Pharmacokinetic and Pharmacodynamic Assessments | | | | | | | | | | | | |
| PK/Free C5 Blood Samples | | B/P | T/P | X | T/P | T/P | T/P | T/P | | T/P | | Collect B (baseline), T (predose), P (postdose) and X (anytime) samples (Section 5.6) |
| PK/Free C5 CSF Samples | | B | | T | | | T | | | | | Optional; collect B (baseline) and T (predose) samples from patients who consent to CSF collection (Section 5.6) |

FIGURE 2

| | Screening | | Treatment | | | | | | | | | Notes |
|---|---|---|---|---|---|---|---|---|---|---|---|---|
| Visit² | W-6 to -1 | D1 | W2 | W6 | W10 | W18 | W26 | W34 | W42 | W50 | W58 | Additional evaluation visits can be scheduled at the discretion of the Investigator. An ED Visit should be performed if patients discontinue early |
| Days and Window | | D1 | D15 ±2 | D43 ±2 | D71 ±2 | D127 ±2 | D183 ±2 | D239 ±7 | D295 ±7 | D35 1±7 | D407 ±7 | |
| ADA Blood Samples | | B | | | | | T | | | T | | Collect B (baseline) and T (predose) samples (Section 5.9) |
| Safety Assessments | | | | | | | | | | | | |
| Physical Examination | X | | | | | | | | | | | |
| Targeted Physical Examination | | X | X | X | X | X | X | X | X | X | X | Perform when deemed necessary by the Investigator (Section 5.3.1) |
| Vital Signs | X | X | X | X | X | X | X | X | X | X | X | |
| ECG | X | X | | | | | X | | | X | | |
| Prior Medications | X | X | | | | | | | | | | |
| Concomitant Medications | | | | | Continuous monitoring | | | | | | | |
| Concomitant Non-Drug Therapies/Procedures | | | | | Continuous monitoring | | | | | | | |
| AE | | | | | Continuous monitoring | | | | | | | |
| Clinical Laboratory Tests | X | X | X | X | X | X | X | X | X | | X | Refer to Section 7.2 for the list of tests |
| Patient Safety Card Review | | X | X | X | X | X | X | X | X | X | X | Review signs and symptoms of infections (Section 5.3.5) |
| C-SSRS | | X | | X | X | X | X | | X | | X | 2 types of C-SSRS assessments: Baseline (Day 1) and Since last visit (Section 5.3.8) |
| Efficacy Assessments | | | | | | | | | | | | |
| Neurologic Examination¹ | X | X | X | X | X | X | X | X | X | | X | |
| NMO Symptom Card and Evaluation | X | X | X | X | X | X | X | X | X | X | X | NMO symptoms will be evaluated by the Investigator (Section 5.2.2) |
| EQ-5D | X | X | | X | | X | X | X | X | | X | When possible, administer before other procedures |
| SF-36 | X | X | | X | | X | X | X | X | | X | When possible, administer before other procedures |
| EDSS (including FSS) | X | X | | X | | X | X | X | X | | X | Conducted by a blinded EDSS Rater Section 5.2.4 |

FIGURE 2 (CONTINUED)

| Visit[2] | Screening | Treatment | | | | | | | | | | Notes |
|---|---|---|---|---|---|---|---|---|---|---|---|---|
| Days and Window | W-6 to -1 | D1 | W2 D15 ±2 | W6 D43 ±2 | W10 D71 ±2 | W18 D127 ±2 | W26 D183 ±2 | W34 D239 ±7 | W42 D295 ±7 | W50 D351 ±7 | W58 D407 ±7 | Additional evaluation visits can be scheduled at the discretion of the Investigator. An ED Visit should be performed if patients discontinue early |
| HAI | X | X | | X | | X | X | | X | | X | Performed by the Investigator or trained designee |
| OSIS[1] | | X | | | | | | | | | | |
| Ophthalmological Exam | X | X | | X | | X | X | | X | | X | Including confrontational field test[1], color vision and visual acuity (Section 5.2.9) |
| OCT | X | X | | X | | | X | | | | | |
| MRI | X | | | | | | | | | | | Brain, cervical spine, and thoracic spine; contrast is optional |
| Biomarker Research | | | | | | | | | | | | |
| Blood samples | X | X | X | X | | | X | | | X | | Blood samples for DNA and RNA are optional; blood sample for DNA is only collected on Day 1. |
| CSF samples | X | X | | X | | | X | | | | | Optional |
| Administration of Study Drug | | | | | | | | | | | | |
| Ravulizumab | | X | X | | X | X | X | X | X | X | X | Administered after all other required tests/procedures |

Abbreviations: ADA = antidrug antibody; AE=adverse event; AQP4 Ab = aquaporin 4 antibody; B = baseline sample; C5= complement component 5; CSF = cerebrospinal fluid; C-SSRS = Columbia-suicide severity rating scale; D = day; DNA = deoxyribonucleic acid; ECG = electrocardiogram; ED = early discontinuation; EDSS = expanded disability status scale; EQ-5D = EuroQoL-5D; FSS = functional system score; HAI = Hauser ambulation index; HIV = human immuno-deficiency virus; MRI = magnetic resonance imaging; NMOSD = neuromyelitis optica spectrum disorder; OCT = ocular coherence tomography;OSIS = optic spinal impairment score; P = postdose sample; PK = pharmacokinetic(s); RNA = ribonucleic acid; SF-36 = short form health survey; T = trough sample; W =week(s); WOCBP = women of childbearing potential

[1]Performed by the Treating Physician who is an investigator and has been properly trained for the evaluation, preferably the same Treating Physician, throughout the study

[2]Under reasonable occasional circumstances where a patient is not able to attend a study visit on site, a home visit may be permitted by the Sponsor after discussing with the Alexion Medical Monitor. This will be a case-by-case decision.

FIGURE 2 (CONTINUED)

| | Treatment | | | | | | | | | | Notes |
|---|---|---|---|---|---|---|---|---|---|---|---|
| Visit[2] | W66 | W74 | W82 | W90 | W98 | W106 | W114 | W122 | W130 | W138 | Additional evaluation visits can be scheduled at the discretion of the Investigator. An ED Visit should be performed if patients discontinue early. |
| Days and Window | D463 ±7 | D519 ±7 | D575 ±7 | D631 ±7 | D687 ±7 | D743 ±7 | D799 ±7 | D855 ±7 | D911 ±7 | D967 ±7 | |
| General Assessments/Procedures | | | | | | | | | | | |
| Weight | X | X | X | X | X | X | X | X | X | X | |
| N. meningitidis Vaccination | | | | | | | | | | | Patients must be vaccinated against meningococcal infection, and revaccinated during the study if needed (Section 5.1.4) |
| Pregnancy Test (WOCBP only) | X | X | X | X | X | X | X | X | X | X | Serum test at baseline is required. Urine test at indicated visits and when necessary at Investigator's discretion |
| Pharmacokinetic and Pharmacodynamic Assessments | | | | | | | | | | | |
| PK/Free C5 Blood Samples | T/P | | T/P | | | T/P | | | T/P | | Collect T (predose), P (postdose) samples (Section 5.6) |
| PK/Free C5 CSF Samples | | T | | | | | | | T | | Optional; collect sample T (predose) from patients who consent to CSF collection (Section 5.6) |
| ADA Blood Samples | | T | | | | T | | | T | | Collect T (predose) samples (Section 5.9) |
| Safety Assessments | | | | | | | | | | | |
| Targeted Physical Examination | X | X | X | X | X | X | X | X | X | X | Perform when deemed necessary by the Investigator (Section 5.3.1) |
| Vital Signs | X | X | X | X | X | X | X | X | X | X | |
| ECG | | | | | | X | | | | | |
| Concomitant Medications | Continuous Monitoring | | | | | | | | | | |
| Concomitant Non-Drug Therapies/Procedures | Continuous Monitoring | | | | | | | | | | |
| AE | Continuous Monitoring | | | | | | | | | | |
| Clinical Laboratory Tests | | X | X | X | X | X | X | X | | X | Refer to Section 4.2 for the list of tests. |
| Patient Safety Card Review | X | X | X | X | X | X | X | X | X | X | Review signs and symptoms of infections (Sections 5.3.5) |
| C-SSRS[1] | X | X | | X | | X | | | X | | Conduct C-SSRS-Since Last Visit assessment (Section 5.3.8) |

FIGURE 2 (CONTINUED)

| | Treatment | | | | | | | | | | Notes |
|---|---|---|---|---|---|---|---|---|---|---|---|
| Visit² | W66 | W74 | W82 | W90 | W98 | W106 | W114 | W122 | W130 | W138 | Additional evaluation visits can be scheduled at the discretion of the Investigator, An ED Visit should be performed if patients discontinue early |
| Days and Window | D463 ±7 | D519 ±7 | D575 ±7 | D631 ±7 | D687 ±7 | D743 ±7 | D799 ±7 | D855 ±7 | D911 ±7 | D967 ±7 | |
| Efficacy Assessments | | | | | | | | | | | |
| Neurologic Examination¹ | | X | | X | | X | | | X | | |
| NMO Symptom Card and Evaluation | X | X | | X | X | X | X | X | X | X | NMO symptoms will be evaluated by the investigator (Section 5.2.2) |
| EQ-5D | | X | | X | | X | | | X | | When possible administer before other procedures |
| SF-36 | | X | | X | | X | | | X | | When possible administer before other procedures |
| EDSS (including FSS) | | X | | X | | X | | X | X | | Conducted by a blinded EDSS Rater (Section 5.2.4) |
| HAI | | X | | X | | X | | | X | | Performed by an Investigator or trained designee |
| Ophthalmological Exam | X | X | | X | | X | | | X | | Including confrontational field test¹, color vision and visual acuity (Landolt C ring)(Section 5.2.9) |
| Biomarker Research | | | | | | | | | | | |
| Blood samples | | | X | | | X | | | X | | Blood samples for RNA are optional |
| CSF samples | | | X | | | | | | | | Optional |
| Administration of Study Drug | | | | | | | | | | | |
| Ravulizumab | X | X | X | X | X | X | X | X | X | X | Administered after all other required tests procedures |

Abbreviations: ADA = antidrug antibody; AE=adverse event; B = baseline sample; C5= complement component 5; CSF = cerebrospinal fluid; C-SSRS = Columbia-suicide severity rating scale; D = day; ECG = electrocardiogram; ED = early discontinuation; EDSS = expanded disability status; EQ-5D = EuroQoL-5D; FSS = functional system score; HAI = Hauser ambulation index; NMO = neuromyelitis optica; P = postdose sample; PK = pharmacokinetic(s); RNA = ribonucleic acid; SF-36 = short form health survey; T = trough sample; W = week(s); WOCBP = women of childbearing potential ¹Performed by the Treating Physician who is an investigator and has been properly trained for the evaluation, preferably the same Treating Physician, throughout the study ²Under reasonable occasional circumstances where a patient is not able to attend a study visit on site, a home visit may be permitted by the Sponsor after discussing with the Alexion Medical Monitor. This will be a case-by-case decision.

FIGURE 2 (CONTINUED)

| Visit³ | W146 | W154 | W162 | W170 | W178 | W186 | W194 | W202 | EOPT | EOT/FD | FU | Notes |
|---|---|---|---|---|---|---|---|---|---|---|---|---|
| Days and Window | D1023 ±7 | D1079 ±7 | D1135 ±7 | D1191 ±7 | D1247 ±7 | D1303 ±7 | D1359 ±7 | D1415 ±7 | within 14 D after PT | | FU | Additional evaluation visits can be scheduled at the discretion of the Investigator. Refer to Section 4.4 for EOPT. An ED Visit should be performed if patient discontinues early |
| General Assessments/Procedures | | | | | | | | | | | | |
| Weight | X | X | X | X | X | X | X | X | X | X | | |
| N. meningitidis Vaccination | | | | | | | | | | | | Patients must be vaccinated against meningococcal infection, and revaccinated during the study if needed (Section 5.1.4) |
| Pregnancy Test (WOCBP only) | X | X | X | X | X | X | X | X | X | X | X | Serum test at baseline is required. Urine test at indicated visits and when necessary at Investigator's discretion |
| Pharmacokinetic and Pharmacodynamic Assessments | | | | | | | | | | | | |
| PK/Free C5 Blood Samples | T/P | T/P | T/P | T/P | T/P | T/P | T/P | | | T/P | | Collect T (predose) and P (postdose) samples (Section 5.6) |
| PK/Free C5 CSF Samples | | | | | | | T | | X | T | | Optional; obtain at predose from patients who consent to CSF sample collection (Section 5.6) |
| ADA Blood Samples | T | T | | T | T | T | T | | X | T | | Collect T (predose) and X (anytime) samples (Section 5.9) |
| Safety Assessments | | | | | | | | | | | | |
| Targeted Physical Examination | X | X | X | X | X | X | X | X | X | X | X | Perform when deemed necessary by the Investigator (Section 5.3.1) |
| Vital Signs | X | X | X | X | X | X | X | X | X | X | X | |
| ECG | | | X | | | | | | | X | | |
| Concomitant Medication | | | | | Continuous Monitoring | | | | | | | |
| Concomitant Non-Drug Therapies/Procedures | | | | | Continuous Monitoring | | | | | | | |
| AE | | | | | Continuous Monitoring | | | | | | | |

FIGURE 2 (CONTINUED)

| Visit[3] | W146 | W154 | W162 | W170 | W178 | W186 | W194 | W202 | EOPT | EOT/FD | FU | Notes |
|---|---|---|---|---|---|---|---|---|---|---|---|---|
| Days and Window | D1023 ±7 | D1079 ±7 | D1135 ±7 | D1191 ±7 | D1247 ±7 | D1303 ±7 | D1359 ±7 | D1415 ±7 | within 14 D after PT | | | Additional evaluation visits can be scheduled at the discretion of the Investigator. Refer to Section 4.4 for EOPT. An ED Visit should be performed if patient discontinues early |
| General Assessments/Procedures | | | | | | | | | | | | |
| Clinical Laboratory Tests | | X | X | X | | X | | X | X | X | X | Refer to Section 7.2 for the list of tests |
| Patient Safety Card | X | X | X | X | X | X | X | X | X | X | X | Review signs and symptoms of infections (Section 5.3.5) |
| C-SSRS[1] | | X | | X | X | | X | X | X | X | X | C-SSRS-Since Last Visit assessment (Section 5.3.8) |
| Efficacy Assessments | | | | | | | | | | | | |
| Neurologic Examination[1] | X | X | | X | X | | | X | X | X | X | |
| NMO Symptom Card and Evaluation | X | X | X | X | X | X | X | X | X | X | X | NMO symptoms will be evaluated by the investigator (Section 5.2.2) |
| EQ-5D | | X | | X | X | | | X | X | X | | When possible, administer before other procedures |
| SF-36 | | X | | X | X | | | X | X | X | | When possible, administer before other procedures |
| EDSS (including FSS) | | X | | X | X | | | X | X | X | | Conducted by a blinded EDSS Rater (Section 5.2.4) |
| HAI | | X | | X | X | | | X | X | X | | Performed by an investigator or Trained designee |
| Ophthalmological Exam | | X | | X | X | | | X | X | X | | Including confrontational field test[1], color vision and visual acuity (Landolt C ring)(Section 5.2.9) |
| Biomarker Research | | | | | | | | | | | | |
| Blood Samples | | | X | | | | X | | $X^2$ | X | | Blood samples for RNA are optional |
| CSF Samples | | | | | | | X | | X | X | | Optional |
| Administration of Study Drug | | | | | | | | | | | | |
| Ravulizumab | X | X | X | X | X | X | X | X | X | X | | Administered after all other required tests/required |

Abbreviations: ADA = antidrug antibody; AE = adverse event; B = baseline sample; C% = complement component 5; CSF = cerebrospinal fluid; C-SSRS= Columbia-suicide severity scale; D = day; ECG = electrocardiogram; ED = Early Discontinuation; EDSS = expanded disability staus scale; EOPT = end of primary treatment;

FIGURE 2 (CONTINUED)

| Visit[3] | Treatment | | | | | | | | | EOT /FD | FU | Notes |
|---|---|---|---|---|---|---|---|---|---|---|---|---|
| | W146 | W154 | W162 | W170 | W178 | W186 | W194 | W202 | EOPT | | FU | Additional evaluation visits can be scheduled at the discretion of the Investigator. Refer to Section 4.4 for EOPT. An ED Visit should be performed if patient discontinues early |
| Days and Window | D1023 ±7 | D1079 ±7 | D1135 ±7 | D119 ±7 | D1247 ±7 | D1303 ±7 | D1359 ±7 | D1415 ±7 | within 14 D after PT | | | |

EOT = end of treatment; EQ-5D = EuroQoL-5D; FSS = functional system score; FU = follow-up; HAI = Hauser ambulation index; NMO = neuromyelitis optic; P = postdose sample; PK = pharmacokinetic(s); PT = primary treatment; RNA = ribonuclic acid; SF-36 = short form health survey; T = trough sample; W = week(s); WOCBP = women of childbearing potential

[1]Performed by the Treating Physician who is the investigator and has been properly trained for the evaluation, preferably the same investigator, throughout the study.
[2]If EOPT visit coincides with a scheduled dosing visit, ravulizumab dose should be administered.
[3]Under reasonable occasional circumstances where a patient is not able to attend a study visit on site, a home visit may be permitted by the Sponsor after discussing with the Alexion Medical Monitor. This will be a case-by-case decision.

FIGURE 2 (CONTINUED)

| Visits | Relapse Evaluation Period | | | | | Notes |
|---|---|---|---|---|---|---|
| | Relapse Evaluation Visit | Relapse FU Visits | | | Unscheduled[1] | |
| Weeks | Within 24 to 48 hours | +1 Week | +4 Weeks | +6 Weeks | Unscheduled[1] | Every effort must be made to evaluate potential relapses within 24 hours of notification of the Investigator of a possible relapse, and no later than 48 hours. |
| Days and Window | RD1 | RD8±2 | RD29±2 | RD43±2 | NA | |
| General Assessments/Procedures | | | | | | |
| Anti-AQP4 Ab (serum) | X | | | X | X | |
| Pharmacokinetic and Pharmacodynamic Assessments | | | | | | |
| PK/Free C5 Blood Samples | X | X | X | X | X | Refer to Section 5.6 for sample collection during relapse |
| Safety Assessments | | | | | | |
| Vital Signs | X | X | X | X | X | |
| Concomitant Medication | | Continuous monitoring | | | | |
| AE | | Continuous monitoring | | | | |
| Clinical laboratory Tests | X | | | X | X | Refer to Sector 7.2 for the list of tests |
| Patient Safety Card | X | X | X | X | X | Review signs and symptoms of infections (Section 5.3.5) |
| C-SSRS | | | | X | | Conduct C-SSRS-Since Last Visit assessment (Section 5.3.8) |
| Efficacy Assessments | | | | | | |
| Neurologic Examination[2] | X | X | X | X | X | NMO symptom will be evaluated by the Treating Physician (Section 5.2.2) |
| NMO Symptom Card and Evaluation | X | X | X | X | X | |
| EQ-5D | X | X | X | X | X | When possible, administer before other procedures |
| SF-36 | X | X | X | X | X | When possible, administer before other procedures |
| EDSS (including FSS) | X | X | X | X | X | Conducted by a blinded EDSS Rater (Section 5.2.4) |
| HAI | X | X | X | X | X | Performed by an investigator or trained designee |
| OSIS[2] | X | X | X | X | X | |
| Ophthalmologic Exam | X | X | X | X | X | Including confrontational field test[2], color vision and visual acuity (Landolt C ring)(Section 5.2.9) |
| MRI | X | | | | | Perform if deemed clinically necessary by the investigator (Section 5.2.10) |

FIGURE 3

| Visits | Relapse Evaluation Period | | | | | Notes |
|---|---|---|---|---|---|---|
| | Relapse Evaluation Visit | Relapse FU Visits | | | | |
| Weeks | Within 24 to 48 hours | +1 Week | +4 Weeks | +6 Weeks | Unscheduled¹ | Every effort must be made to evaluate potential relapses within 24 hours of notification of the Investigator of a possible relapse, and no later than 48 hours. |
| Days and Window | RD1 | RD8±2 | RD29±2 | RD43±2 | NA | |
| OCT | X | | | | | Perform if deemed clinically necessary by the investigator (Section 5.2.10) |
| Biomarker Research | | | | | | |
| Blood Samples | X | X | | X | X | Blood samples for RNA are optional. |
| CSF samples | X | | | | | Optional |
| Administration of Study Drug | | | | | | |
| Ravulizumab | | | | | | Refer to Section 5.1.6 for the instruction of study drug administration during relapse |

Abbreviations: ADA = antidrug antibody; AE = adverse event; C5 = complement component 5; CSF = cerebrospinal fluid; C-SSRS= Columbia-suicide severity scale; EDSS = expanded disability status scale; EQ-5D = EuroQoL-5D; FSS = functional system score; FU = follow-up; HAI = Hauser ambulation index; MRI = magnetic resonance imaging; NA = not applicable; NMO = neuromyelitis optic; OCT = ocular coherence tomography; OSIS= optic spinal imparement score; PK = pharmacokinetic(s); RD= relapse day; RNA = ribonucleic acid; SF-36 = short form health survey; T = trough sample; W = week(s); WOCBP = women of childbearing potential ¹Additional unscheduled Follow-up Relapse Evaluation Visits are permitted at the discretion of the Investigator.
² Performed by the Treating Physician who is the investigator and has been properly trained for the evaluation, preferably the same investigator, throughout the study.

FIGURE 3 (CONTINUED)

| Kurtzke Expanded Disability Status Scale | |
| --- | --- |
| 0.0 | Normal neurological examination |
| 1.0 | No disability, minimal signs in one FS |
| 1.5 | No disability, minimal signs in more than one FS |
| 2.0 | Minimal disability in one FS |
| 2.5 | Mild disability in one FS or minimal disability in 2 FS |
| 3.0 | Moderate disability in one FS, or mild disability in 3 or 4 FS. Fully ambulatory |
| 3.5 | Fully ambulatory but with moderate disability in one FS and more than minimal disability in several others |
| 4.0 | Fully ambulatory without aid, self-sufficient, up and about some 12 hours a day despite relatively severe disability; able to walk without aid or rest some 500 meters |
| 4.5 | Fully ambulatory without aid, up and about much of the day, able to work a full day, may otherwise have some limitation of full activity or require minimal assistance; characterized by relatively severe disability; able to walk without aid or rest some 300 meters |
| 5.0 | Ambulatory without aid or rest for about 200 meters; disability severe enough to impair full daily activities (work a full day without special provisions) |
| 5.5 | Ambulatory without aid or rest for about 100 meters; disability severe enough to preclude full daily activities |
| 6.0 | Intermittent or unilateral constant assistance (cane, crutch, brace) required to walk about 100 meters with or without resting |
| 6.5 | Constant bilateral assistance (canes, crutches, braces) required to walk about 20 meters without resting |
| 7.0 | Unable to walk beyond approximately 5 meters even with aid, essentially restricted to wheelchair; wheels self in standard wheelchair and transfers alone; up and about in wheelchair some 12 hours a day |

FIGURE 4

| 7.5 | Unable to take more than a few steps; restricted to wheelchair; may need aid in transfer; wheels self but cannot carry on in standard wheelchair a full day; May require motorized wheelchair |
|---|---|
| 8.0 | Essentially restricted to bed or chair or perambulated in wheelchair, but may be out of bed itself much of the day; retains many self-care functions; generally has effective use of arms |
| 8.5 | Essentially restricted to bed much of day; has some effective use of arms retains some self-care functions |
| 9.0 | Confined to bed; can still communicate and eat |
| 9.5 | Totally helpless bed patient; unable to communicate effectively or eat/swallow |
| 10.0 | Death due to MS |

FIGURE 4 (Continued)

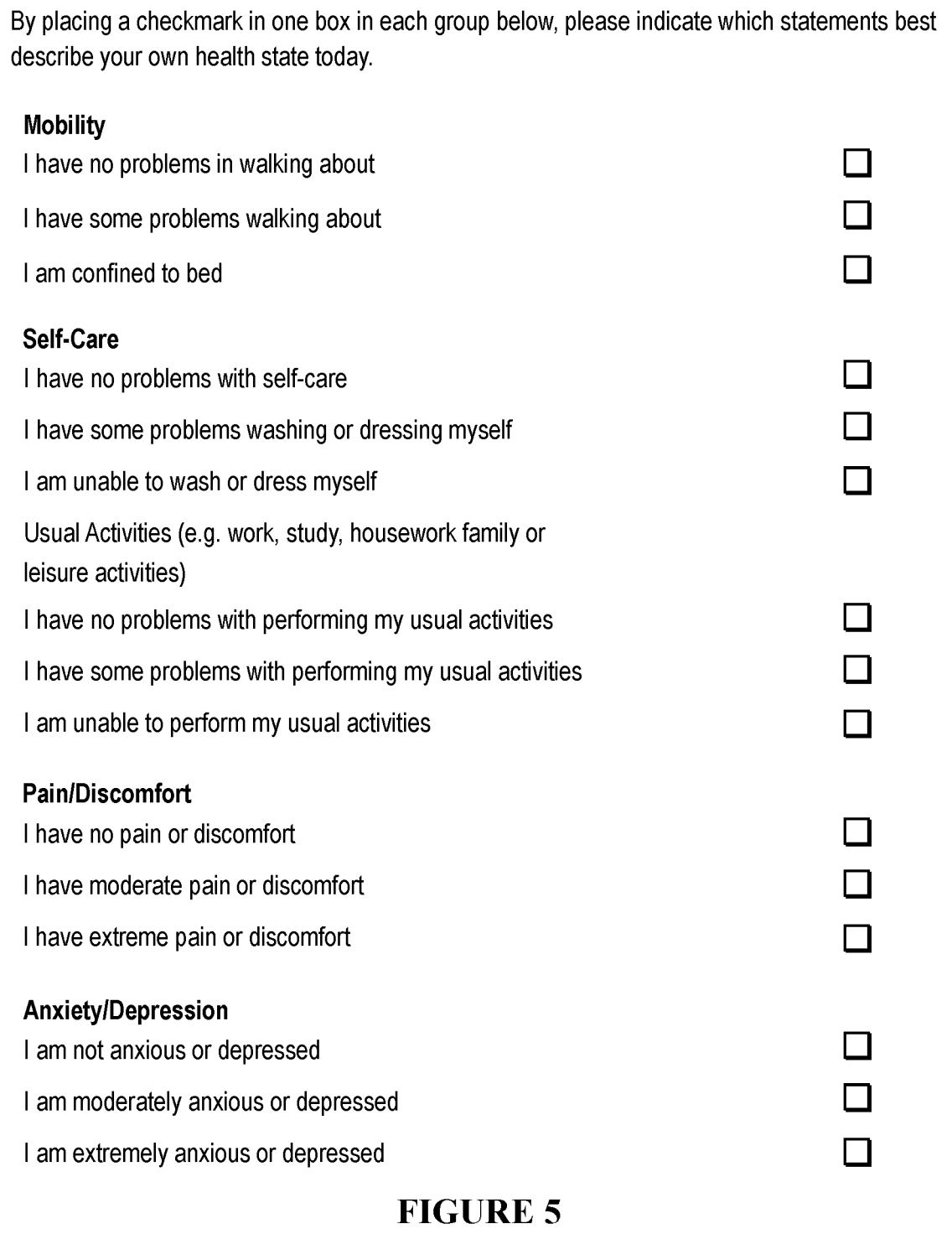

By placing a checkmark in one box in each group below, please indicate which statements best describe your own health state today.

Mobility

I have no problems in walking about     ☐

I have some problems walking about     ☐

I am confined to bed     ☐

Self-Care

I have no problems with self-care     ☐

I have some problems washing or dressing myself     ☐

I am unable to wash or dress myself     ☐

Usual Activities (e.g. work, study, housework family or leisure activities)

I have no problems with performing my usual activities     ☐

I have some problems with performing my usual activities     ☐

I am unable to perform my usual activities     ☐

Pain/Discomfort

I have no pain or discomfort     ☐

I have moderate pain or discomfort     ☐

I have extreme pain or discomfort     ☐

Anxiety/Depression

I am not anxious or depressed     ☐

I am moderately anxious or depressed     ☐

I am extremely anxious or depressed     ☐

FIGURE 5

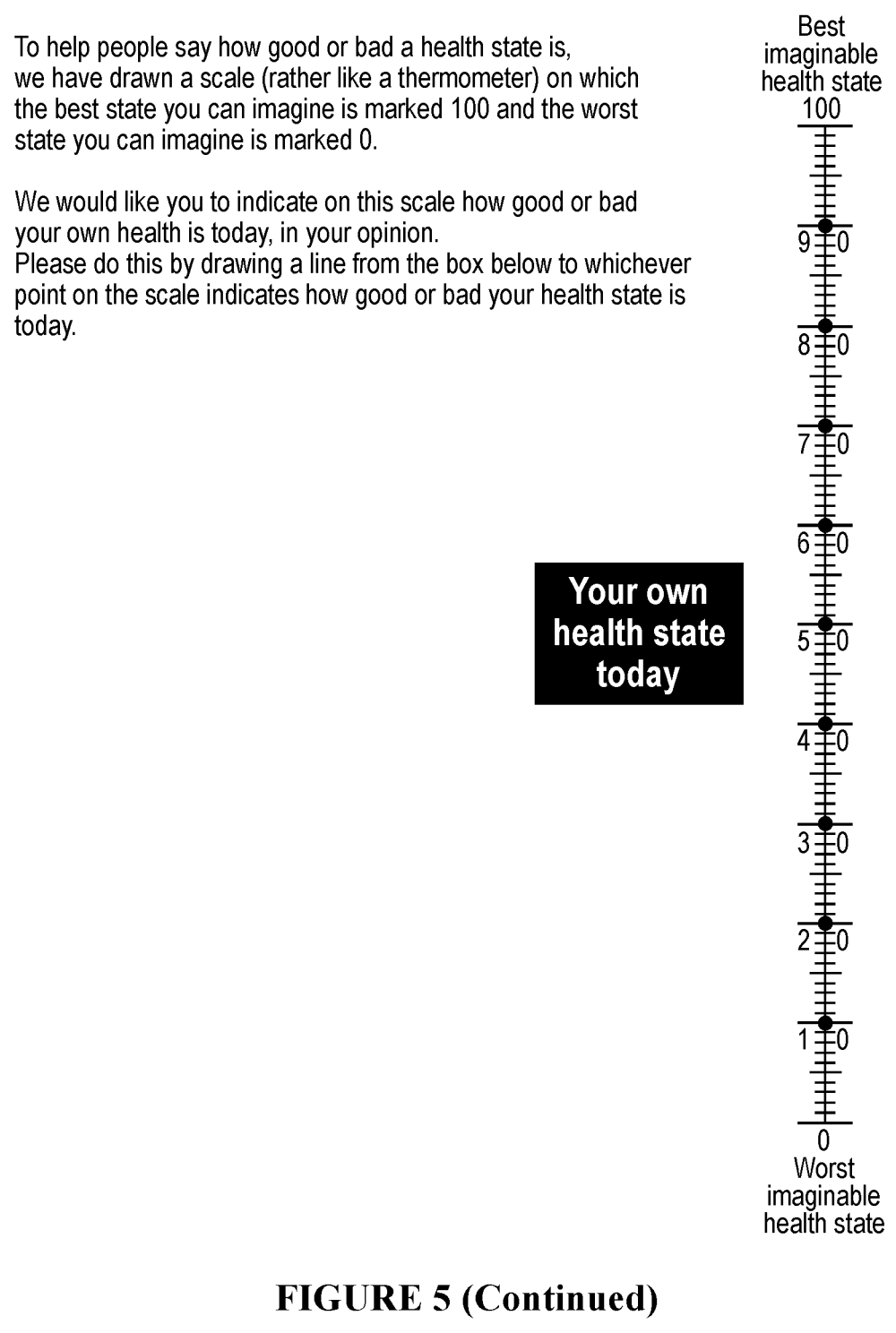

To help people say how good or bad a health state is,
we have drawn a scale (rather like a thermometer) on which
the best state you can imagine is marked 100 and the worst
state you can imagine is marked 0.

We would like you to indicate on this scale how good or bad
your own health is today, in your opinion.
Please do this by drawing a line from the box below to whichever
point on the scale indicates how good or bad your health state is
today.

**Your own
health state
today**

Best
imaginable
health state
100

90

80

70

60

50

40

30

20

10

0
Worst
imaginable
health state

FIGURE 5 (Continued)

Your Health and Well-Being

This survey asks for your views about your health. This information will help keep track of how you feel and how well you are able to do your usual activities. *Thank you for completing this survey!*

For each of the following questions, please mark an ⊠ in the one box that best describes your answer.

1. In general, would you say your health is:

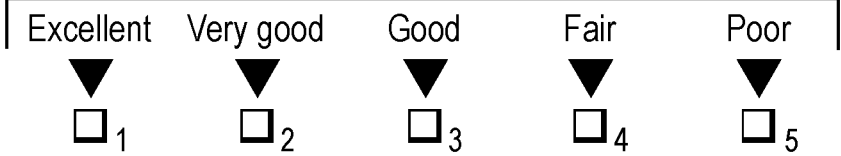

| Excellent | Very good | Good | Fair | Poor |
|:---:|:---:|:---:|:---:|:---:|
| ▼ | ▼ | ▼ | ▼ | ▼ |
| □ 1 | □ 2 | □ 3 | □ 4 | □ 5 |

2. <u>Compared to one year ago</u>, how would you rate your health in general <u>now</u>?

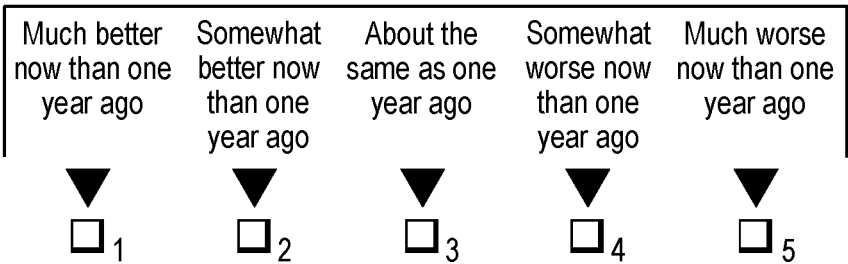

| Much better now than one year ago | Somewhat better now than one year ago | About the same as one year ago | Somewhat worse now than one year ago | Much worse now than one year ago |
|:---:|:---:|:---:|:---:|:---:|
| ▼ | ▼ | ▼ | ▼ | ▼ |
| □ 1 | □ 2 | □ 3 | □ 4 | □ 5 |

FIGURE 6

3. The following questions are about activities you might do during a typical day. Does <u>your health now limit you</u> in these activities? If so, how much?

| | Yes, limited a lot ▼ | Yes, limited a little ▼ | No, not limited at all ▼ |
|---|---|---|---|
| a <u>Vigorous activities</u>, such as running, lifting heavy objects, participating in strenuous sports | ☐1 | ☐2 | ☐3 |
| b <u>Moderate activities</u>, such as moving a table, pushing a vacuum cleaner, bowling, or playing golf | ☐1 | ☐2 | ☐3 |
| c Lifting or carrying groceries | ☐1 | ☐2 | ☐3 |
| d Climbing <u>several</u> flights of stairs | ☐1 | ☐2 | ☐3 |
| e Climbing <u>one</u> flight of stairs | ☐1 | ☐2 | ☐3 |
| f Bending, kneeling, or stooping | ☐1 | ☐2 | ☐3 |
| g Walking <u>more than a mile</u> | ☐1 | ☐2 | ☐3 |
| h Walking <u>several hundred yards</u> | ☐1 | ☐2 | ☐3 |
| i Walking <u>one hundred yards</u> | ☐1 | ☐2 | ☐3 |
| j Bathing or dressing yourself | ☐1 | ☐2 | ☐3 |

FIGURE 6 (Continued)

4. During the <u>past 4 weeks</u>, how much of the time have you had any of the following problems with your work or other regular daily activities <u>as a result of your physical health</u>?

|  | All of the time ▼ | Most of the time ▼ | Some of the time ▼ | A little of the time ▼ | None of the time ▼ |
|---|---|---|---|---|---|
| a Cut down on the <u>amount of time</u> you spent on work or other activities............ | ☐1 | ☐2 | ☐3 | ☐4 | ☐5 |
| b <u>Accomplished less</u> than you would like.................................................. | ☐1 | ☐2 | ☐3 | ☐4 | ☐5 |
| c Were limited in the <u>kind</u> of work or other activities..................................... | ☐1 | ☐2 | ☐3 | ☐4 | ☐5 |
| d Had <u>difficulty</u> performing the work or other activities (for example, it took extra effort)........................................ | ☐1 | ☐2 | ☐3 | ☐4 | ☐5 |

5. During the <u>past 4 weeks</u>, how much of the time have you had any of the following problems with your work or other regular daily activities <u>as a result of any emotional problems</u> (such as feeling depressed or anxious?

|  | All of the time ▼ | Most of the time ▼ | Some of the time ▼ | A little of the time ▼ | None of the time ▼ |
|---|---|---|---|---|---|
| a Cut down on the <u>amount of time</u> you spent on work or other activities............ | ☐1 | ☐2 | ☐3 | ☐4 | ☐5 |
| b <u>Accomplished less</u> than you would like.................................................. | ☐1 | ☐2 | ☐3 | ☐4 | ☐5 |
| c Did work or other activities <u>less carefully than usual</u>.............................. | ☐1 | ☐2 | ☐3 | ☐4 | ☐5 |

FIGURE 6 (Continued)

6.  During the <u>past 4 weeks</u>, to what exrent has your <u>physical health or emotional problems</u> interfered with you normal social activities with family, friends, neighbors, or groups?

| Not at all | Slightly | Moderately | Quite a bit | Extremely |
|:---:|:---:|:---:|:---:|:---:|
| ▼ | ▼ | ▼ | ▼ | ▼ |
| ☐ 1 | ☐ 2 | ☐ 3 | ☐ 4 | ☐ 5 |

7.  How much <u>bodily</u> pain have you had during the <u>past 4 weeks</u>?

| None | Very mild | Mild | Moderate | Severe | Very Severe |
|:---:|:---:|:---:|:---:|:---:|:---:|
| ▼ | ▼ | ▼ | ▼ | ▼ | ▼ |
| ☐ 1 | ☐ 2 | ☐ 3 | ☐ 4 | ☐ 5 | ☐ 6 |

8.  During the <u>past 4 weeks</u>, how much did <u>pain</u> interfere with your normal work (including both work outside the home and housework?

| Not at all | Slightly | Moderately | Quite a bit | Extremely |
|:---:|:---:|:---:|:---:|:---:|
| ▼ | ▼ | ▼ | ▼ | ▼ |
| ☐ 1 | ☐ 2 | ☐ 3 | ☐ 4 | ☐ 5 |

FIGURE 6 (Continued)

9. These questions are about how you feel and how things have been with you during the past 4 weeks. For each question, please give the one answer that comes closest to the way you have been feeling. How much of the time during the past 4 weeks. . .

| | All of the time ▼ | Most of the time ▼ | Some of the time ▼ | A little of the time ▼ | None of the time ▼ |
|---|---|---|---|---|---|
| a Did you feel full of life? | $\square_1$ | $\square_2$ | $\square_3$ | $\square_4$ | $\square_5$ |
| b Have you been very nervous? | $\square_1$ | $\square_2$ | $\square_3$ | $\square_4$ | $\square_5$ |
| c Have you felt so down in the dumps that nothing could cheer you up? | $\square_1$ | $\square_2$ | $\square_3$ | $\square_4$ | $\square_5$ |
| d Have you felt calm and peaceful? | $\square_1$ | $\square_2$ | $\square_3$ | $\square_4$ | $\square_5$ |
| e Did you have a lot of energy? | $\square_1$ | $\square_2$ | $\square_3$ | $\square_4$ | $\square_5$ |
| f Have you felt downhearted and depressed? | $\square_1$ | $\square_2$ | $\square_3$ | $\square_4$ | $\square_5$ |
| g Did you feel worn out? | $\square_1$ | $\square_2$ | $\square_3$ | $\square_4$ | $\square_5$ |
| h Have you been happy? | $\square_1$ | $\square_2$ | $\square_3$ | $\square_4$ | $\square_5$ |
| i Did you feel tired? | $\square_1$ | $\square_2$ | $\square_3$ | $\square_4$ | $\square_5$ |

10. During the past 4 weeks, how much of the time has your physical health or emotional problems interfered with your social activities (like visiting friends, relatives, etc.)?

| All of the time ▼ | Most of the time ▼ | Some of the time ▼ | A little of the time ▼ | None of the time ▼ |
|---|---|---|---|---|
| $\square_1$ | $\square_2$ | $\square_3$ | $\square_4$ | $\square_5$ |

FIGURE 6 (Continued)

11. How TRUE or False is <u>each</u> of the following statements for you?

|  | Definitely<br>true | Mostly<br>true | Don't<br>know | Mostly<br>false | Definitely<br>false |
|---|---|---|---|---|---|
| a I seem to get sick a little easier<br>  than other people................................ | $\square_1$ | $\square_2$ | $\square_3$ | $\square_4$ | $\square_5$ |
| b I am as healthy as anybody I know...... | $\square_1$ | $\square_2$ | $\square_3$ | $\square_4$ | $\square_5$ |
| c I expect my health to get worse........... | $\square_1$ | $\square_2$ | $\square_3$ | $\square_4$ | $\square_5$ |
| d My health is excellent.......................... | $\square_1$ | $\square_2$ | $\square_3$ | $\square_4$ | $\square_5$ |

*THANK YOU FOR COMPLETING THESE QUESTIONS!*

FIGURE 6 (Continued)

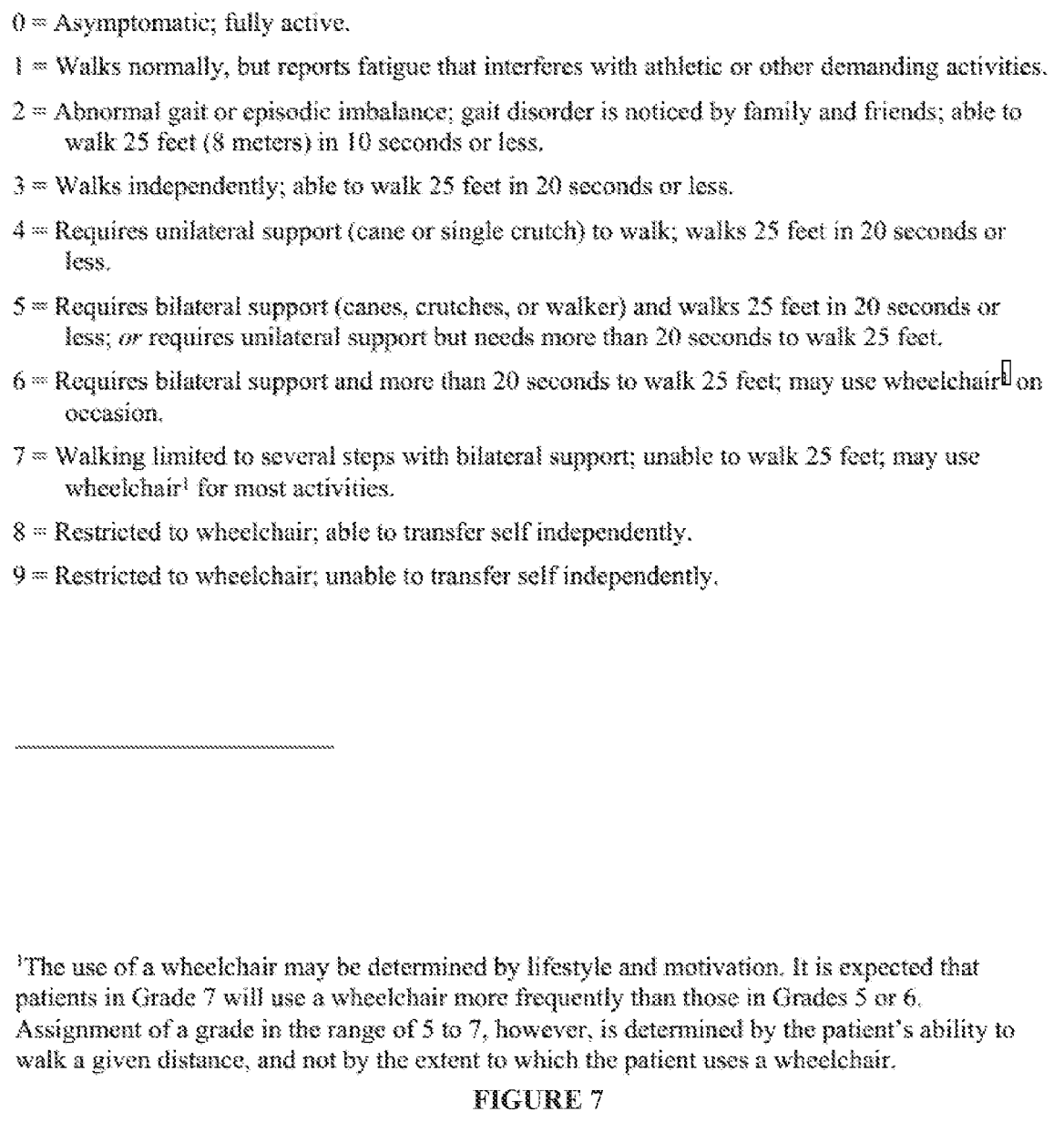

0 = Asymptomatic; fully active.

1 = Walks normally, but reports fatigue that interferes with athletic or other demanding activities.

2 = Abnormal gait or episodic imbalance; gait disorder is noticed by family and friends; able to walk 25 feet (8 meters) in 10 seconds or less.

3 = Walks independently; able to walk 25 feet in 20 seconds or less.

4 = Requires unilateral support (cane or single crutch) to walk; walks 25 feet in 20 seconds or less.

5 = Requires bilateral support (canes, crutches, or walker) and walks 25 feet in 20 seconds or less; or requires unilateral support but needs more than 20 seconds to walk 25 feet.

6 = Requires bilateral support and more than 20 seconds to walk 25 feet; may use wheelchair[1] on occasion.

7 = Walking limited to several steps with bilateral support; unable to walk 25 feet; may use wheelchair[1] for most activities.

8 = Restricted to wheelchair; able to transfer self independently.

9 = Restricted to wheelchair; unable to transfer self independently.

––––––––––––––––––––––––––––––––––––––––––

[1]The use of a wheelchair may be determined by lifestyle and motivation. It is expected that patients in Grade 7 will use a wheelchair more frequently than those in Grades 5 or 6. Assignment of a grade in the range of 5 to 7, however, is determined by the patient's ability to walk a given distance, and not by the extent to which the patient uses a wheelchair.

FIGURE 7

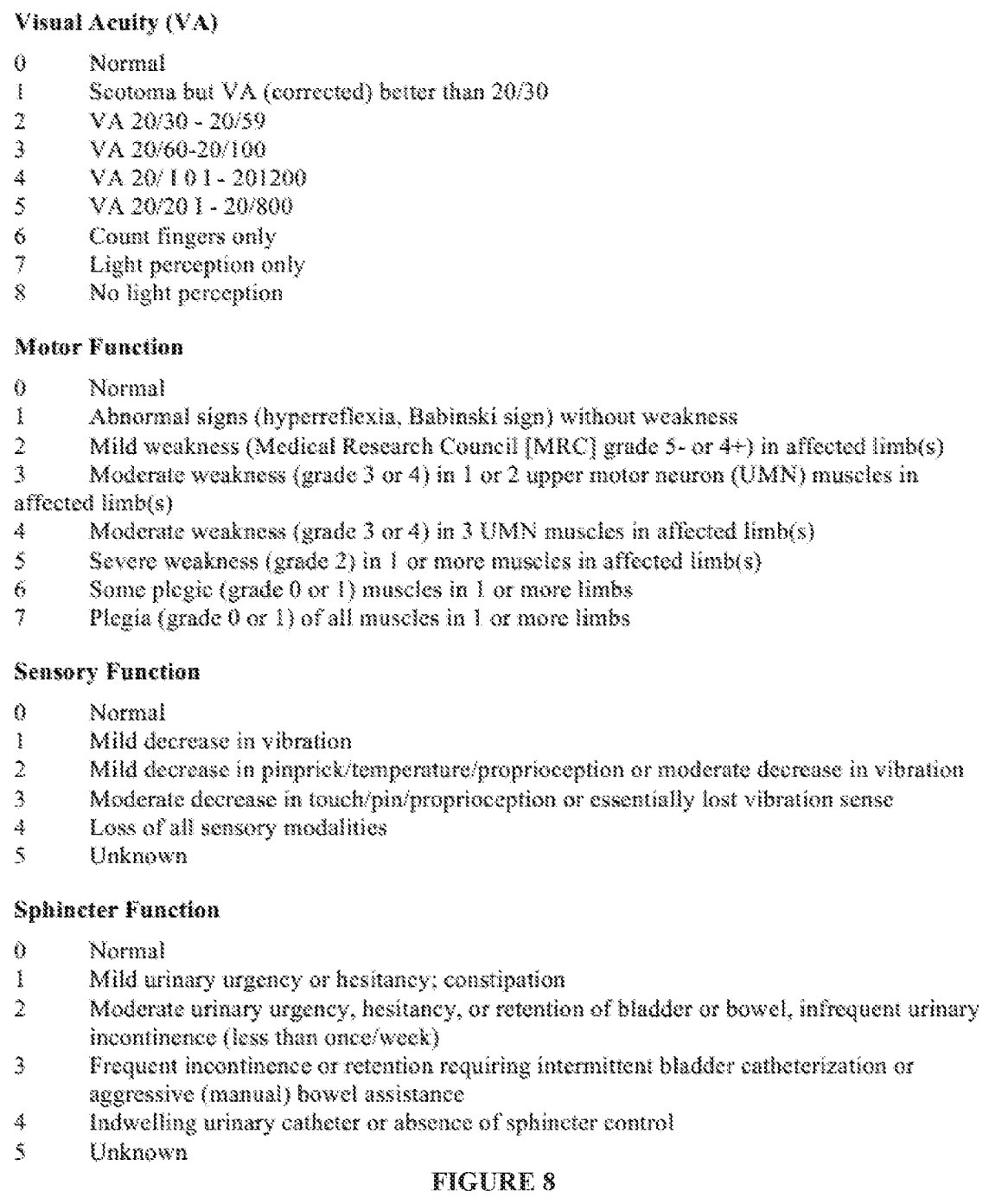

Visual Acuity (VA)

0    Normal
1    Scotoma but VA (corrected) better than 20/30
2    VA 20/30 - 20/59
3    VA 20/60-20/100
4    VA 20/101 - 20l200
5    VA 20/201 - 20/800
6    Count fingers only
7    Light perception only
8    No light perception

Motor Function

0    Normal
1    Abnormal signs (hyperreflexia, Babinski sign) without weakness
2    Mild weakness (Medical Research Council [MRC] grade 5- or 4+) in affected limb(s)
3    Moderate weakness (grade 3 or 4) in 1 or 2 upper motor neuron (UMN) muscles in affected limb(s)
4    Moderate weakness (grade 3 or 4) in 3 UMN muscles in affected limb(s)
5    Severe weakness (grade 2) in 1 or more muscles in affected limb(s)
6    Some plegic (grade 0 or 1) muscles in 1 or more limbs
7    Plegia (grade 0 or 1) of all muscles in 1 or more limbs

Sensory Function

0    Normal
1    Mild decrease in vibration
2    Mild decrease in pinprick/temperature/proprioception or moderate decrease in vibration
3    Moderate decrease in touch/pin/proprioception or essentially lost vibration sense
4    Loss of all sensory modalities
5    Unknown

Sphincter Function

0    Normal
1    Mild urinary urgency or hesitancy; constipation
2    Moderate urinary urgency, hesitancy, or retention of bladder or bowel, infrequent urinary incontinence (less than once/week)
3    Frequent incontinence or retention requiring intermittent bladder catheterization or aggressive (manual) bowel assistance
4    Indwelling urinary catheter or absence of sphincter control
5    Unknown

FIGURE 8

| Optic Neuritis | | |
|---|---|---|
| Visual Acuity Subscale Score (taken from the eye with the largest change at the time of the event) | | Relapse Descriptor |
| Pre-Relapse | Post-Relapse | |
| 0-1 | 0-2 | Minor |
| 0-1 | 3+ | Major |
| 2-7 | Increase by 1 point | Minor |
| 2-7 | Increase by ≥ 2 points | Major |
| Transverse Myelitis | | |
| Motor Subscale Score | | Relapse Descriptor |
| Pre-Relapse | Post-Relapse | |
| 0-1 | 0-2 | Minor |
| 0-1 | 3+ | Major |
| 2-6 | Increase by 1 point | Minor |
| 2-6 | Increase by ≥ 2 points | Major |
| Sensory Subscale Score | | Relapse Descriptor |
| Based on proprioceptive loss only | If severe loss in ≥ 1 or more limbs with prior normal function or with mild proprioceptive loss | Major |

FIGURE 9

SUICIDAL IDEATION

| | Lifetime: Time He/She Felt Most Suicidal | Past ___ Months |
|---|---|---|
| *Ask questions 1 and 2. If both are negative, proceed to "Suicidal Behavior" section. If the answer to question 2 is "yes", ask questions 3, 4 and 5. If the answer to question 1 and/or 2 is "yes", complete "Intensity of Ideation" section below.* | | |
| 1. Wish to be Dead<br>Subject endorses thoughts about a wish to be dead or not alive anymore, or wish to fall asleep and not wake up.<br>*Have you wished you were dead or wished you could go sleep and not wake up?*<br><br>If yes, describe: | Yes ☐  No ☐ | Yes ☐  No ☐ |
| 2. Non-Specific Active Suicidal Thoughts<br>General, non-specific thoughts of wanting to end one's life/commit suicidal (e.g., "I've thought about killing myself") without thoughts of ways to kill oneself/associated methods, intent, or plan during the assessment period.<br>*Have you actually had any thoughts of killing yourself?*<br><br>If yes, describe: | Yes ☐  No ☐ | Yes ☐  No ☐ |
| 3. Active Suicidal Ideation with Any Methods (Not Plan) without Intent to Act<br>Subject endorses thoughts of suicide and has thought of at least one method during the assessment period. This is different than a specific plan with time, place or method details worked out (e.g., thought of method to kill self but not a specific plan). Includes person who would say, "I thought about taking an overdose but I never made a specific plan as to when, where or how I would actually do it...and I would never go through with it."<br>*Have you been thinking about how you might do this?*<br><br>If yes, describe: | Yes ☐  No ☐ | Yes ☐  No ☐ |
| 4. Active Suicidal Ideation with Some Intent to Act, without Specific Plan<br>Active suicidal thoughts of killing oneself and subject reports having some intent to act on such thoughts, as opposed to "I have the thoughts but I definitely will not do anything about them."<br>*Have you had these thoughts and had some intention of acting on them?*<br><br>If yes, describe: | Yes ☐  No ☐ | Yes ☐  No ☐ |
| 5. Active Suicidal Ideation with Specific Plan and Intent<br>Thoughts of killing oneself with details of plan fully or partially worked out and subject has some intent to carry it out.<br>*Have you started to work out or worked out the details of how to kill yourself? Do you intend to carry out this plan?*<br><br>If yes, describe: | Yes ☐  No ☐ | Yes ☐  No ☐ |

FIGURE 10

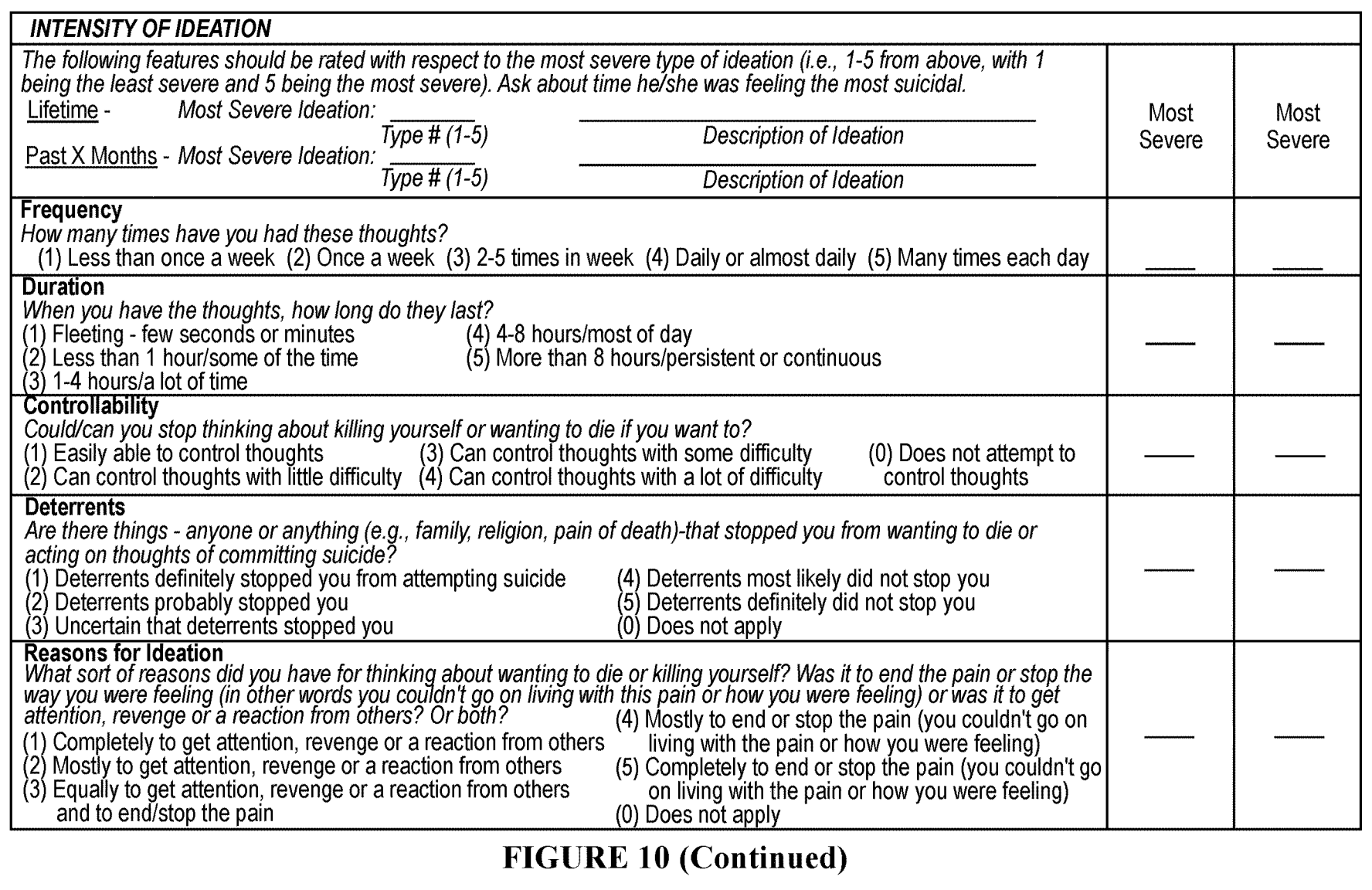

| | Most Severe | Most Severe |
|---|---|---|

INTENSITY OF IDEATION

The following features should be rated with respect to the most severe type of ideation (i.e., 1-5 from above, with 1 being the least severe and 5 being the most severe). Ask about time he/she was feeling the most suicidal.

Lifetime -      Most Severe Ideation:
_____
Type # (1-5)      Description of Ideation Past X Months - Most Severe Ideation:
_____
Type # (1-5)      Description of Ideation

Frequency
How many times have you had these thoughts?
(1) Less than once a week  (2) Once a week  (3) 2-5 times in week  (4) Daily or almost daily  (5) Many times each day      |  —  |  —  |

Duration
When you have the thoughts, how long do they last?
(1) Fleeting - few seconds or minutes          (4) 4-8 hours/most of day
(2) Less than 1 hour/some of the time          (5) More than 8 hours/persistent or continuous
(3) 1-4 hours/a lot of time      |  —  |  —  |

Controllability
Could/can you stop thinking about killing yourself or wanting to die if you want to?
(1) Easily able to control thoughts        (3) Can control thoughts with some difficulty        (0) Does not attempt to
(2) Can control thoughts with little difficulty  (4) Can control thoughts with a lot of difficulty          control thoughts      |  —  |  —  |

Deterrents
Are there things - anyone or anything (e.g., family, religion, pain of death)-that stopped you from wanting to die or acting on thoughts of committing suicide?
(1) Deterrents definitely stopped you from attempting suicide    (4) Deterrents most likely did not stop you
(2) Deterrents probably stopped you                              (5) Deterrents definitely did not stop you
(3) Uncertain that deterrents stopped you                        (0) Does not apply      |  —  |  —  |

Reasons for Ideation
What sort of reasons did you have for thinking about wanting to die or killing yourself? Was it to end the pain or stop the way you were feeling (in other words you couldn't go on living with this pain or how you were feeling) or was it to get attention, revenge or a reaction from others? Or both?
(1) Completely to get attention, revenge or a reaction from others    (4) Mostly to end or stop the pain (you couldn't go on
(2) Mostly to get attention, revenge or a reaction from others           living with the pain or how you were feeling)
(3) Equally to get attention, revenge or a reaction from others      (5) Completely to end or stop the pain (you couldn't go
   and to end/stop the pain                                              on living with the pain or how you were feeling)
                                                                     (0) Does not apply      |  —  |  —  |

FIGURE 10 (Continued)

| | Since Last Visit |
|---|---|
| *SUICIDAL BEHAVIOR*<br>*(Check all that apply, so long as these are separate events; must ask about all types* | |
| Actual Attempt:<br>A potentially self-injurious act committed with at least some wish to die, *as a result of act*. Behavior was in part thought of as method to kill oneself. Intent does not have to be 100%. If there is *any* intent/desire to die associated with the act, then it can be considered an actual suicide attempt. *There does not have to be any injury or harm*, just the potential for injury or harm. If person pulls trigger while gun is in mouth but gun is broken so no injury results, this is considered an attempt.<br>Inferring Intent: Even if an individual denies intent/wish to die, it may be inferred clinically from the behavior or circumstances. For example a highly lethal act that is clearly not an accident so no other intent but suicide can be inferred (e.g., gunshot to head, jumping from the window of a high floor/story). Also, if someone denies intent to die, but they thought what they did could be lethal, intent may be inferred.<br>*Have you made a suicide attempt?*<br>*Have you done anything to harm yourself?*<br>*Have you done anything dangerous where you could have died?*<br>　　*What did you do?*<br>　　*Did you _____ as a way to end your life?*<br>　　*Did you want to die (even a little) when you _____?*<br>　　*Were you trying to end your life when you _____?*<br>　　*Or did you think it was possible you could have died from _____?*<br>*Or did you do it purely for other reasons / without ANY intention of killing yourself (like to relieve stress, feel better, get sympathy, or get something else to happen)? (Self-Injurious Behavior without suicidal intent)*<br>If yes, describe: | Yes ☐　No ☐ |
| | Total # of Attempts<br>_____ |
| Has subject engaged in Non-Suicidal Self-Injurious Behavior? | Yes ☐　No ☐ |
| Interrupted Attempt:<br>When the person is interrupted (by an outside circumstance) from starting the potentially self-injurious act *(if not for that, actual attempt would have occurred).*<br>Overdose: Person has pills in hand but is stopped from ingesting. Once they ingest any pills, this becomes an attempt rather than an interrupted attempt. Shooting: Person has gun pointed toward self, gun is taken away by someone else or is somehow prevented from pulling the trigger. Once they pull the trigger, even if the gun fails to fire, it is an attempt. Jumping: Person is poised to jump, is grabbed and taken down from ledge. Hanging: Person has noose around neck but has not yet started to hang - is stopped from doing so.<br>*Has there been a time when you started to do something to end your life but someone stopped you before you actually did anything?*<br>If yes, describe: | Yes ☐　No ☐ |
| | Total # of interrupted<br>_____ |

FIGURE 10 (Continued)

| Question / Item | Response |
|---|---|
| Aborted Attempt:<br>When person begins to take steps toward making a suicide attempt, but stops themselves before they actually have engaged in any self-destructive behavior. Examples are similar to interrupted attempts, except that the individual stops him/herself, instead of being stopped by something else.<br>*Has there been a time when you started to do something to try to end your life but you stopped yourself before you actually did anything?*<br>If yes, describe: | Yes ☐  No ☐<br>Total # of Aborted<br>_____ |
| Preparatory Acts or Behavior:<br>Acts or preparation towards imminently making a suicide attempt. This can include anything beyond a verbalization or thought, such as assembling a specific method (e.g., buying pills, purchasing a gun) or preparing for one's death by suicide (e.g., giving things away, writing a suicide note).<br>*Have you taken any steps towards making a suicide attempt or preparing to kill yourself (such as collecting pills, getting a gun, giving valuables away or writing a suicide note)?*<br>If yes, describe: | Yes ☐  No ☐ |
| Suicidal Behavior:<br>Suicidal behavior was present during the assessment period? | Yes ☐  No ☐ |
| Suicide: | Yes ☐  No ☐ |
| *Answer for Actual Attempts Only* | Most Lethal Attempt Date: |
| Actual Lethality/Medical Damage:<br>0. No physical damage or very minor physical damage (e.g., surface scratches).<br>1. Minor physical damage (e.g., lethargic speech; first degree burns; mild bleeding; sprains).<br>2. Moderate physical damage; medical attention needed (e.g., conscious but sleepy, somewhat responsive; second-degree burns; bleeding of major vessel).<br>3. Moderately severe physical damage; *medical* hospitalization and likely intensive care required (e.g., comatose with reflexes intact; third-degree burns less than 20% of body; extensive blood loss but can recover; major fractures).<br>4. Severe physical damage; medical hospitalization with intensive care required (e.g., comatose without reflexes; third-degree burns over 20% of body; extensive blood loss with unstable vital signs; major damage to a vital area).<br>5. Death | *Enter Code*<br>_____ |
| Potential Liability: Only Answer if Actual Lethality=0<br>Likely lethality of actual attempt if no medical damage (the following examples, while having no actual medical damage, had potential for very serious lethality: put gun in mouth and pulled the trigger but gun fails to fire so no medical damage; laying on train tracks with oncoming train but pulled away before run over).<br>0 = Behavior not likely to result in injury<br>1 = Behavior likely to result in injury but not likely to cause death<br>2 = Behavior likely to result in death despite available medical care | *Enter Code*<br>_____ |

FIGURE 10 (Continued)

| | Since Last Visit |
|---|---|
| SUICIDAL IDEATION | |
| *Ask questions 1 and 2. If both are negative, proceed to "Suicidal Behavior" section. If the answer to question 2 is "yes", ask questions 3, 4 and 5. If the answer to question 1 and/or 2 is "yes", complete "Intensity" of Ideation" section below.* | |
| 1. Wish to be Dead<br>Subject endorses thoughts about a wish to be dead or not alive anymore, or wish to fall asleep and not wake up.<br>*Have you wished you were dead or wished you could go sleep and not wake up?*<br><br>If yes, describe: | Yes ☐   No ☐ |
| 2. Non-Specific Active Suicidal Thoughts<br>General, non-specific thoughts of wanting to end one's life/commit suicidal (e.g., "'I've thought about killing myself"') without thoughts of ways to kill oneself/associated methods, intent, or plan during the assessment period.<br>*Have you actually had any thoughts of killing yourself?*<br><br>If yes, describe: | Yes ☐   No ☐ |
| 3. Active Suicidal Ideation with Any Methods (Not Plan) without Intent to Act<br>Subject endorses thoughts of suicide and has thought of at least one method during the assessment period. This is different than a specific plan with time, place or method details worked out (e.g., thought of method to kill self but not a specific plan). Includes person who would say, "'I thought about taking an overdose but I never made a specific plan as to when, where or how I would actually do it...and I would never go through with it."<br>*Have you been thinking about how you might do this?*<br><br>If yes, describe: | Yes ☐   No ☐ |
| 4. Active Suicidal Ideation with Some Intent to Act, without Specific Plan<br>Active suicidal thoughts of killing oneself and subject reports having some intent to act on such thoughts, as opposed to "I have the thoughts but I definitely will not do anything about them."<br>*Have you had these thoughts and had some intention of acting on them?*<br><br>If yes, describe: | Yes ☐   No ☐ |
| 5. Active Suicidal Ideation with Specific Plan and Intent<br>Thoughts of killing oneself with details of plan fully or partially worked out and subject has some intent to carry it out.<br>*Have you started to work out or worked out the details of how to kill yourself? Do you intend to carry out this plan?*<br><br>If yes, describe: | Yes ☐   No ☐ |

FIGURE 11

| | Most Severe |
|---|---|
| INTENSITY OF IDEATION | |
| The following features should be rated with respect to the most severe type of ideation (i.e., 1-5 from above, with 1 being the least severe and 5 being the most severe). | |
| Most Severe Ideation:     <u>Type # (1-5)</u>     Description of Ideation | _____ |
| Frequency<br>How many times have you had these thoughts?<br>(1) Less than once a week  (2) Once a week  (3) 2-5 times in week  (4) Daily or almost daily  (5) Many times each day | _____ |
| Duration<br>When you have the thoughts, how long do they last?<br>(1) Fleeting - few seconds or minutes   (3) 1-4 hours/a lot of time   (5) More than 8 hours/persistent or continuous<br>(2) Less than 1 hour/some of the time   (4) 4-8 hours/most of day | _____ |
| Controllability<br>Could/can you stop thinking about killing yourself or wanting to die if you want to?<br>(1) Easily able to control thoughts   (3) Can control thoughts with some difficulty   (5) Unable to control thoughts<br>(2) Can control thoughts with little difficulty  (4) Can control thoughts with a lot of difficulty  (6) Does not attempt to control thoughts | _____ |
| Deterrents<br>Are there things - anyone or anything (e.g., family, religion, pain of death)-that stopped you from wanting to die or acting on thoughts of committing suicide?<br>(1) Deterrents definitely stopped you from  (3) Uncertain that deterrents stopped you  (5) Deterrents definitely did not stop you<br>    attempting suicide    (4) Deterrents most likely did not stop you  (0) Does not apply<br>(2) Deterrents probably stopped you | _____ |
| Reasons for Ideation<br>What sort of reasons did you have for thinking about wanting to die or killing yourself? Was it to end the pain or stop the way you were feeling (in other words you couldn't go on living with this pain or how you were feeling) or was it to get attention, revenge or a reaction from others? Or both?<br>(1) Completely to get attention, revenge or a reaction from others    (5) Completely to end or stop the pain (you couldn't go on<br>(2) Mostly to get attention, revenge or a reaction from others           living with the pain or how you were feeling)<br>(3) Equally to get attention, revenge or a reaction from others and to    (0) Does not apply<br>    end/stop the pain<br>(4) Mostly to end or stop the pain (you couldn't go on living with the<br>    pain or how you were feeling) | _____ |

FIGURE 11 (Continued)

METHOD OF TREATING NEUROMYELITIS OPTICA SPECTRUM DISORDER (NMOSD) COMPRISING ADMINISTERING AN ANTI-C5 ANTIBODY

RELATED APPLICATIONS

This application claims the benefit of priority to U.S. Provisional Patent Application No. 62/945,644, filed Dec. 9, 2019 the entire contents of which are incorporated herein by reference for all purposes.

REFERENCE TO SEQUENCE LISTING SUBMITTED ELECTRONICALLY

The content of the electronically submitted sequence listing in ASCII text file (Name: 710476_AX9-007PC_ST25_Sequence_Listing.txt; Size: 56.0 KB; and Date of Creation: Dec. 8, 2020) is incorporated herein by reference in its entirety.

BACKGROUND

Neuromyelitis optica spectrum disorder (NMOSD), including neuromyelitis optica (NMO), also known as Devic's Disease, or Devic's Syndrome, is a class of rare, severe disabling autoimmune inflammatory disorders of the central nervous system (CNS) that predominately affects the optic nerves and spinal cord, often leading to blindness, mono/para/tetraplegia, and respiratory failure. NMOSD is characterized by a relapsing disease course, from which recovery may be poor due to the stepwise accumulation of significant neurologic disability.

The clinical hallmarks of NMO are acute optic neuritis and transverse myelitis that frequently involves greater than three vertebral levels, described as longitudinally extensive transverse myelitis (LETM). These clinical events can occur either simultaneously or in isolation. Signs and symptoms attributable to lesions beyond the optic nerves and spinal cord can also occur in patients with NMO, and are reported in about 15% of patients. The clinical presentation of NMO can be quite variable and may elude diagnosis at the time of the first attack or even the second attack.

Aquaporin-4 (AQP4) is a water channel protein expressed in the CNS, mainly by astrocytes. AQP4 immunoglobulin G (IgG), an antibody present in 65-88% of patients with NMOSD, is the first ever biomarker specific to an inflammatory, demyelinating CNS disorder. Preclinical data indicate that AQP4-IgG triggers the complement cascade, leading to inflammation and formation of the complement-mediated membrane attack complex (MAC). AQP4-IgG-triggered MAC has been implicated in astrocyte destruction and bystander neuronal injury, but is not seen in the presence of a complement inhibitor. With the discovery of NMO-IgG, the diagnostic criteria for NMO were revised in 2006 to include the testing of this disease-specific antibody.

In light of the fact that NMO is a disorder that has the potential to cause significant disability, the ability to recognize and differentiate NMO and related disorders from other demyelinating disorders is important from a clinical perspective. The prognosis of relapsing NMO is poor. The 5-year mortality of NMO was reported to be 30%; 50% sustain permanent severe disability, visual (blind in one or both eyes) or ambulatory (requiring a wheelchair). Most deaths result from neurogenic respiratory failure secondary to a high cervical cord or brainstem lesion. Frequent early relapses predict a poor prognosis. Relapse prevention is thus the primary therapeutic imperative.

Although treatment options for NMO have recently been approved (Soliris® (eculizumab) was proven to reduce relapse frequency in an open-label study in 14 patients with AQP4-IgG-positive disease), standard treatment options still include steroids and other immunosuppressive agents as supportive treatments based on clinical experience and consensus. Acute NMO relapses are generally treated with high-dose IV steroids with plasma exchange (PE) often used as a rescue therapy for those who do not respond. Supportive treatments against relapse currently use broad spectrum or selective B-lymphocyte immunosuppressants.

Of the immunosuppressive agents, corticosteroid, AZA, mycophenolate mofetile and rituximab are probably most commonly used for long-term prophylaxis. Depending on regional medical options, the supportive medications option for NMO may vary. In the US, options include corticosteroids, AZA, MMF, rituximab and mitoxantrone, whereas corticosteroids including oral prednisone or pulse-high dose steroids (IV) are common treatments in Japan. A significant number of patients (>50%) will continue to have attacks resulting in additional and permanent neurologic deficits and disability. Given the seriousness of the disease and the limited options for treatment, there remains a significant unmet medical need for an effective and safe treatment for NMO.

SUMMARY

Described herein are materials and methods for the treatment of NMOSD (e.g., NMO). In particular, such materials and methods comprise a C5 inhibitor (e.g., ravulizumab).

In one embodiment, the disclosure is directed to a method of treating neuromyelitis optica spectrum disorder (NMOSD) in a human subject in need thereof, comprising administering to the human subject an effective amount of an anti-C5 antibody or antigen binding fragment thereof, comprising CDR1, CDR2 and CDR3 heavy chain sequences as set forth in SEQ ID NOs:19, 18 and 3, respectively, and CDR1, CDR2 and CDR3 light chain sequences as set forth in SEQ ID NOs:4, 5 and 6, respectively, wherein the anti-C5 antibody or antigen binding fragment thereof comprises an Fc region comprising the amino acid sequence set forth in SEQ ID NO:13, wherein the amino acid sequence comprises at most four amino acid substitutions in the amino acid sequence set forth in SEQ ID NO:13, and wherein the amino acid substitutions do not include leucine 307 and serine 313, thereby treating NMOSD in the subject. In a particular embodiment, the anti-C5 antibody or antigen-binding fragment thereof comprises a heavy chain variable region depicted in SEQ ID NO:12 and a light chain variable region depicted in SEQ ID NO:8. In a particular embodiment, the anti-C5 antibody or antigen-binding fragment thereof comprises a heavy chain constant region depicted in SEQ ID NO:13. In a particular embodiment, the antibody or antigen-binding fragment thereof comprises a heavy chain polypeptide comprising the amino acid sequence of SEQ ID NO:14 and a light chain polypeptide comprising the amino acid sequence of SEQ ID NO:11. In a particular embodiment, the anti-C5 antibody or antigen-binding fragment thereof binds to human C5 at pH 7.4 and 25° C. with an affinity dissociation constant (Ki) that is in the range $0.1 \text{ nM} \leq K_D \leq 1 \text{ nM}$. In a particular embodiment, the anti-C5 antibody or antigen-binding fragment thereof binds to human C5 at pH 6.0 and 25° C. with a $K_D \geq 10 \text{ nM}$. In a particular embodiment, the subject is 18 years old or older in age. In a particular embodiment, the subject is positive for anti-AQP4 antibody. In a particular embodiment, the subject has at least one attack or relapse in the past 12 months. In a particular embodiment, the subject has an Expanded Disability Status Scale (EDSS) score ≤7. In a particular embodiment, the anti-C5 antibody is administered without additional immunosuppressive therapies (ISTs). In a particular embodiment, the anti-C5 antibody is administered with at least one IST. In a particular embodiment, the at least one IST is selected from the group consisting of a corticosteroid, azathioprine (AZA), mycophenolate mofetil (MMF), methotrexate (MTX), and tacrolimus (TAC). In a particular embodiment, the subject weighs at least 40 kg. In a particular embodiment, the therapeutically effective dose is based on the weight of the subject. In a particular embodiment, the subject shows at least one symptom of NMOSD. In a particular embodiment, the subject weighs ≥40 and <60 kg, and wherein (a) the anti-C5 antibody is administered on Day 1 of an administration cycle at a loading dose of 2400 mg; and (b) on Day 15 of the administration cycle and every eight weeks thereafter at a maintenance dose of 3000 mg. In a particular embodiment, the subject weighs ≥60 and <100 kg, and wherein (a) the anti-C5 antibody is administered on Day 1 of an administration cycle at a loading dose of 2700 mg; and (b) on Day 15 of the administration cycle and every eight weeks thereafter at a maintenance dose of 3300 mg. In a particular embodiment, the subject weighs ≥100 kg, and wherein (a) the anti-C5 antibody is administered on Day 1 of an administration cycle at a loading dose of 3000 mg; and (b) on Day 15 of the administration cycle and every eight weeks thereafter at a maintenance dose of 3600 mg. In a particular embodiment, the treatment maintains a serum trough concentration of the anti-C5 antibody or antigen binding fragment thereof of 100 µg/mL or greater during the administration cycle. In a particular embodiment, the treatment maintains a serum trough concentration of the anti-C5 antibody or antigen binding fragment thereof of 200 µg/m L or greater during the administration cycle. In a particular embodiment, the treatment maintains a free C5 concentration of 0.309 to 0.5 µg/mL or lower. In a particular embodiment, the anti-C5 antibody or antigen binding fragment thereof is administered at a dose of 3000 mg, 3300 mg or 3600 mg every eight weeks after the administration cycle for up to two years. In a particular embodiment, the anti-C5 antibody or antigen binding fragment thereof is formulated for intravenous administration. In a particular embodiment, the patient has not previously been treated with a complement inhibitor. In a particular embodiment, the administration cycle is a total of 26 weeks of treatment. In a particular embodiment, the treatment results in terminal complement inhibition. In a particular embodiment, the subject receives plasma exchange (PE)/plasmapheresis (PP), and wherein the subject optionally receives a supplemental dose of ravulizumab, e.g., between 1200-1800 mg of anti-C5 antibody, within 4 hours after PE/PP is completed. In a particular embodiment, the human subject experiences a clinically meaningful improvement in one or more clinical markers for NMOSD progression after administration of ravulizumab. In a particular embodiment, clinical markers for NMOSD progression are selected from a group consisting of adjudicated On-Trial ARR, EDSS score, EQ-5D, SF-36, HAI and OSIS.

BRIEF DESCRIPTION OF THE DRAWINGS

FIG. 1 is a schematic of the overall design of the clinical trial disclosed herein.

FIG. 2 is a table showing the Schedule of Activities (SoA) for the clinical trial disclosed herein.

FIG. 3 is a table showing the Schedule of Activities (SoA) the for relapse evaluation period for the clinical trial disclosed herein.

FIG. 4 is a table showing the Kurtzke Expanded Disability Status Scale.

FIG. 5 is a checklist and chart for EuroQoL 5 dimensions (EQ-5D-3L) scale.

FIG. 6 is a short form Health Survey (SF-36).

FIG. 7 is a checklist for the Hauser Ambulation Index (HAI).

FIG. 8 is a chart for the Optic Spinal Impairment Score (OSIS).

FIG. 9 is a table showing the Relapse Severity as Measured by Optic Spinal Impairment Scale.

FIG. 10 is a checklist for the Columbia Suicide Severity Rating Scale (C-SSRS)-Screening/Baseline.

FIG. 11 is a checklist for the Columbia-Suicide Severity Rating Scale (C-SSRS)-Since Last Visit.

DETAILED DESCRIPTION

The disclosure provides methods of treating neuromyelitis optica spectrum disorder (NMOSD) in subjects in need thereof by administering an antibody that specifically binds complement component 5 (C5). In certain embodiments, the antibody that specifically binds C5 reduces the rate at which C5 is cleaved in vivo into C5a and C5b. In other embodiments, the antibody that specifically binds C5 binds to one or both of the C5a and/or C5b fragments. In any of these embodiments, the antibody that specifically binds C5 reduces the complement cascade at C5, thereby reducing the release of proinflammatory mediators and the formation of a cytolytic pore.

In certain embodiments, the antibody that specifically binds C5 is ravulizumab or a fragment thereof. Ravulizumab (also known as BNJ441, ALXN1210 or Ultomiris®) is an anti-C5 antibody comprising heavy and light chains having the sequences shown in SEQ ID NOs:14 and 11, respectively, or antigen binding fragments and variants thereof. Ravulizumab is described in PCT/US2015/019225 and U.S. Pat. No. 9,079,949, the entire teachings of which are hereby incorporated by reference. Ravulizumab selectively binds to human complement protein C5, inhibiting its cleavage to C5a and C5b during complement activation. This inhibition prevents the release of the proinflammatory mediator C5a and the formation of the cytolytic pore-forming membrane attack complex (MAC), C5b-9, while preserving the proximal or early components of complement activation (e.g., C3 and C3b) essential for the opsonization of microorganisms and clearance of immune complexes.

DEFINITIONS

As used herein, the term "subject" or "patient" is a human patient (e.g., a patient having neuromyelitis optica spectrum disorder (NMOSD)). As used herein, the term "subject" and "patient" are interchangeable.

As used herein, the phrase "requires chronic plasma exchange" to maintain clinical stability refers to the use of plasma exchange therapy on a patient on a regular basis for the management of muscle weakness at least every 3 months over the last 12 months.

As used herein, "effective treatment" refers to treatment producing a beneficial effect, e.g., amelioration of at least one symptom of a disease or disorder. A beneficial effect can take the form of an improvement over baseline, i.e., an improvement over a measurement or observation made prior to initiation of therapy according to the method. Effective treatment may refer to alleviation of at least one symptom of NMOSD.

The term "effective amount" refers to an amount of an agent that provides the desired biological, therapeutic and/or prophylactic result. That result can be reduction, amelioration, palliation, lessening, delaying and/or alleviation of one or more of the signs, symptoms or causes of a disease, or any other desired alteration of a biological system. In one example, an "effective amount" is the amount of anti-C5 antibody or antigen binding fragment thereof clinically proven to alleviate at least one symptom of NMOSD. An effective amount can be administered in one or more administrations.

As used herein, the terms "induction" and "induction phase" are used interchangeably and refer to the first phase of treatment in the clinical trial.

As used herein, the terms "maintenance" and "maintenance phase" are used interchangeably and refer to the second phase of treatment in the clinical trial. In certain embodiments, treatment is continued as long as clinical benefit is observed or until unmanageable toxicity or disease progression occurs. The maintenance phase of ravulizumab dosing can last for between 6 weeks and the life of the subject. According to other embodiments, the maintenance phase lasts for 26-52, 26-78, 26-104, 26-130, 26-156, 26-182, 26-208 weeks, or more. In other embodiments, the maintenance phase lasts for greater than 26, 27, 28, 29, 30, 31, 32, 33, 34, 35, 36, 37, 38, 39, 40, 41, 42, 43, 44, 45, 46, 47, 48, 49, 50, 51, 52, 78, 104, 130, 156, or 182 weeks. According to other embodiments, the maintenance phase lasts for greater than 1, 2, 3, 4, 5, 10, 15, 20, 25, 30, 35, 40, 45, 50, 55, 60, 65, 70, 75, 80 or more years. In certain embodiments, the maintenance phase lasts for the remainder of the subject's life.

In certain embodiments, the ravulizumab multiphase dosing regimen includes a third phase. This third phase is used when an NMOSD patient must undergo a rescue procedure to maintain clinical stability and includes administering plasma exchange/plasmapheresis (PE/PP). In this phase after plasma is exchanged a dose of ravulizumab is administered to replace the drug lost in plasma exchange/plasmapheresis. According to certain embodiments, supplemental study drug (or placebo) dosing is required if PE/PP rescue therapy is provided on non-dosing days. In another embodiment, if PE/PP infusion is provided on a dosing day, it must occur prior to study drug administration. In some embodiments, if PE/PP is administered on nonscheduled dosing visits, patients receiving PE/PP are administered a supplemental dose within 1, 2, 3, 4, 5, 6, 7 or 8 hours after the PE/PP session is completed.

In some embodiments, if PE/PP is administered on nonscheduled dosing visits, patients receiving PE/PP are administered a supplemental dose within 4 hours after the PE/PP session is completed. In certain embodiments, supplemental dose amounts may or may not vary depending on PE/PP. In other embodiments, if PE/PP is administered on scheduled dosing visits, regular dosing is followed 60 minutes after the completion of PE/PP. In certain embodiments, no gap is required between a supplemental dose and the regular scheduled dose.

In some embodiments, the supplemental dose of ravulizumab is administered at between 1000 and 2000 mg. In some embodiments, the supplemental dose of ravulizumab is administered at about half the most recent loading or maintenance dose of ravulizumab. In some embodiments, if the most recent loading dose is between 2200 mg and 3000 mg of ravulizumab, the supplemental dose is 1000-1500 mg of ravulizumab. In some embodiments, if the most recent loading dose is about 2400 mg of ravulizumab, the supplemental dose is about 1200 mg of ravulizumab. In some embodiments, if the most recent loading dose is 2400 mg of ravulizumab, the supplemental dose is 1200 mg of ravulizumab. In some embodiments, if the most recent loading dose is about 2700 mg of ravulizumab, the supplemental dose is about 1500 mg of ravulizumab. In some embodiments, if the most recent loading dose is 2700 mg of ravulizumab, the supplemental dose is 1500 mg of ravulizumab. In some embodiments, if the most recent loading dose is about 3000 mg of ravulizumab, the supplemental dose is about 1500 mg of ravulizumab. In some embodiments, if the most recent loading dose is 3000 mg of ravulizumab, the supplemental dose is 1500 mg of ravulizumab. In some embodiments, if the most recent maintenance dose is about 3000 mg of ravulizumab, the supplemental dose is about 1500 mg of ravulizumab. In some embodiments, if the most maintenance loading dose is 3000 mg of ravulizumab, the supplemental dose is 1500 mg of ravulizumab. In some embodiments, if the most recent maintenance dose is about 3300 mg of ravulizumab, the supplemental dose is about 1800 mg of ravulizumab. In some embodiments, if the most maintenance loading dose is 3300 mg of ravulizumab, the supplemental dose is 1800 mg of ravulizumab. In some embodiments, if the most recent maintenance dose is about 3600 mg of ravulizumab, the supplemental dose is about 1800 mg of ravulizumab. In some embodiments, if the most maintenance loading dose is 3600 mg of ravulizumab, the supplemental dose is 1800 mg of ravulizumab.

As used herein, the terms "loading dose" refers to the initial dose administered to the patient. In some embodiments, the loading dose is 2000-4000 mg of ravulizumab. In some embodiments, the loading dose is 2100-2700 mg, 2400-3000 mg or 2700-3300 mg of ravulizumab. In some embodiments, the loading dose is 2300-2500 mg, 2600-2800 mg or 2900-3100 mg of ravulizumab. In some embodiments, the loading dose is about 2400 mg, about 2700 mg, or about 3000 mg of ravulizumab. In some embodiments, the loading dose is 2400 mg, 2700 mg, or 3000 mg of ravulizumab. Loading doses may be titered based on body weight.

In some embodiments, patients with a body weight greater than or equal to 40 kg, but less than 60 kg is administered 2100-2700 mg, 2300-2500 mg, about 2400 mg or 2400 mg of ravulizumab. In some embodiments, patients with a body weight greater than or equal to 60 kg, but less than 100 kg is administered 2400-3000 mg, 2600-2800 mg, about 2700 mg or 2700 mg of ravulizumab. In some embodiments, patients with a body weight greater than 100 kg is administered 2700-3300 mg, 2900-3100 mg, about 3000 mg or 3000 mg of ravulizumab.

As used herein, the terms "maintenance dose" or "maintenance phase" refers to a dose administered to the patient after the loading dose. In some embodiments, the loading dose is 2000-4000 mg of ravulizumab. In some embodiments, the loading dose is 2800-3200 mg, 3100-3500 mg or 3400-3800 mg of ravulizumab. In some embodiments, the loading dose is 2900-3100 mg, 3200-3400 mg or 3500-3700 mg of ravulizumab. In some embodiments, the loading dose is about 3000 mg, about 3300 mg, or about 3600 mg of ravulizumab. In some embodiments, the loading dose is 3000 mg, 3300 mg, or 3600 mg of ravulizumab. Maintenance doses may be titered based on body weight.

In some embodiments, patients with a body weight greater than or equal to 40 kg, but less than 60 kg is administered 2800-3200 mg, 2900-3100 mg, about 3000 mg or 3000 mg of ravulizumab. In some embodiments, patients with a body weight greater than or equal to 60 kg, but less than 100 kg is administered 3100-3500 mg, 3200-3400 mg, about 3300 mg or 3300 mg of ravulizumab. In some embodiments, patients with a body weight greater than 100 kg is administered 3400-3800 mg, 3500-3700 mg, about 3600 mg or 3600 mg of ravulizumab.

As used herein, the term "serum trough level" refers to the lowest level that the agent (e.g., the anti-C5 antibody, or antigen binding fragment thereof) or medicine is present in the serum. In contrast, a "peak serum level," refers to the highest level of the agent in the serum. The "average serum level," refers to the mean level of the agent in the serum over time.

In one embodiment, the treatment regimens described are sufficient to maintain particular serum trough concentrations of the anti-C5 antibody or antigen binding fragment thereof. In one embodiment, for example, the treatment maintains a serum trough concentration of the anti-C5 antibody, or antigen binding fragment thereof, of 50, 55, 60, 65, 70, 75, 80, 85, 90, 95, 100, 105, 110, 115, 120, 125, 130, 135, 140, 145, 150, 155, 160, 165, 170, 175, 180, 185, 190, 200, 205, 210, 215, 220, 225, 230, 240, 245, 250, 255, 260, 265, 270, 280, 290, 300, 305, 310, 315, 320, 325, 330, 335, 340, 345, 350, 355, 360, 365, 370, 375, 380, 385, 390, 395 or 400 μg/mL or greater. In one embodiment, the treatment maintains a serum trough concentration of the anti-C5 antibody, or antigen binding fragment thereof, of 100 μg/mL or greater. In another embodiment, the treatment maintains a serum trough concentration of the anti-C5 antibody or antigen binding fragment thereof of 150 μg/mL or greater. In another embodiment, the treatment maintains a serum trough concentration of the anti-C5 antibody or antigen binding fragment thereof of 200 μg/mL or greater. In another embodiment, the treatment maintains a serum trough concentration of the anti-C5 antibody, or antigen binding fragment thereof, of 250 μg/mL or greater. In another embodiment, the treatment maintains a serum trough concentration of the anti-C5 antibody, or antigen binding fragment thereof, of 300 μg/mL or greater. In another embodiment, the treatment maintains a serum trough concentration of the anti-C5 antibody, or antigen binding fragment thereof, of between 100 μg/mL and 200 μg/mL. In another embodiment, the treatment maintains a serum trough concentration of the anti-C5 antibody, or antigen binding fragment thereof, of about 175 μg/mL.

In another embodiment, to obtain an effective response, the anti-C5 antibody is administered to the patient in an amount and with a frequency to maintain at least 50 μg, 55 μg, 60 μg, 65 μg, 70 μg, 75 μg, 80 μg, 85 μg, 90 μg, 95 μg, 100 μg, 105 μg, 110 μg, 115 μg, 120 μg, 125 μg, 130 μg, 135 μg, 140 μg, 145 μg, 150 μg, 155 μg, 160 μg, 165 μg, 170 μg, 175 μg, 180 μg, 185 μg, 190 μg, 195 μg, 200 μg, 205 μg, 210 μg, 215 μg, 220 μg, 225 μg, 230 μg, 235 μg, 240 μg, 245 μg, 250 μg, 255 μg, or 260 μg of antibody per milliliter of the patient's blood. In another embodiment, the anti-C5 antibody is administered to the patient in an amount and with a frequency to maintain between 50 μg and 250 μg of antibody per milliliter of the patient's blood. In another embodiment, the anti-C5 antibody is administered to the patient in an amount and with a frequency to maintain between 100 μg and 200 μg of antibody per milliliter of the patient's blood. In another embodiment, the anti-C5 antibody is administered to the patient in an amount and with a frequency to maintain about 175 μg of antibody per milliliter of the patient's blood.

In another embodiment, to obtain an effective response, the anti-C5 antibody is administered to the patient in an amount and with a frequency to maintain a minimum free C5 concentration. In one embodiment, for example, the anti-C5 antibody is administered to the patient in an amount and with a frequency to maintain a free C5 concentration of 0.2 μg/mL, 0.3 μg/mL, 0.4 μg/mL, 0.5 μg/mL or below. In another embodiment, the anti-C5 antibody is administered to the patient in an amount and with a frequency to maintain a free C5 concentration of 0.309 to 0.5 μg/mL or below. In another embodiment, the treatment described herein reduces free C5 concentration by greater than 99% throughout the treatment period. In another embodiment, the treatment reduces free C5 concentration greater than 99.5% throughout the treatment period.

The term "terminal complement inhibition" refers to the inhibition of the late stage of the complement cascade. In one embodiment, terminal complement inhibition refers to inhibition of complement component 5 ("C5") from being cleaved by the C5 convertase into C5a and C5b.

The term "antibody" describes polypeptides comprising at least one antibody derived antigen binding site (e.g., VH/VL region or Fv, or CDR). Antibodies include known forms of antibodies. The antibody, for example, can be a human antibody, a humanized antibody, a camelid antibody, a bispecific antibody or a chimeric antibody. The antibody also can be a Fab, Fab'2, ScFv, SMIP, Affibody, nanobody or a domain antibody. The antibody also can be of any of the following isotypes: IgG1, IgG2, IgG3, IgG4, IgM, IgA1, IgA2, IgAsec, IgD and IgE. The antibody may be a naturally occurring antibody or may be an antibody that has been altered by a protein engineering technique (e.g., by mutation, deletion, substitution, conjugation to a non-antibody moiety). An antibody may include, for example, one or more variant amino acids (compared to a naturally occurring antibody), which changes a property (e.g., a functional property) of the antibody. Numerous such alterations are known in the art that affect, e.g., half-life, effector function, and/or immune responses to the antibody in a patient. The term antibody also includes artificial or engineered polypeptide constructs that comprise at least one antibody-derived antigen binding site.

C5 Binding Proteins

The term "antibody" describes polypeptides comprising at least one antibody derived antigen binding site (e.g., VH/VL region or Fv, or CDR). Antibodies include known forms of antibodies. The antibody can be, for example, a human antibody, a humanized antibody, a bispecific antibody or a chimeric antibody. The antibody also can be a Fab, Fab'2, ScFv, SMIP, Affibody, nanobody, or a domain antibody. The antibody also can be of any of the following isotypes: IgG1, IgG2, IgG3, IgG4, IgM, IgA1, IgA2, IgAsec, IgD or IgE. The antibody can be a naturally occurring antibody or may be an antibody that has been altered by a protein engineering technique (e.g., by mutation, deletion, substitution, conjugation to a non-antibody moiety). An antibody can include, for example, one or more variant amino acids (compared to a naturally occurring antibody), which changes a property (e.g., a functional property) of the antibody. Such alterations are known in the art that affect, e.g., half-life, effector function, and/or immune responses to the antibody in a patient. The term antibody also includes artificial or engineered polypeptide constructs that comprise at least one antibody-derived antigen binding site.

The anti-C5 antibodies described herein bind to complement component C5 (e.g., human C5) and inhibit the cleavage of C5 into fragments C5a and C5b. Anti-C5 antibodies (or VH/VL domains derived therefrom) suitable for use in methods described herein can be generated using methods known in the art. Alternatively, art-recognized anti-C5 antibodies can be used. Antibodies that compete with any of these art-recognized antibodies for binding to C5 also can be used.

Eculizumab (also known as Soliris®) is an anti-C5 antibody comprising heavy and light chains having sequences shown in SEQ ID NO: 10 and 11, respectively, or antigen binding fragments and variants thereof. Eculizumab is described in PCT/US2007/006606, the teachings of which are hereby incorporated by reference. In one embodiment the anti-C5 antibody, comprises the CDR1, CDR2, and CDR3 domains of the VH region of eculizumab having the sequence set forth in SEQ ID NO: 7, and the CDR1, CDR2 and CDR3 domains of the VL region of eculizumab having the sequence set forth in SEQ ID NO: 8. In another embodiment, the antibody comprises heavy chain CDR1, CDR2 and CDR3 domains having the sequences set forth in SEQ ID NOs: 1, 2, and 3, respectively, and light chain CDR1, CDR2 and CDR3 domains having the sequences set forth in SEQ ID NOs: 4, 5, and 6, respectively. In another embodiment, the antibody comprises VH and VL regions having the amino acid sequences set forth in SEQ ID NO: 7 and SEQ ID NO: 8, respectively.

Ravulizumab (also known as BNJ441, ALXN1210 or Ultomiris@) is an anti-C5 antibody comprising heavy and light chains having the sequences shown in SEQ ID NOs:14 and 11, respectively, or antigen binding fragments and variants thereof. Ravulizumab is described in PCT/US2015/019225 and U.S. Pat. No. 9,079,949, the teachings of which are hereby incorporated by reference. Ravulizumab selectively binds to human complement protein C5, inhibiting its cleavage to C5a and C5b during complement activation. This inhibition prevents the release of the proinflammatory mediator C5a and the formation of the cytolytic pore-forming membrane attack complex (MAC) C5b-9 while preserving the proximal or early components of complement activation (e.g., C3 and C3b) essential for the opsonization of microorganisms and clearance of immune complexes.

In one embodiment, the antibody comprises the heavy and light chain CDRs or variable regions of ravulizumab. Accordingly, in one embodiment, the antibody comprises the CDR1, CDR2, and CDR3 domains of the VH region of ravulizumab having the sequence set forth in SEQ ID NO:12, and the CDR1, CDR2 and CDR3 domains of the VL region of ravulizumab having the sequence set forth in SEQ ID NO:8. In another embodiment, the antibody comprises heavy chain CDR1, CDR2 and CDR3 domains having the sequences set forth in SEQ ID NOs:19, 18, and 3, respectively, and light chain CDR1, CDR2 and CDR3 domains having the sequences set forth in SEQ ID NOs:4, 5, and 6, respectively. In another embodiment, the antibody comprises VH and VL regions having the amino acid sequences set forth in SEQ ID NO:12 and SEQ ID NO:8, respectively.

Another exemplary anti-C5 antibody is antibody BNJ421 comprising heavy and light chains having the sequences shown in SEQ ID NOs:20 and 11, respectively, or antigen binding fragments and variants thereof. BNJ421 (also known as ALXN1211) is described in PCT/US2015/019225 and U.S. Pat. No. 9,079,949, the teachings of which are hereby incorporated by reference.

In other embodiments, the antibody comprises the heavy and light chain CDRs or variable regions of BNJ421. Accordingly, in one embodiment, the antibody comprises the CDR1, CDR2, and CDR3 domains of the VH region of BNJ421 having the sequence set forth in SEQ ID NO:12, and the CDR1, CDR2 and CDR3 domains of the VL region of BNJ421 having the sequence set forth in SEQ ID NO:8. In another embodiment, the antibody comprises heavy chain CDR1, CDR2 and CDR3 domains having the sequences set forth in SEQ ID NOs:19, 18, and 3, respectively, and light chain CDR1, CDR2 and CDR3 domains having the sequences set forth in SEQ ID NOs:4, 5, and 6, respectively. In another embodiment, the antibody comprises VH and VL regions having the amino acid sequences set forth in SEQ ID NO:12 and SEQ ID NO:8, respectively.

The exact boundaries of CDRs have been defined differently according to different methods. In some embodiments, the positions of the CDRs or framework regions within a light or heavy chain variable domain can be as defined by Kabat et al. [(1991) "Sequences of Proteins of Immunological Interest." NIH Publication No. 91-3242, U.S. Department of Health and Human Services, Bethesda, Md.]. In such cases, the CDRs can be referred to as "Kabat CDRs" (e.g., "Kabat LCDR2" or "Kabat HCDR1"). In some embodiments, the positions of the CDRs of a light or heavy chain variable region can be as defined by Chothia et al., *Nature*, 342:877-83, 1989. Accordingly, these regions can be referred to as "Chothia CDRs" (e.g., "Chothia LCDR2" or "Chothia HCDR3"). In some embodiments, the positions of the CDRs of the light and heavy chain variable regions can be as defined by a Kabat-Chothia combined definition. In such embodiments, these regions can be referred to as "combined Kabat-Chothia CDRs." Thomas et al. (*Mol. Immunol.*, 33:1389-401, 1996) exemplifies the identification of CDR boundaries according to Kabat and Chothia definitions.

Another exemplary anti-C5 antibody is the 7086 antibody described in U.S. Pat. Nos. 8,241,628 and 8,883,158. In one embodiment, the antibody comprises the heavy and light chain CDRs or variable regions of the 7086 antibody (see U.S. Pat. Nos. 8,241,628 and 8,883,158). In another embodiment, the antibody, or antigen binding fragment thereof, comprises heavy chain CDR1, CDR2 and CDR3 domains having the sequences set forth in SEQ ID NOs: 21, 22, and 23, respectively, and light chain CDR1, CDR2 and CDR3 domains having the sequences set forth in SEQ ID NOs: 24, 25, and 26, respectively. In another embodiment, the antibody, or antigen binding fragment thereof, comprises the VH region of the 7086 antibody having the sequence set forth in SEQ ID NO:27, and the VL region of the 7086 antibody having the sequence set forth in SEQ ID NO:28.

Another exemplary anti-C5 antibody is the 8110 antibody also described in U.S. Pat. Nos. 8,241,628 and 8,883,158. In one embodiment, the antibody comprises the heavy and light chain CDRs or variable regions of the 8110 antibody. In another embodiment, the antibody, or antigen binding fragment thereof, comprises heavy chain CDR1, CDR2 and CDR3 domains having the sequences set forth in SEQ ID NOs: 29, 30, and 31, respectively, and light chain CDR1, CDR2 and CDR3 domains having the sequences set forth in SEQ ID NOs: 32, 33, and 34, respectively. In another embodiment, the antibody comprises the VH region of the 8110 antibody having the sequence set forth in SEQ ID NO:

35, and the VL region of the 8110 antibody having the sequence set forth in SEQ ID NO: 36.

Another exemplary anti-C5 antibody is the 305LO5 antibody described in US2016/0176954A1. In one embodiment, the antibody comprises the heavy and light chain CDRs or variable regions of the 305LO5 antibody. In another embodiment, the antibody, or antigen binding fragment thereof, comprises heavy chain CDR1, CDR2 and CDR3 domains having the sequences set forth in SEQ ID NOs: 37, 38, and 39, respectively, and light chain CDR1, CDR2 and CDR3 domains having the sequences set forth in SEQ ID NOs: 40, 41, and 42, respectively. In another embodiment, the antibody comprises the VH region of the 305LO5 antibody having the sequence set forth in SEQ ID NO: 43, and the VL region of the 305LO5 antibody having the sequence set forth in SEQ ID NO: 44.

Another exemplary anti-C5 antibody is the SKY59 antibody described in Fukuzawa, T. et al. (*Sci. Rep.*, 7:1080, 2017). In one embodiment, the antibody comprises the heavy and light chain CDRs or variable regions of the SKY59 antibody. In another embodiment, the antibody, or antigen binding fragment thereof, comprises a heavy chain comprising SEQ ID NO: 45 and a light chain comprising SEQ ID NO: 46.

Another exemplary anti-C5 antibody is the H4H12166PP antibody described in PCT/US2017/037226 and US2017/0355757A1. In one embodiment, the antibody comprises the heavy and light chain CDRs or variable regions of the H4H12166PP antibody. In another embodiment, the antibody, or antigen binding fragment thereof, comprises VH region of the H4H12166PP antibody having the sequence set forth in SEQ ID NO:47, and the VL region of the H4H12166PP antibody having the sequence set forth in SEQ ID NO:48. In another embodiment, the antibody, or antigen binding fragment thereof, comprises a heavy chain comprising SEQ ID NO:49 and a light chain comprising SEQ ID NO:50.

In one embodiment, the patient is treated with eculizumab and then switched to treatment with the 7086 antibody, the 8110 antibody, the 305LO5 antibody, the SKY59 antibody, the H4H12166PP antibody or ravulizumab. In another embodiment, the patient is switched from an anti-C5 antibody (e.g., eculizumab, the 7086 antibody, the 8110 antibody, the 305LO5 antibody, the SKY59 antibody, or the H4H12166PP antibody) to another anti-C5 antibody (e.g., ravulizumab) during the course of treatment. In a particular embodiment, the patient is switched from eculizumab to ravulizumab during the course of treatment.

In some embodiments, an anti-C5 antibody described herein comprises a heavy chain CDR1 comprising, or consisting of, the following amino acid sequence: GHIFSNY-WIQ (SEQ ID NO:19). In some embodiments, an anti-C5 antibody described herein comprises a heavy chain CDR2 comprising, or consisting of, the following amino acid sequence: EILPGSGHTEYTENFKD (SEQ ID NO:18). In some embodiments, an anti-C5 antibody described herein comprises a heavy chain variable region comprising the following amino acid sequence:

```
                                      (SEQ ID NO: 12)
QVQLVQSGAEVKKPGASVKVSCKASGHIFSNYW1QWVRQAP

GQGLEWMGEXLPGSGHTEYTENFKDRVTMTRDTSTSTVYME

LSSLRSEDTAVYYCARYFFGSSPNWYFDVWGQGTLVTVSS.
```

In some embodiments, an anti-C5 antibody described herein comprises a light chain variable region comprising the following amino acid sequence:

```
                                       (SEQ ID NO: 8)
DIQMTQSPSSLSASVGDRVTITCGASEMIYGALNWYQQKPG

KAPKLLIYGATNLADGVPSRFSGSGSGTDFTLTISSLQPED

FATYYCQNVLNTPLTFGQGTKVEIK.
```

An anti-C5 antibody described herein can, in some embodiments, comprise a variant human Fc constant region that binds to human neonatal Fc receptor (FcRn) with greater affinity than that of the native human Fc constant region from which the variant human Fc constant region was derived. For example, the Fc constant region can comprise one or more (e.g., two, three, four, five, six, seven, or eight or more) amino acid substitutions relative to the native human Fc constant region from which the variant human Fc constant region was derived. The substitutions can increase the binding affinity of an IgG antibody containing the variant Fc constant region to FcRn at pH 6.0, while maintaining the pH dependence of the interaction. Methods for testing whether one or more substitutions in the Fc constant region of an antibody increase the affinity of the Fc constant region for FcRn at pH 6.0 (while maintaining pH dependence of the interaction) are known in the art and exemplified in the working examples (PCT/US2015/019225 and U.S. Pat. No. 9,079,949 the disclosures of each of which are incorporated herein by reference in their entirety).

Substitutions that enhance the binding affinity of an antibody Fc constant region for FcRn are known in the art and include, e.g., (1) the M252Y/S254T/T256E triple substitution described by Dall'Acqua, W. et al. (*J. Biol. Chem.*, 281:23514-24, 2006); (2) the M428L or T250Q/M428L substitutions described in Hinton, P. et al. (*J. Biol. Chem.*, 279:6213-6, 2004) and Hinton, P. et al. (*J. Immunol.*, 176: 346-56, 2006); and (3) the N434A or T307/E380A/N434A substitutions described in Petkova, S. et al. (*Int. Immunol.*, 18:1759-69, 2006). Additional substitution pairings: P257I/Q311I, P257I/N434H, and D376V/N434H have also been described (Datta-Mannan, A. et al., *J. Biol. Chem.*, 282: 1709-17, 2007, the disclosure of which is incorporated herein by reference in its entirety).

In some embodiments, the variant constant region has a substitution at EU amino acid residue 255 for valine. In some embodiments, the variant constant region has a substitution at EU amino acid residue 309 for asparagine. In some embodiments, the variant constant region has a substitution at EU amino acid residue 312 for isoleucine. In some embodiments, the variant constant region has a substitution at EU amino acid residue 386.

In some embodiments, the variant Fc constant region comprises no more than 30 (e.g., no more than 29, 28, 27, 26, 25, 24, 23, 22, 21, 20, 19, 18, 17, 16, 15, 14, 13, 12, 11, 10, nine, eight, seven, six, five, four, three, or two) amino acid substitutions, insertions, or deletions relative to the native constant region from which it was derived. In some embodiments, the variant Fc constant region comprises one or more amino acid substitutions selected from the group consisting of: M252Y, S254T, T256E, N434S, M428L, V259L, T250I, and V308F. In some embodiments, the variant human Fc constant region comprises a methionine at position 428 and an asparagine at position 434, each in EU numbering. In some embodiments, the variant Fc constant region comprises a 428L/434S double substitution as described in, e.g., U.S. Pat. No. 8,088,376.

In some embodiments the precise location of these mutations may be shifted from the native human Fc constant region position due to antibody engineering. The 428L/434S double substitution when used in a IgG2/4 chimeric Fc, for example, may correspond to 429L and 435S as in the M429L and N435S variants found in BNJ441 (ravulizumab) and described in U.S. Pat. No. 9,079,949, the disclosure of which is incorporated herein by reference in its entirety.

In some embodiments, the variant constant region comprises a substitution at amino acid position 237, 238, 239, 248, 250, 252, 254, 255, 256, 257, 258, 265, 270, 286, 289, 297, 298, 303, 305, 307, 308, 309, 311, 312, 314, 315, 317, 325, 332, 334, 360, 376, 380, 382, 384, 385, 386, 387, 389, 424, 428, 433, 434, or 436 (EU numbering) relative to the native human Fc constant region. In some embodiments, the substitution is selected from the group consisting of: methionine for glycine at position 237; alanine for proline at position 238; lysine for serine at position 239; isoleucine for lysine at position 248; alanine, phenylalanine, isoleucine, methionine, glutamine, serine, valine, tryptophan, or tyrosine for threonine at position 250; phenylalanine, tryptophan, or tyrosine for methionine at position 252; threonine for serine at position 254; glutamic acid for arginine at position 255; aspartic acid, glutamic acid, or glutamine for threonine at position 256; alanine, glycine, isoleucine, leucine, methionine, asparagine, serine, threonine, or valine for proline at position 257; histidine for glutamic acid at position 258; alanine for aspartic acid at position 265; phenylalanine for aspartic acid at position 270; alanine, or glutamic acid for asparagine at position 286; histidine for threonine at position 289; alanine for asparagine at position 297; glycine for serine at position 298; alanine for valine at position 303; alanine for valine at position 305; alanine, aspartic acid, phenylalanine, glycine, histidine, isoleucine, lysine, leucine, methionine, asparagine, proline, glutamine, arginine, serine, valine, tryptophan, or tyrosine for threonine at position 307; alanine, phenylalanine, isoleucine, leucine, methionine, proline, glutamine, or threonine for valine at position 308; alanine, aspartic acid, glutamic acid, proline, or arginine for leucine or valine at position 309; alanine, histidine, or isoleucine for glutamine at position 311; alanine or histidine for aspartic acid at position 312; lysine or arginine for leucine at position 314; alanine or histidine for asparagine at position 315; alanine for lysine at position 317; glycine for asparagine at position 325; valine for isoleucine at position 332; leucine for lysine at position 334; histidine for lysine at position 360; alanine for aspartic acid at position 376; alanine for glutamic acid at position 380; alanine for glutamic acid at position 382; alanine for asparagine or serine at position 384; aspartic acid or histidine for glycine at position 385; proline for glutamine at position 386; glutamic acid for proline at position 387; alanine or serine for asparagine at position 389; alanine for serine at position 424; alanine, aspartic acid, phenylalanine, glycine, histidine, isoleucine, lysine, leucine, asparagine, proline, glutamine, serine, threonine, valine, tryptophan, or tyrosine for methionine at position 428; lysine for histidine at position 433; alanine, phenylalanine, histidine, serine, tryptophan, or tyrosine for asparagine at position 434; and histidine for tyrosine or phenylalanine at position 436, all in EU numbering.

Suitable anti-C5 antibodies for use in the methods described herein, in some embodiments, comprise a heavy chain polypeptide comprising the amino acid sequence depicted in SEQ ID NO:14 and/or a light chain polypeptide comprising the amino acid sequence depicted in SEQ ID NO:11. Alternatively, the anti-C5 antibodies for use in the methods described herein, in some embodiments, comprise a heavy chain polypeptide comprising the amino acid sequence depicted in SEQ ID NO:20 and/or a light chain polypeptide comprising the amino acid sequence depicted in SEQ ID NO:11.

In one embodiment, the antibody binds to C5 at pH 7.4 and 25° C. (and, otherwise, under physiologic conditions) with an affinity dissociation constant (KD) that is at least 0.1 (e.g., at least 0.15, 0.175, 0.2, 0.25, 0.275, 0.3, 0.325, 0.35, 0.375, 0.4, 0.425, 0.45, 0.475, 0.5, 0.525, 0.55, 0.575, 0.6, 0.625, 0.65, 0.675, 0.7, 0.725, 0.75, 0.775, 0.8, 0.825, 0.85, 0.875, 0.9, 0.925, 0.95, or 0.975) nM. In some embodiments, the KD of the anti-C5 antibody, or antigen binding fragment thereof, is no greater than 1 nM (e.g., no greater than 0.9, 0.8, 0.7, 0.6, 0.5, 0.4, 0.3, or 0.2 nM).

In other embodiments, the $[(K_D$ of the antibody for C5 at pH 6.0 at 25° C.)/($K_D$ of the antibody for C5 at pH 7.4 at 25° C.)] is greater than 21 (e.g., greater than 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 350, 400, 450, 500, 600, 700, 800, 900, 1000, 1500, 2000, 2500, 3000, 3500, 4000, 4500, 5000, 5500, 6000, 6500, 7000, 7500, or 8000).

Methods for determining whether an antibody binds to a protein antigen and/or the affinity for an antibody to a protein antigen are known in the art. The binding of an antibody to a protein antigen, for example, can be detected and/or quantified using a variety of techniques such as, but not limited to, Western blot, dot blot, surface plasmon resonance (SPR) method (e.g., BIAcore system; Pharmacia Biosensor AB, Uppsala, Sweden and Piscataway, N.J.), or enzyme-linked immunosorbent assay (ELISA) (Benny K. C. Lo (2004) "Antibody Engineering: Methods and Protocols," Humana Press (ISBN: 1588290921); Johne, B. et al., J. Immunol. Meth., 160:191-8, 1993; Jönsson, U. et al., *Ann. Biol. Clin.*, 51:19-26, 1993; and Jönsson, U. et al., *Biotechniques*, 11:620-7, 1991). In addition, methods for measuring the affinity (e.g., dissociation and association constants) are set forth in the working examples.

As used herein, the term "$k_a$" refers to the rate constant for association of an antibody to an antigen. The term "$k_d$" refers to the rate constant for dissociation of an antibody from the antibody/antigen complex. And the term "$K_D$" refers to the equilibrium dissociation constant of an antibody-antigen interaction. The equilibrium dissociation constant is deduced from the ratio of the kinetic rate constants, $K_D = k_d/k_a$. Such determinations preferably are measured at 25° C. or 37° C. (see the working examples). The kinetics of antibody binding to human C5, for example, can be determined at pH 8.0, 7.4, 7.0, 6.5 and 6.0 via surface plasmon resonance (SPR) on a BIAcore 3000 instrument using an anti-Fc capture method to immobilize the antibody.

In one embodiment, the anti-C5 antibody, or antigen binding fragment thereof, blocks the generation or activity of the C5a and/or C5b active fragments of a C5 protein (e.g., a human C5 protein). Through this blocking effect, the antibodies inhibit, e.g., the pro-inflammatory effects of C5a and the generation of the C5b-9 membrane attack complex (MAC) at the surface of a cell.

Methods for determining whether a particular antibody described herein inhibits C5 cleavage are known in the art. Inhibition of human complement component C5 can reduce the cell-lysing ability of complement in a subject's body fluids. Such reductions of the cell-lysing ability of complement present in the body fluid(s) can be measured by methods known in the art such as, for example, by a conventional hemolytic assay such as the hemolysis assay described by Kabat and Mayer (eds.), "Experimental Immunochemistry, 2nd Edition," 135-240, Springfield, Ill., CC Thomas (1961), pages 135-139, or a conventional variation of that assay such as the chicken erythrocyte hemolysis method (Hillmen, P. et al., *N. Engl. J. Med.,* 350:552-9, 2004). Methods for determining whether a candidate compound inhibits the cleavage of human C5 into forms C5a and C5b are known in the art (Evans, M. et al., *Mol. Immunol.,* 32:1183-95, 1995). The concentration and/or physiologic activity of C5a and C5b in a body fluid can be measured, for example, by methods known in the art. For C5b, hemolytic assays or assays for soluble C5b-9 as discussed herein can be used. Other assays known in the art can also be used. Using assays of these or other suitable types, candidate agents capable of inhibiting human complement component C5 can be screened.

Immunological techniques such as, but not limited to, ELISA can be used to measure the protein concentration of C5 and/or its split products to determine the ability of an anti-C5 antibody, or antigen binding fragment thereof, to inhibit conversion of C5 into biologically active products. In some embodiments, C5a generation is measured. In some embodiments, C5b-9 neoepitope-specific antibodies are used to detect the formation of terminal complement.

In some embodiments, C5 activity, or inhibition thereof, is quantified using a CH50eq assay. The CH50eq assay is a method for measuring the total classical complement activity in serum. This test is a lytic assay, which uses antibody-sensitized erythrocytes as the activator of the classical complement pathway and various dilutions of the test serum to determine the amount required to give 50% lysis (CH50). The percent hemolysis can be determined, for example, using a spectrophotometer. The CH50eq assay provides an indirect measure of terminal complement complex (TCC) formation, since the TCC themselves are directly responsible for the hemolysis that is measured.

Inhibition as it pertains to terminal complement activity, for example, includes at least a 5% (e.g., at least a 6, 7, 8, 9, 10, 15, 20, 25, 30, 35, 40, 45, 50, 55 or 60%) decrease in the activity of terminal complement as compared to the effect of a control antibody (or antigen-binding fragment thereof) under similar conditions and at an equimolar concentration. Substantial inhibition, as used herein, refers to inhibition of a given activity (e.g., terminal complement activity) of at least 40% (e.g., at least 45, 50, 55, 60, 65, 70, 75, 80, 85, 90 or 95% or greater). In some embodiments, an anti-C5 antibody described herein contains one or more amino acid substitutions relative to the CDRs of eculizumab (i.e., SEQ ID NOs:1-6), yet retains at least 30% (e.g., at least 31, 32, 33, 34, 35, 36, 37, 38, 39, 40, 41, 42, 43, 44, 45, 46, 47, 48, 49, 50, 55, 60, 65, 70, 75, 80, 85, 90 or 95%) of the complement inhibitory activity of eculizumab.

An anti-C5 antibody described herein has a serum half-life in humans that is at least 20 days (e.g., at least 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 days). In another embodiment, the anti-C5 antibody described herein has a serum half-life in humans that is at least 40 days. In another embodiment, the anti-C5 antibody described herein has a serum half-life in humans that is approximately 43 days. In another embodiment, the anti-C5 antibody described herein has a serum half-life in humans that is between 39-48 days. Methods for measuring the serum half-life of an antibody are known in the art. In some embodiments, an anti-C5 antibody, or antigen binding fragment thereof, described herein has a serum half-life that is at least 20% (e.g., at least 30, 35, 40, 45, 50, 55, 60, 65, 70, 75, 80, 85, 90, 95, 100, 125, 150, 175, 200, 250, 300, 400 or 500%) greater than the serum half-life of eculizumab, e.g., as measured in one of the mouse model systems described in the working examples (e.g., the C5-deficient/NOD/scid mouse or hFcRn transgenic mouse model system).

In one embodiment, the antibody competes for binding with, and/or binds to the same epitope on C5 as, the antibodies described herein. The term "binds to the same epitope" with reference to two or more antibodies means that the antibodies bind to the same segment of amino acid residues, as determined by a given method. Techniques for determining whether antibodies bind to the "same epitope on C5" with the antibodies described herein include, for example, epitope mapping methods, such as, x-ray analyses of crystals of antigen:antibody complexes that provides atomic resolution of the epitope and hydrogen/deuterium exchange mass spectrometry (HDX-MS). Other methods monitor the binding of the antibody to peptide antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. Antibodies having the same VH and VL or the same CDR1, 2 and 3 sequences are expected to bind to the same epitope.

Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, can be determined using known competition experiments. In certain embodiments, an antibody competes with, and inhibits binding of another antibody to a target by at least 10%, 20%, 30%, 40%, 50%, 60%, 70%, 80%, 90% or 100%. The level of inhibition or competition may be different depending on which antibody is the "blocking antibody" (i.e., the cold antibody that is incubated first with the target). Competing antibodies bind to the same epitope, an overlapping epitope or to adjacent epitopes (e.g., as evidenced by steric hindrance).

Anti-C5 antibodies or antigen-binding fragments thereof described herein, used in the methods described herein, can be generated using a variety of art-recognized techniques. Monoclonal antibodies may be obtained by various techniques familiar to those skilled in the art. Briefly, spleen cells from an animal immunized with a desired antigen are immortalized, commonly by fusion with a myeloma cell (Kohler, G. & Milstein, C., *Eur. J. Immunol.,* 6:511-9, 1976). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences that encode a monoclonal antibody or a binding fragment thereof by screening a DNA library from human B cells (Huse, W. et al., *Science,* 246:1275-81, 1989).

Compositions

Pharmaceutical compositions comprising ravulizumab, either alone or in combination with prophylactic agents, therapeutic agents, and/or pharmaceutically acceptable carriers are provided. The pharmaceutical compositions comprising ravulizumab provided herein are for use in, but not limited to, diagnosing, detecting or monitoring a disorder, in preventing, treating, managing or ameliorating a disorder or one or more symptoms thereof, and/or in research. The formulation of pharmaceutical compositions, either alone or in combination with prophylactic agents, therapeutic agents, and/or pharmaceutically acceptable carriers, is known to one skilled in the art.

In one embodiment, the composition comprises an anti-C5 antibody comprising the CDR1, CDR2 and CDR3 domains in a heavy chain variable region having the sequence set forth in SEQ ID NO: 12, and the CDR1, CDR2 and CDR3 domains in a light chain variable region having the sequence set forth in SEQ ID NO:8. In another embodiment, the anti-C5 antibody comprises heavy and light chains having the sequences shown in SEQ ID NOs:14 and 11, respectively The compositions can be formulated as a pharmaceutical solution, e.g., for administration to a subject for the treatment or prevention of NMOSD. The pharmaceutical compositions generally include a pharmaceutically acceptable carrier. As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt, sugars, carbohydrates, polyols and/or tonicity modifiers.

The compositions can be formulated according to standard methods. Pharmaceutical formulation is a well-established art, and is further described in, e.g., Gennaro (2000) "Remington: The Science and Practice of Pharmacy," 20th Edition, Lippincott, Williams & Wilkins (ISBN: 0683306472); Ansel et al. (1999) "Pharmaceutical Dosage Forms and Drug Delivery Systems," 7th Edition, Lippincott Williams & Wilkins Publishers (ISBN: 0683305727); and Kibbe (2000) "Handbook of Pharmaceutical Excipients American Pharmaceutical Association," 3rd Edition (ISBN: 091733096X). In some embodiments, a composition can be formulated, for example, as a buffered solution at a suitable concentration and suitable for storage at 2-8° C. (e.g., 4° C.). In some embodiments, a composition can be formulated for storage at a temperature below 0° C. (e.g., –20° C. or –80° C.). In some embodiments, the composition can be formulated for storage for up to 2 years (e.g., one month, two months, three months, four months, five months, six months, seven months, eight months, nine months, 10 months, 11 months, 1 year, 1½ years, or 2 years) at 2-8° C. (e.g., 4° C.). Thus, in some embodiments, the compositions described herein are stable in storage for at least 1 year at 2-8° C. (e.g., 4° C.).

The pharmaceutical compositions can be in a variety of forms. These forms include, e.g., liquid, semi-solid and solid dosage forms, such as liquid solutions (e.g., injectable and infusible solutions), dispersions or suspensions, tablets, pills, powders, liposomes and suppositories. The preferred form depends, in part, on the intended mode of administration and therapeutic application. Compositions containing a composition intended for systemic or local delivery, for example, can be in the form of injectable or infusible solutions. The compositions can be formulated for administration by a parenteral mode (e.g., intravenous, subcutaneous, intraperitoneal, or intramuscular injection). "Parenteral administration," "administered parenterally," and other grammatically equivalent phrases, as used herein, refer to modes of administration other than enteral and topical administration, usually by injection, and include, without limitation, intravenous, intranasal, intraocular, pulmonary, intramuscular, intraarterial, intrathecal, intracapsular, intraorbital, intracardiac, intradermal, intrapulmonary, intraperitoneal, transtracheal, subcutaneous, subcuticular, intraarticular, subcapsular, subarachnoid, intraspinal, epidural, intracerebral, intracranial, intracarotid and intrasternal injection and infusion. In one embodiment, the antibodies are formulated for intravenous administration.

An exemplary, non-limiting range for a therapeutically or prophylactically effective amount of ravulizumab or other anti-C5 antibodies such as eculizumab, BNJ 421, 7086, 8110, SKY59 and H4H12166PP provided herein is 600-5000 mg, for example, 900-2000 mg. It is to be noted that dosage values may vary with the type and severity of the condition to be alleviated. It is to be further understood that for any particular subject, specific dosage regimens may be adjusted over time according to the individual need and the professional judgment of the person administering or supervising the administration of the compositions, and that dosage ranges set forth herein are exemplary only and are not intended to limit the scope or practice of the claimed methods.

Methods of Treating Neuromyelitis Optica

The disclosure provides methods of treating subjects suffering from NMOSD by administering an antibody that specifically binds C5. As used herein, the term "subject" and "patient" are interchangeable. In certain embodiments, subjects and/or patients are mammals, including, for example, primates, e.g., humans, rodents, lagomorphs, camelids, ungulates, canines and felines. In certain embodiments, the subjects or patients suffering from NMOSD described herein are humans.

NMOSD is characterized by a relapsing disease course, from which recovery may be poor due to the stepwise accumulation of significant neurologic disability. Neuromyelitis optica (NMO), also known as Devic's Disease, or Devic's Syndrome is part of NMOSD and is a rare, severe disabling autoimmune inflammatory disorder of the central nervous system (CNS) that predominately affects the optic nerves and spinal cord, often leading to blindness, mono/para/tetraplegia, and respiratory failure.

In some embodiments, NMO is characterized by NMO-IgG antibodies directed at aquaporin 4 (anti-AQP4). In some embodiments, a subset of NMO patients is anti-AQP4*. In another embodiment, a subset of NMO patients is anti-MOG⁺ (myelin oligodendrocyte glycoprotein).

In some embodiments, AQP4 autoantibodies are found in patients with NMO-like symptoms that do not fulfill the clinical requirements to be diagnosed NMO. In some embodiments, one of the requirements to be diagnosed with NMO are recurrent and simultaneous optic nerve and spinal cord inflammation.

In some embodiments NMOSD encompasses limited forms of Devic's disease, such as single or recurrent event of longitudinally extensive myelitis, and bilateral simultaneous or recurrent optic neuritis. In some embodiments, NMOSD encompasses Asian optic-spinal MS (OSMS), or AQP4⁺ OSMS. In some embodiments, NMOSD further encompasses longitudinally extensive myelitis or optic neuritis associated with systemic autoimmune disease, and optic neuritis or myelitis associated with lesions in specific brain areas such as the hypothalamus, periventricular nucleus, and brainstem.

In certain embodiments, treatment of NMOSD includes the amelioration or improvement of one or more symptoms associated with NMOSD. Symptoms associated with NMOSD include visual impairment, decreased visual acuity, visual field defects, loss of color vision, spinal cord dysfunction, muscle weakness, reduced sensation and loss of bladder or bowel control.

In other embodiments, treatment of NMOSD includes the improvement of a clinical marker for NMOSD progression. These markers include, for example, time to relapse, annualized relapse rate (ARR), expanded disability scale score (EDSS), modified Rankin scale (mRS), quality of life (ED-5D), Hauser ambulatory index (HAI), change in visual acuity using a Snellen chart and severity of relapse using the optic spinal impairment score (OSIS).

NMOSD relapse is evidenced by symptoms of NMOSD occurring in a subject where symptoms have previously been successfully ameliorated. Relapse is shown by the onset or worsening of symptoms associated with vision or sensation. Changes in vision that are associated with relapse of NMOSD include rapid onset of eye pain, blurring of vision, colors that do not seem right, missing field of vision, spots or dots in the field of vision, flashing or flickering lights in the field of vision, difficulty focusing, difficulty reading and feelings that the field of vision seems incorrect. Changes in sensation that are associated with relapse of NMOSD include pain, tingling, numbness, arm, leg or face seems to fall asleep, loss of sense of position in space, loss of sense in extremities, slight touching is painful, clothes or bed sheets cause pain, and subject not being able to detect injury to the subject. Annualized relapse rate (ARR) is the average number of relapses per year.

In certain embodiments, a subject treated for NMOSD has had three or more relapses in the 24-month period before ravulizumab is administered. In other embodiments, a subject treated for NMO has 2, 3, 4, 5, 6, 7, 8, 9, 10, 11, 12 or more relapses in the 24 month period before ravulizumab is administered. In certain embodiments, a subject treated for NMOSD has an ARR of 1.0 or greater in the 24-month period before ravulizumab is administered. In other embodiments, a subject treated for NMOSD has an ARR of at least 1.0, 1.2, 1.4, 1.6, 1.8, 2.0, 25, 3.0, 3.5, 4.0, 4.5, 5.0, 5.5, 6.0, 6.5, 7.0 or more in the 24-month period before ravulizumab is administered.

Disability can be assessed based on the EDSS scores comparing the change from baseline in the two treatment groups. The Kurtzke Expanded Disability Status Scale (EDSS) is a method of quantifying disability in multiple sclerosis. The EDSS replaced the previous Disability Status Scales used in Multiple Sclerosis (MS). The EDSS quantified disability in eight Functional Systems (FS) and allows neurologists to assign a Functional System Score (FSS) in each of these. The Functional Systems are pyramidal, cerebellar, brainstem, sensory, bowel and bladder, visual, cerebral and other. EDSS steps 1.0 to 4.5 refer to people with MS who are fully ambulatory. EDSS steps 5.0 to 9.5 are defined by the impairment of ambulation. Disability is also to be assessed based on the mRS score comparing the change from baseline in the two treatment groups. mRS score is assessed by the treating physician at the protocol specified time points.

In certain embodiments, a subject treated for NMOSD has an EDSS score of at least 1.0 in the 24-month period before ravulizumab is administered. In other embodiments, a sub-ject treated for NMOSD has an EDSS score of at least 1.0, 1.5, 2.0, 2.5, 3.0, 3.5, 4.0, 4.5, 5.0, 5.5, 6.0, 6.5, 7.0 or more in the 24-month period before ravulizumab is administered. In other embodiments, a subject treated for NMOSD has an EDSS score from 1.0 to 7.0 in the 24-month period before ravulizumab is administered. In certain embodiments, a subject treated for NMOSD has an HAI score of at least 2.0 in the 24-month period before ravulizumab is administered. In other embodiments, a subject treated for NMOSD has an HAI score of at least 0.0, 1.0, 2.0, 3.0, 4.0, 5.0, 6.0, 7.0, 8.0 or 9.0 in the 24-month period before ravulizumab is administered. In other embodiments, a subject treated for NMOSD has an HAI score from 0.0 to 8.0 in the 24-month period before ravulizumab is administered. In certain embodiments, a subject treated for NMOSD has an mRS score of at least 0.0 in the 24-month period before ravulizumab is administered. In other embodiments, a subject treated for NMOSD has an mRS score of at least 0.0, 1.0, 2.0, 3.0, 4.0, 5.0, or more in the 24-month period before ravulizumab is administered. In other embodiments, a subject treated for NMOSD has an mRS score from 0.0 to 2.5 in the 24-month period before ravulizumab is administered.

Quality of life (QOL) can be assessed by the patient self-assessment questionnaires EQ-5D and SF-36 at the protocol specified time points. A sample questionnaire for EQ-5D is shown in FIG. 5. The EUROQOL (EQ-5D) is a reliable and validated survey of health status in 5 areas: mobility, self-care, usual activities, pain/discomfort, and anxiety/depression, completed by the subject. Each area has 3 levels: level 1 (no problems), level 2 (some problems), and level 3 (extreme problems). The EQ-5D is administered at Day 1, Weeks 4, 8, 12, 24, 36, 48, 60, 72, 84, 96 and 104, or ET (Visits 2, 6, 8, 10, 16, 22, 28, 34, 40, 46, 52 and 56, or ET). A clinically meaningful improvement in a patient's EQ-5D is reflected as an increase in score after 26 weeks of treatment. A sample questionnaire for SF-36 is shown in FIG. 5.

Ambulatory function can be assessed, for example, by HAI scale. Visual acuity can be assessed, for example, using the Snellen chart. Severity of relapse can be assessed, for example, using the optic spinal impairment score (OSIS). OSIS scores are summarized in Table 1.

According to certain embodiments, subjects administered ravulizumab show an increased time interval between relapses of NMOSD. In certain embodiments, the subjects have a period before relapse of greater than 6 weeks. In other embodiments, the period before relapse is greater than 6, 12, 18, 24, 30, 36, 42, 48, 54, 60, 66, 72, 78, 84, 90, 96, 102 or more weeks. In other embodiments, the period before relapse is greater than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or more weeks. In other embodiments, the period before relapse is greater than 1, 2, 3, 4, 5, 6, 7, 8, 9, 10, or more years. In other embodiments, the period before relapse is between 6 and 52 weeks, 6 and 26 weeks, 6 and 10 weeks, 26 and 52 weeks, 1 and 2 years, 1 and 5 years, 5 and 10 years or a relapse does not occur during the lifetime of the subject. In other embodiments, the period before relapse is greater than 6, 12, 18, 24, 30, 36, 42, 48, 54, 60, 66, 72, 78, 84, 90, 96, 102 or more months.

According to certain embodiments, the course of treatment with ravulizumab lasts for 108 weeks. According to other embodiments, the course of treatment lasts for 26-52, 26-78, 26-120, 26-130, 26-156, 26-104, 26-130, 26-156, 26-182, 26-208 weeks or more. In other embodiments, the course of treatment lasts for greater than 26, 27, 28, 29, 30, 31, 32, 33, 34, 35, 36, 37, 38, 39, 40, 41, 42, 43, 44, 45, 46, 47, 48, 49, 50, 51, 52, 78, 104, 130, 156 or 182 weeks. According to other embodiments, the course of treatment lasts for greater than 1, 2, 3, 4, 5, 10, 15, 20, 25, 30, 35, 40, 45, 50, 55, 60, 65, 70, 75, 80 or more years. In certain embodiments, the course of treatment lasts for the remainder of the subject's life.

According to certain embodiments, during the course of treatment, one or more symptoms or scores associated with NMOSD improves during the course of treatment and is maintained at the improved level throughout treatment. EDSS can improve, for example, after 26 weeks of treatment with a therapeutic antibody that specifically binds C5 and then remain at the improved level for the duration of the treatment, which can be, for example, 52 weeks of treatment with a therapeutic antibody that specifically binds C5. One example of a therapeutic antibody that binds C5 is ravulizumab.

In certain embodiments, the first sign of improvement occurs by 26 weeks of treatment with a therapeutic antibody that specifically binds C5. According to other embodiments, the first sign of improvement occurs between weeks 1-26, 26-52, 52-78, 78-104, 104-130, 130-156, 156-182, or 182-208 of treatment with a therapeutic antibody that specifically binds C5. In other embodiments, the first sign of improvement occurs at week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 78, 104, 130, 156 or 182.

According to certain embodiments, the first sign of improvement is maintained for a number of weeks during treatment with a binding protein that specifically binds C5 such as ravulizumab. According to certain embodiments, this number of weeks is at least 26. According to other embodiments, this number of weeks is 1-26, 26-52, 52-78, 78-104, 104-130, 130-156, 156-182, or 182-208. In other embodiments, this number of weeks is at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 78, 104, 130, 156 or 182. According to certain embodiments, when the first sign of improvement is maintained, this means that the metric for treatment of NMOSD does not fall below the value of the first sign of improvement. The metric could continue to improve and this would still be defined as maintenance of the first sign of improvement.

In one embodiment, the anti-C5 antibody (e.g., ravulizumab) or antigen binding fragment thereof is administered once on Day 1 of the administration cycle, once on Day 15 of the administration cycle, and every eight weeks thereafter. In one embodiment, the anti-C5 antibody or antigen binding fragment thereof is administered every eight weeks after the administration cycle for an extension period up to two years (e.g., at a dose of 3000 mg, 3300 mg, or 3600 mg).

In another embodiment, the anti-C5 antibody (e.g., ravulizumab) or antigen binding fragment thereof is administered for one or more administration cycles. In one embodiment, the administration cycle is 26 weeks. In another embodiment, the treatment comprises at least 1, 2, 3, 4, 5, 6, 7, 8, 9, 10 or 11 cycles. In another embodiment, the treatment is continued for the lifetime of the human patient.

In another embodiment, a method of treating a human patient with NMOSD is provided, the method comprising administering to the patient during an administration cycle an effective amount of an anti-C5 antibody (e.g., ravulizumab) or antigen binding fragment thereof comprising CDR1, CDR2 and CDR3 heavy chain sequences as set forth in SEQ ID NOs:19, 18 and 3, respectively, and CDR1, CDR2 and CDR3 light chain sequences as set forth in SEQ ID NOs:4, 5 and 6, respectively, wherein the anti-C5 antibody or antigen binding fragment thereof is administered. (a) once on Day 1 of the administration cycle at a dose of: 2400 mg to a patient weighing ≥40 to <60 kg, 2700 mg to a patient weighing ≥60 to <100 kg, or 3000 mg to a patient weighing ≥100 kg; and (b) on Day 15 of the administration cycle and every eight weeks thereafter at a dose of 3000 mg to a patient weighing ≥40 to <60 kg, 3300 mg to a patient weighing ≥60 to <100 kg, or 3600 mg to a patient weighing ≥100 kg.

In another embodiment, a method of treating a human patient with NMOSD is provided, the method comprising administering to the patient during an administration cycle an effective amount of an anti-C5 antibody (e.g., ravulizumab) or antigen binding fragment thereof comprising CDR1, CDR2 and CDR3 heavy chain sequences as set forth in SEQ ID NOs:19, 18 and 3, respectively, CDR1, CDR2 and CDR3 light chain sequences as set forth in SEQ ID NOs:4, 5 and 6, respectively, and a variant human Fc constant region that binds to human neonatal Fc receptor (FcRn), wherein the variant human Fc CH3 constant region comprises Met-429-Leu and Asn-435-Ser substitutions at residues corresponding to methionine 428 and asparagine 434, each in EU numbering, wherein the anti-C5 antibody (e.g., ravulizumab) or antigen binding fragment thereof, is administered: (a) once on Day 1 of the administration cycle at a dose of: 2400 mg to a patient weighing ≥40 to <60 kg, 2700 mg to a patient weighing ≥60 to <100 kg, or 3000 mg to a patient weighing ≥100 kg; and (b) on Day 15 of the administration cycle and every eight weeks thereafter at a dose of 3000 mg to a patient weighing ≥40 to <60 kg, 3300 mg to a patient weighing ≥60 to <100 kg, or 3600 mg to a patient weighing ≥100 kg.

In another embodiment, the anti-C5 antibody (e.g., ravulizumab) or antigen binding fragment thereof is administered to a patient weighing ≥40 to <60 kg: (a) once on Day 1 of the administration cycle at a dose of 2400 mg; and (b) on Day 15 of the administration cycle and every eight weeks thereafter at a dose of 3000 mg.

In another embodiment, the anti-C5 antibody (e.g., ravulizumab) or antigen binding fragment thereof is administered to a patient weighing ≥60 to <100 kg: (a) once on Day 1 of the administration cycle at a dose of 2700 mg; and (b) on Day 15 of the administration cycle and every eight weeks thereafter at a dose of 3300 mg.

In another embodiment, the anti-C5 antibody (e.g., ravulizumab) or antigen binding fragment thereof is administered to a patient weighing ≥100 kg: (a) once on Day 1 of the administration cycle at a dose of 3000 mg; and (b) on Day 15 of the administration cycle and every eight weeks thereafter at a dose of 3600 mg.

In another embodiment, a patient switches from receiving one C5 inhibitor to a different C5 inhibitor during the course of treatment. Different anti-C5 antibodies can be administered during separate treatment periods. In one embodiment, for example, a method of treating a human patient having a complement-associated disorder (e.g., NMOSD, e.g., NMO) who is being treated with eculizumab is provided, the method comprising discontinuing treatment with eculizumab and switching the patient to treatment with an alternative complement inhibitor (e.g., ravulizumab). In another embodiment, a method of treating a human patient having a complement-associated disorder who is being treated with ravulizumab is provided, the method comprising discontinuing treatment with ravulizumab and switching the patient to treatment with an alternative complement inhibitor.

Exemplary alternative complement inhibitors include, but are not limited to antibodies, or antigen-binding fragments thereof, small molecules, polypeptides, polypeptide analogs, peptidomimetics, siRNA and aptamers. In one embodiment, the alternative complement inhibitor inhibits one or more of complement components C1, C2, C3, C4, C5, C6, C7, C8, C9, Factor D, Factor B, properdin, MBL, MASP-1, MASP-2, or biologically active fragments thereof. In another embodiment, the alternative complement inhibitor inhibits one or both of the generation of the anaphylatoxic activity associated with C5a and/or the assembly of the membrane attack complex associated with C5b. In another embodiment, the alternative complement inhibitor is selected from the group consisting of CR1, LEX-CR1, MCP, DAF, CD59, Factor H, cobra venom factor, FUT-175, compstatin, and K76 COOH.

In another embodiment, methods of treating a human patient having a complement-associated disorder who is being treated with eculizumab are provided, the method comprising discontinuing treatment with eculizumab and switching the patient to treatment with an alternative anti-C5 antibody. In another embodiment, a method of treating a human patient having a complement-associated disorder who is being treated with ravulizumab, the method comprising discontinuing treatment with ravulizumab and switching the patient to treatment with an alternative anti-C5 antibody.

Exemplary alternative anti-C5 antibodies included, but are not limited to, (i) eculizumab, (ii), an antibody or antigen binding fragment thereof comprising heavy chain CDR1, CDR2 and CDR3 domains comprising SEQ ID NOs:21, 22 and 23, respectively, and light chain CDR1, CDR2 and CDR3 domains comprising SEQ ID NOs:24, 25 and 26, respectively, (iii) an antibody or antigen binding fragment thereof comprising a heavy chain variable region comprising SEQ ID NO:27 and a light chain variable region comprising SEQ ID NO:28, (iv) an antibody or antigen binding fragment thereof comprising heavy chain CDR1, CDR2 and CDR3 domains comprising SEQ ID NOs:29, 30 and 31, respectively, and light chain CDR1, CDR2 and CDR3 domains comprising SEQ ID NOs:32, 33 and 34, respectively, (v) an antibody or antigen binding fragment thereof comprising a heavy chain variable region comprising SEQ ID NO:35 and a light chain variable region comprising SEQ ID NO:36, (vi) an antibody or antigen binding fragment thereof comprising heavy chain CDR1, CDR2 and CDR3 domains comprising SEQ ID NOs:37, 38 and 39, respectively, and light chain CDR1, CDR2 and CDR3 domains comprising SEQ ID NOs:40, 41 and 42, respectively, (vii) an antibody or antigen binding fragment thereof comprising a heavy chain variable region comprising SEQ ID NO:43 and a light chain variable region comprising SEQ ID NO:44, and (viii) an antibody or antigen binding fragment thereof comprising a heavy chain comprising SEQ ID NO:45 and a light chain comprising SEQ ID NO:46.

In another embodiment, the patient is treated with ravulizumab and then switched to treatment with the 7086 antibody, the 8110 antibody, the 305LO5 antibody, the SKY59 antibody, the H4H12166PP antibody or eculizumab. In another embodiment, the patient is switched from an anti-C5 antibody (e.g., eculizumab, the 7086 antibody, the 8110 antibody, the 305LO5 antibody, the SKY59 antibody, or the H4H12166PP antibody) to another anti-C5 antibody (e.g., ravulizumab) during the course of treatment. In a particular embodiment, the patient is switched from eculizumab to ravulizumab during the course of treatment.

In another aspect, the treatment regimens described are sufficient to maintain particular serum trough concentrations of the anti-C5 antibody or antigen binding fragment thereof. In one embodiment, for example, the treatment maintains a serum trough concentration of the anti-C5 antibody or antigen binding fragment thereof of 50, 55, 60, 65, 70, 75, 80, 85, 90, 95, 100, 105, 110, 115, 120, 125, 130, 135, 140, 145, 150, 155, 160, 165, 170, 175, 180, 185, 190, 200, 205, 210, 215, 220, 225, 230, 240, 245, 250, 255, 260, 265, 270, 280, 290, 300, 305, 310, 315, 320, 325, 330, 335, 340, 345, 350, 355, 360, 365, 370, 375, 380, 385, 390, 395 or 400 µg/mL or greater. In one embodiment, the treatment maintains a serum trough concentration of the anti-C5 antibody or antigen binding fragment thereof of 100 µg/mL or greater. In another embodiment, the treatment maintains a serum trough concentration of the anti-C5 antibody or antigen binding fragment thereof, of 150 µg/mL or greater. In another embodiment, the treatment maintains a serum trough concentration of the anti-C5 antibody or antigen binding fragment thereof of 200 µg/mL or greater. In another embodiment, the treatment maintains a serum trough concentration of the anti-C5 antibody or antigen binding fragment thereof of 250 µg/mL or greater. In another embodiment, the treatment maintains a serum trough concentration of the anti-C5 antibody or antigen binding fragment thereof of 300 µg/mL or greater. In another embodiment, the treatment maintains a serum trough concentration of the anti-C5 antibody or antigen binding fragment thereof of between 100 µg/mL and 200 µg/mL. In another embodiment, the treatment maintains a serum trough concentration of the anti-C5 antibody or antigen binding fragment thereof of about 175 µg/mL.

In another embodiment, to obtain an effective response, the anti-C5 antibody is administered to the patient in an amount and with a frequency to maintain at least 50 µg, 55 µg, 60 µg, 65 µg, 70 µg, 75 µg, 80 µg 85 µg, 90 µg, 95 µg, 100 µg, 105 µg, 110 µg, 115 µg, 120 µg, 125 µg, 130 µg, 135 µg, 140 µg, 145 µg, 150 µg, 155 µg, 160 µg, 165 µg, 170 µg, 175 µg, 180 µg, 185 µg, 190 µg, 195 µg, 200 µg, 205 µg, 210 µg, 215 µg, 220 µg, 225 µg, 230 µg, 235 µg, 240 µg, 245 µg, 250 µg, 255 µg, or 260 µg of antibody per milliliter of the patient's blood. In another embodiment, the anti-C5 antibody is administered to the patient in an amount and with a frequency to maintain between 50 µg and 250 µg of antibody per milliliter of the patient's blood. In another embodiment, the anti-C5 antibody is administered to the patient in an amount and with a frequency to maintain between 100 µg and 200 µg of antibody per milliliter of the patient's blood. In another embodiment, the anti-C5 antibody is administered to the patient in an amount and with a frequency to maintain about 175 µg of antibody per milliliter of the patient's blood.

In one embodiment, the anti-C5 antibody is administered (or is for administration) according to a particular clinical dosage regimen (e.g., at a particular dose amount and/or according to a specific dosing schedule).

In another embodiment, the dose of the anti-C5 antibody is based on the weight of the patient. In one embodiment, 10 mg, 20 mg, 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1100 mg, 1200 mg, 1300 mg, 1400 mg, 1500 mg, 1600 mg, 1700 mg, 1800 mg, 1900 mg, 2000 mg, 2100 mg, 2200 mg, 2300 mg, 2400 mg, 2500 mg, 2600 mg, 2700 mg, 2800 mg, 2900 mg, 3000 mg, 3100 mg, 3200 mg, 3300 mg, 3400 mg, 3500 mg, 3600 mg, 3700 mg, 3800 mg, 3900 mg, 4000 mg, 4100 mg, 4200 mg, 4300 mg, 4400 mg, 4500 mg, 4600 mg, 4700 mg, 4800 mg, 4900 mg, 5000 mg, 5100 mg, 5200 mg, 5300 mg, 5400 mg, 5500 mg, 5600 mg, 5700 mg, 5800 mg, 5900 mg, 6000 mg, 6100 mg, 6200 mg, 6300 mg, 6400 mg, 6500 mg, 6600 mg, 6700 mg, 6800 mg, 6900 mg, 7000 mg, 7100 mg, 7200 mg, 7300 mg, 7400 mg, 7500 mg, 7600 mg, 7700 mg, 7800 mg, 7900 mg, 8000 mg, 8100 mg, 8200 mg, 8300 mg, 8400 mg, 8500 mg, 8600 mg, 8700 mg, 8800 mg, 8900 mg, 9000 mg, 9100 mg, 9200 mg, 9300 mg, 9400 mg, 9500 mg, 9600 mg, 9700 mg, 9800 mg, 9900 mg, 10000 mg, 10100 mg, 10200 mg, 10300 mg, 10400 mg, 10500 mg, 10600 mg, 10700 mg, 10800 mg, 10900 mg, or 11000 mg of the anti-C5 antibody or antigen binding fragment thereof is administered to a patient weighing ≥40 to <60 kg.

In another embodiment, 10 mg, 20 mg, 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1100 mg, 1200 mg, 1300 mg, 1400 mg, 1500 mg, 1600 mg, 1700 mg, 1800 mg, 1900 mg, 2000 mg, 2100 mg, 2200 mg, 2300 mg, 2400 mg, 2500 mg, 2600 mg, 2700 mg, 2800 mg, 2900 mg, 3000 mg, 3100 mg, 3200 mg, 3300 mg, 3400 mg, 3500 mg, 3600 mg, 3700 mg, 3800 mg, 3900 mg, 4000 mg, 4100 mg, 4200 mg, 4300 mg, 4400 mg, 4500 mg, 4600 mg, 4700 mg, 4800 mg, 4900 mg, 5000 mg, 5100 mg, 5200 mg, 5300 mg, 5400 mg, 5500 mg, 5600 mg, 5700 mg, 5800 mg, 5900 mg, 6000 mg, 6100 mg, 6200 mg, 6300 mg, 6400 mg, 6500 mg, 6600 mg, 6700 mg, 6800 mg, 6900 mg, 7000 mg, 7100 mg, 7200 mg, 7300 mg, 7400 mg, 7500 mg, 7600 mg, 7700 mg, 7800 mg, 7900 mg, 8000 mg, 8100 mg, 8200 mg, 8300 mg, 8400 mg, 8500 mg, 8600 mg, 8700 mg, 8800 mg, 8900 mg, 9000 mg, 9100 mg, 9200 mg, 9300 mg, 9400 mg, 9500 mg, 9600 mg, 9700 mg, 9800 mg, 9900 mg, 10000 mg, 10100 mg, 10200 mg, 10300 mg, 10400 mg, 10500 mg, 10600 mg, 10700 mg, 10800 mg, 10900 mg, or 11000 mg of the anti-C5 antibody or antigen binding fragment thereof is administered to a patient weighing ≥60 to <100 kg.

In another embodiment, 10 mg, 20 mg, 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1100 mg, 1200 mg, 1300 mg, 1400 mg, 1500 mg, 1600 mg, 1700 mg, 1800 mg, 1900 mg, 2000 mg, 2100 mg, 2200 mg, 2300 mg, 2400 mg, 2500 mg, 2600 mg, 2700 mg, 2800 mg, 2900 mg, 3000 mg, 3100 mg, 3200 mg, 3300 mg, 3400 mg, 3500 mg, 3600 mg, 3700 mg, 3800 mg, 3900 mg, 4000 mg, 4100 mg, 4200 mg, 4300 mg, 4400 mg, 4500 mg, 4600 mg, 4700 mg, 4800 mg, 4900 mg, 5000 mg, 5100 mg, 5200 mg, 5300 mg, 5400 mg, 5500 mg, 5600 mg, 5700 mg, 5800 mg, 5900 mg, 6000 mg, 6100 mg, 6200 mg, 6300 mg, 6400 mg, 6500 mg, 6600 mg, 6700 mg, 6800 mg, 6900 mg, 7000 mg, 7100 mg, 7200 mg, 7300 mg, 7400 mg, 7500 mg, 7600 mg, 7700 mg, 7800 mg, 7900 mg, 8000 mg, 8100 mg, 8200 mg, 8300 mg, 8400 mg, 8500 mg, 8600 mg, 8700 mg, 8800 mg, 8900 mg, 9000 mg, 9100 mg, 9200 mg, 9300 mg, 9400 mg, 9500 mg, 9600 mg, 9700 mg, 9800 mg, 9900 mg, 10000 mg, 10100 mg, 10200 mg, 10300 mg, 10400 mg, 10500 mg, 10600 mg, 10700 mg, 10800 mg, 10900 mg, or 11000 mg is administered to a patient weighing ≥100 kg. In certain embodiments, dosage regimens are adjusted to provide the optimum desired response (e.g., an effective response).

In another embodiment, the anti-C5 antibody is administered at a milligram per kilogram (mg/kg) dose. For example, in one embodiment, the anti-C5 antibody or antigen binding fragment thereof is administered at a dose of 0.1 mg/kg, 0.25 mg/kg, 0.5 mg/kg, 0.75 mg/kg, 1.0 mg/kg, 1.25 mg/kg, 1.50 mg/kg, 1.75 mg/kg, 2.0 mg/kg, 2.25 mg/kg, 2.50 mg/kg, 2.75 mg/kg, 3.0 mg/kg, 3.25 mg/kg, 3.50 mg/kg, 3.75 mg/kg, 4.0 mg/kg, 4.25 mg/kg, 4.50 mg/kg, 4.75 mg/kg, 5.0 mg/kg, 5.25 mg/kg, 5.50 mg/kg, 5.75 mg/kg, 6.0 mg/kg, 6.25 mg/kg, 6.50 mg/kg, 6.75 mg/kg, 7.0 mg/kg, 7.25 mg/kg, 7.50 mg/kg, 7.75 mg/kg, 8.0 mg/kg, 8.25 mg/kg, 8.50 mg/kg, 8.75 mg/kg, 9.0 mg/kg, 9.25 mg/kg, 9.50 mg/kg, 9.75 mg/kg, 10.0 mg/kg, 11.25 mg/kg, 11.50 mg/kg, 11.75 mg/kg, 12.0 mg/kg, 12.25 mg/kg, 12.50 mg/kg, 12.75 mg/kg, 13.0 mg/kg, 13.25 mg/kg, 13.50 mg/kg, 13.75 mg/kg, 14.0 mg/kg, 14.25 mg/kg, 14.50 mg/kg, 14.75 mg/kg, 15.0 mg/kg, 15.25 mg/kg, 15.50 mg/kg, 15.75 mg/kg, 16.0 mg/kg, 16.25 mg/kg, 16.50 mg/kg, 16.75 mg/kg, 17.0 mg/kg, 17.25 mg/kg, 17.50 mg/kg, 17.75 mg/kg, 18.0 mg/kg, 18.25 mg/kg, 18.50 mg/kg, 18.75 mg/kg, 19.0 mg/kg, 19.25 mg/kg, 19.50 mg/kg, 19.75 mg/kg, 20.0 mg/kg, 20.25 mg/kg, 20.50 mg/kg, 20.75 mg/kg, 21.0 mg/kg, 21.25 mg/kg, 21.50 mg/kg, 21.75 mg/kg, 22.0 mg/kg, 22.25 mg/kg, 22.50 mg/kg, 22.75 mg/kg, 23.0 mg/kg, 23.25 mg/kg, 23.50 mg/kg, 23.75 mg/kg, 24.0 mg/kg, 24.25 mg/kg, 24.50 mg/kg, 24.75 mg/kg or 25.0 mg/kg.

In one embodiment, the anti-C5 antibody is administered once per week, twice per week, three times per week, four times per week, five times per week, six times per week, or daily. In another embodiment, the anti-C5 antibody is administered twice daily. In another embodiment, the anti-C5 antibody is administered once every two weeks, once every three weeks, once every four weeks, once every five weeks, once every six weeks, once every seven weeks, once every eight weeks, once every nine weeks, once every ten weeks, once every eleven weeks, or once every twelve weeks. In another embodiment, the anti-C5 antibody is administered at a loading dose on Day 1, followed by a different maintenance dose on Day 15 and every eight weeks thereafter.

In another embodiment, to obtain an effective response, the anti-C5 antibody is administered to the patient in an amount and with a frequency to maintain a minimum free C5 concentration. In one embodiment, the anti-C5 antibody is administered to the patient in an amount and with a frequency to maintain a free C5 concentration of 0.2 μg/mL, 0.3 μg/mL, 0.4 μg/mL, 0.5 μg/mL or less. In another embodiment, the anti-C5 antibody is administered to the patient in an amount and with a frequency to maintain a free C5 concentration of 0.309 to 0.5 μg/mL or less.

In some embodiments, the patients treated according to the methods described herein have been vaccinated against meningococcal infections within three years prior to, or at the time of, initiating study drug. In one embodiment, patients who initiate treatment less than two weeks after receiving a meningococcal vaccine receive treatment with appropriate prophylactic antibiotics until two weeks after vaccination. In another embodiment, patients treated according to the methods described herein are vaccinated against meningococcal serotypes A, C, Y, W135, and/or B.

In accordance with the present disclosure there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. 1. Freshney, ed. (1986)]; Immobilized Cells And Enzymes [IRL Press, (1986)]; B. Perbal, A Practical Guide To Molecular Cloning (1984); F. M. Ausubel et al. (eds.), Current Protocols in Molecular Biology, John Wiley & Sons, Inc. (1994). Each of these references is incorporated by reference herein in its entirety.

Unless otherwise stated, sequence identity/similarity values provided herein refer to the value obtained using the BLAST 2.0 suite of programs using default parameters (Altschul, S. et al., *Nucleic Acids Res.,* 25:3389-402, 1997), incorporated by reference herein in its entirety).

As used herein, "sequence identity" or "identity" in the context of two polypeptide sequences includes reference to the residues in the two sequences, which are the same when aligned for maximum correspondence over a specified comparison window. When percentage of sequence identity is used in reference to proteins, it is recognized that residue positions that are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are known to those of skill in the art (typically this involves scoring a conservative substitution as a partial rather than a full mismatch, thereby increasing the percentage sequence identity). Thus, for example, where an identical amino acid is given a score of one and a non-conservative substitution is given a score of zero, a conservative substitution is given a score between zero and one. The scoring of conservative substitutions is calculated, e.g., according to the algorithm of Meyers, E. and Miller, W. (*Compute. Appl. Biosci.,* 4:11-7, 1988), e.g., as implemented in the program PC/GENE (Intelligenetics, Mountain View, Calif., USA). Each of these references are incorporated by reference herein in its entirety.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" or "substantially identical" in the context of polynucleotide sequences means that a polynucleotide comprises a sequence that has between 50-100% sequence identity, e.g., at least 50% sequence identity, at least 60% sequence identity, at least 70%, at least 80%, at least 90% or at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, e.g., at least 55%, at least 60%, at least 70%, at least 80%, at least 90% or at least 95%.

EXAMPLES

Example 1. Effectiveness and Safety of Ravulizumab in Treating Neuromyelitis Optica Spectrum Disorder (NMOSD) in Adult Patients 1. Study Design
1.1. Overall Design
This is a Phase 3, external placebo-controlled, open-label, multicenter study to evaluate the efficacy and safety of ravulizumab in adult patients with NMOSD. Approximately 55 eligible adult patients with NMOSD from North America, Europe, Asia Pacific and Japan are enrolled into the study.

There are 4 periods in this study: Screening Period, Primary Treatment Period, Long-Term Extension Period, and Safety Follow-up Period (FIG. 1). Patients are screened for eligibility for up to 6 weeks during the Screening Period. The Primary Treatment Period ends and the Long-Term Extension Period starts when all patients have completed the Week 26 Visit or discontinued early, and then completed their End of Primary Treatment (EOPT) visit. All patients continue to receive ravulizumab during the Long-Term Extension Period for up to 2 years, or until ravulizumab is approved and/or available (in accordance with country-specific regulations), whichever occurs first. Based on the estimated enrollment rate of NMOSD patients, the total treatment duration for each patient is up to 4 years. After the last dose of study drug or early discontinuation (ED), patients are followed for 8 weeks.

When eligible patients enroll into the study, they receive intravenous infusions of ravulizumab. The ravulizumab dose for each patient is based on body weight. The dosing regimen consists of a loading dose followed by maintenance dosing administered every 8 weeks (q8w). The maintenance dosing should be initiated 2 weeks after the loading dose administration.

For each patient, the total duration of study participation is up to 4 years and 14 weeks, including the Screening Period (up to 6 weeks), the Primary Treatment Period (between 26 weeks and 2 years), the Long-Term Extension Period (up to 2 years), and the Safety Follow-up Period (8 weeks).
1.2. Scientific Rationale for Study Design
The study has been designed to provide data that adequately characterize the benefit-risk profile of ravulizumab for the treatment of patients with NMOSD, using placebo data from another study looking at the use of eculizumab for the treatment of NMOSD as an external control.

A single-arm design, utilizing the placebo group from Study NCT01892345 (conducted 2014 to 2018) as an external placebo control, allows for a robust assessment of ravulizumab as a treatment option for NMOSD. Whenever possible, to ensure a valid comparison, constancy is maintained with Study NCT01892345, including the inclusion of similar patient populations, permits concomitant medications, adjudication procedures, and endpoints.

1.2.1. Rationale for the Selected Endpoints 1.2.1.1. Efficacy Endpoints

In NMOSD, the measurable, biological aspects include relapse and disability. Disability in NMOSD is a direct consequence of relapse, supporting the relevance of measuring relapses as the efficacy endpoint.

In this study, the occurrence of relapses is evaluated using the primary endpoint TFR and the secondary endpoint ARR. Time to first relapse provides useful information regarding the efficacy of ravulizumab. Since effectiveness of a treatment can be based on delaying and/or reducing the occurrence of relapses, TFR is an appropriate efficacy endpoint for prospectively designed studies in NMOSD. The external placebo group from Study NCT01892345 is utilized as an appropriate control group given that the primary endpoint in that trial is also TFR and the adjudication process and relapse definition will remain constant between the two trials. Additionally, the effect of ravulizumab on the frequency of relapses is measured using the Adjudicated On-Trial ARR. A 95% confidence interval will be calculated around the ARR. The objectives and endpoints of this study is summarized in Table 1 below.

| Objectives and Endpoints | |
| --- | --- |
| Objectives | Endpoints |
| Primary | |
| To evaluate the effect of ravulizumab on adjudicated On-Trial[a] Relapses in adult patients with NMOSD | Time to first adjudicated On-Trial Relapse and relapse risk reduction |
| Secondary | |
| To evaluate the safety of ravulizumab in adult patients with NMOSD | Incidence of treatment-emergent adverse events (TBAEs), Treatment-emergent serious adverse events (TESAEs), and TEAEs leading to study drug discontinuation |
| To evaluate the effect of ravulizumab on adjudicated annualized relapse rate (ARR) in adult patients with NMOSD | Adjudicated On-Trial ARR |
| To evaluate the effect of ravulizumab on disease-related disability in adult patients with NMOSD | Clinically important worsening in expanded disability status scale (EDSS) |
| To evaluate the effect of ravulizumab on quality of life (QoL) in adult patients with NMOSD | Change from baseline in EuroQoL-5D (EQ-5D) |
| To evaluate the effect of ravulizumab on neurologic function in adult patients with NMOSD | Clinically important change in Hauser ambulation index (HAI) |
| To characterize the pharmacokinetics (PK) of ravulizumab in adult patients with NMOSD | Change in serum ravulizumab concentration over the study duration |
| To characterize the pharmacodynamics (PD) of ravulizumab in adult patients with NMOSD | Change in serum free C5 concentration over the study duration |
| To characterize the immunogenicity of ravulizumab in adult patients with NMOSD | Presence and titer of anti-drug antibodies (ADAs) over the study duration |
| Exploratory | |
| To evaluate the effect of ravulizumab on severity of adjudicated relapse in adult patients with NMOSD | Change from baseline in Optic Spinal Impairment Score (OSIS) |
| To evaluate the effect of ravulizumab on neurologic function in adult patients with NMOSD | Characterize the change in visual acuity, color vision, and confrontational visual fields |
| To evaluate the effect of ravulizumab on QoL in adult patients with NMOSD | Change from baseline in Short Form Health Survey (SF-36) |
| To evaluate the safety of ravulizumab in adult patients with NMOSD | Change from baseline in vital signs, electrocardiogram (ECG) parameters, and clinical laboratory assessments Shifts from Baseline in Columbia-suicide severity rating scale (C-SSRS) |
| To characterize biomarkers in adult patients with NMOSD | Change from baseline in levels of biomarkers of complement deregulation, neuroinflammation and neural injury Blood and cerebrospinal fluid (CSF) NMO-Ig (AQP4 Ab) concentration |

[a]On-Trial Relapses refer to relapses as determined by the Treating Physician that occur during the study treatment period. All relapses will be adjudicated by a separate Adjudication Committee.

1.2.2. Rationale for the Duration of the Primary Treatment Period

In this study, the Primary Treatment Period ends when all patients complete the Week 26 Visit or discontinue early. The expectation is that at that time, based on the estimated enrollment rate, the first patient enrolled will have been on-treatment for approximately 2 years, with the remaining patients having a time on treatment ranging between 26 weeks and 2 years (inclusive).

The cut-off of 26 weeks for the last patient is chosen for several reasons. In previous studies on eculizumab, key observations were able to be made by that time: 2 of the 3 adjudicated On-Trial Relapses observed in the eculizumab group are observed, and 12 of 20 adjudicated On-Trial Relapses have been observed in the placebo group. This design ensures that there will be limited number of patients censored during the first 26 weeks in the analysis of the time to first adjudicated On-Trial Relapse. It is also recognized that based on expected enrollment timelines, many of the patients will have been on treatment for more than 1 year by the time the last patient completes their Week 26 Visit, providing efficacy and safety data over time that allows for a robust comparison with data collected over a similar timeframe in the placebo group of Study NCT01892345.

1.2.3. Rationale for the Selected Patient Population

Complement activation is a major determinant of disease pathogenesis in patients with anti-AQP4 positive NMOSD. Inhibiting terminal complement activation with ravulizumab, therefore, represents a biologically rational approach for the treatment of patients with anti-AQP4 positive NMOSD. Study entry criteria are carefully selected to reflect an adult patient population consistent with the anti-AQP4 positive NMOSD population likely to be treated with ravulizumab in clinical practice.

1.3. Justification for Dose 1.3.1. Ravulizumab

Targeting complete terminal complement inhibition as a therapeutic strategy in the treatment of patients with NMOSD has been validated by data from the eculizumab clinical program. The dosing regimen of ravulizumab is designed to target immediate, complete, and sustained inhibition of terminal complement in patients. The weight-based doses of ravulizumab in a previous PNH program are premised on PK/PD data from early and late clinical development studies in healthy adult volunteers and patients with PNH. The proposed ravulizumab dosage regimen (Section 3.1; Section 5.1.6.1) is the approved regimen for the treatment of patients with PNH Ultomiris@ United States Prescribing Information (USPI), and the same dose regimen is also included in the initial marketing authorization application (MAA) in the EU. Therefore, the same dosage regimen is selected for this study.

1.3.2. Supplemental Dose

Supplemental doses of ravulizumab (Section 5.1.6.2) may be administered to patients who receive plasma exchange (PE)/plasmapheresis (PP) as acute therapy following an On-Trial Relapse (Section 3.5.1.3). The supplemental dose of ravulizumab has been selected based on PK simulations. Consistent with approved eculizumab labeling for treating adult and pediatric patients with aHUS, adult patients with generalized myasthenia gravis (gMG) and adult patients with NMOSD, supplemental dosing of ravulizumab in the amount of 50% (rounded up if not an integral of 300 mg due to vial configuration) are given in the setting of concomitant PP/PE therapy.

1.4. End of Primary Treatment

After all patients have completed the Week 26 Visit or discontinued early, patients return for an End of Primary Treatment (EOPT) Visit within 14 days:
  If the EOPT Visit coincides with an upcoming scheduled study visit, patients are required to complete all assessments for the EOPT Visit and can also be administered their scheduled dose of ravulizumab.
  If a patient is in the relapse evaluation period for their first relapse (defined as the first relapse after Day 1), the Week-6 Relapse Evaluation Visit is the patient's EOPT Visit.

The end of the Primary Treatment Period is defined as the date when all patients completed the Week 26 Visit or discontinue early, and then completed the EOPT Visit.

1.5. End of Study Definition

A patient is considered to have completed the study by satisfying either one of the following conditions:
  The patient completes all phases of the study including the last visit shown in the Schedule of Activities.
  The patient completes the study early because ravulizumab becomes registered or approved.

The end of the study is defined as the date of the last visit of the last patient (FIG. 2) in the trial globally.

2. Study Population

Prospective approval of protocol deviations to recruitment and enrollment criteria, also known as protocol waivers or exemptions, is not permitted.

2.1. Inclusion Criteria

Participants are eligible to be included in the study only if all of criteria from 2.2.1. to 2.2.5. applies.

2.1.1. Age

Patient must be 18 years of age or older, at the time of signing the informed consent.

2.1.2. Type of Patient and Disease Characteristics

The patient and disease characteristics for inclusion is as follow:
  Anti-AQP4 Ab-positive and a diagnosis of NMOSD as defined by the 2015 international consensus diagnostic criteria (Wingerchuk, D. et al., *Neurology.* 85:177-89, 2015). An historically positive anti-AQP4 Ab test may be acceptable if the test has been performed using an acceptable, validated cell-based assay from an accredited laboratory. In this setting, the historical test result and related information need to be reviewed and approved by the Sponsor's Medical Monitor prior to initiating study treatment.
  At least 1 attack or relapse in the last 12 months prior to the Screening Period (NOTE: Patients with a single life-time attack is considered to satisfy this inclusion criterion if the attack occurs in the last 12 months.)
  Expanded Disability Status Scale (EDSS) score ≤7
  Patients who enter the trial receiving supportive IST (e.g., corticosteroids, azathioprine [AZA], mycophenolate mofetil [MMF], methotrexate [MTX], and tacrolimus [TAC]) for the prevention of relapse, either in combination or monotherapy, must be on a stable dosing regimen of adequate duration prior to Screening with no plan to change the dose during the study period as follows:
    a. If patients who enter the study are receiving AZA, they must have been on AZA for no less than 6 months and have been on a stable dose for more than 2 months prior to Screening.
    b. If patients who enter the study are receiving other ISTs (e.g., MMF, MTX, or TAC), they must have been on the IST for no less than 3 months and have been on a stable dose for more than 4 weeks prior to Screening.

c. If patients who enter the study are receiving oral corticosteroids, they must have been on a stable dose for more than 4 weeks prior to Screening.

d. If a patient enters the trial receiving oral corticosteroid(s) with or without other IST(s), the daily corticosteroid dose must be no more than prednisone 20 mg/day (or equivalent) prior to Screening.

Vaccinated against *N. meningitidis* within 3 years prior to, or at the time of, initiating ravulizumab. Patients who initiate study drug treatment less than 2 weeks after receiving a meningococcal vaccine must receive appropriate prophylactic antibiotics until 2 weeks after the vaccination.

2.1.3. Weight

Body weight is no less than 40 kg.

2.1.4. Sex

For male or female, contraceptive use by men or women should be consistent with local regulations regarding the methods of contraception for those participating in clinical studies. Male patients must agree to use contraception during the treatment period and for at least eight months after last dose of study drug and refrain from donating sperm during this period.

A female patient is eligible to participate if she is not pregnant, not breastfeeding, and at least one of the following conditions applied:

Not a woman of childbearing potential (WOCBP), or

Is a WOCBP and using a highly effective or acceptable contraceptive method during the treatment period and for at a minimum of eight months after the last dose of study drug.

The investigator evaluates the effectiveness of the contraceptive method in relationship to the first dose of study drug. A WOCBP must have a negative highly sensitive pregnancy test (serum pregnancy test) within 24 hours before the first dose of study drug. The investigator is responsible for review of medical history, menstrual history, and recent sexual activity to decrease the risk for inclusion of a woman with an early undetected pregnancy.

2.1.5. Informed Consent

Capable of giving signed informed consent that includes compliance with the requirements and restrictions listed in the informed consent form (ICF) and in this protocol.

2.2. Exclusion Criteria

Patients are excluded from the study if any of the criteria from 2.2.1. to 2.2.4 applies.

2.2.1. Medical Conditions

History of *N. meningitidis* infection.

Human immunodeficiency virus (HIV) infection (evidenced by HIV-1 or HIV-2 antibody titer)

History of unexplained infections

Active systemic bacterial, viral, or fungal infection within 14 days prior to study drug administration on Day 1

Presence of fever not lower than 38° C. (100.4° F.) within 7 days prior to study drug administration on Day 1

Hypersensitivity to murine proteins or to 1 of the excipients of ravulizumab

Any medical condition that, in the opinion of the Investigator, may interfere with the patient's participation in the trial, poses any added risk for the patient, or confounds the assessment of the patient.

2.2.2. Prior/Concomitant Therapy

Previously or currently treated with a complement inhibitor.

Use of rituximab within 3 months prior to Screening.

Use of mitoxantrone within 3 months prior to Screening.

Use of Intravenous Immunoglobulin (IVIg) within 3 weeks prior to Screening.

2.2.3. Prior/Concurrent Clinical Study Experience and Other Exclusions

Participation in any other investigational drug study or exposure to an investigational drug or device within 30 days of Screening or 5 half-lives of the study drug, whichever is greater.

Pregnant, breastfeeding, or intending to conceive during the course of the study 2.3. Lifestyle Considerations There is no lifestyle restriction for this study.

2.4. Screen Failures

Screen failures are defined as patients who consent to participate in the clinical study but are not subsequently treated with study drug. Individuals who do not meet the criteria for participation in this study (screen failure) due to a reason that is expected to resolve or has resolved, may be rescreened based on discussion and agreement between the Investigator and the Medical Monitor. A patient who experiences a relapse that meets the protocol definition of an On-Trial Relapse (Section 5.2.3.2) during the Screening Period will be considered a screening failure. Such patients may be rescreened for enrollment into the trial after receiving treatment for the relapse and when, in the opinion of the Investigator and the Medical Monitor, the patient is medically stable (Section 2.1; Section 2.2). The patient must meet the enrollment criteria at re-screening to enter the study.

3. Study Drug

Study drug is defined as any study drug(s), marketed product(s), placebo, or medical device(s) intended to be administered to a study patient according to the study protocol.

3.1. Study Drug(s) Administered

In this study, patients receive open-label ravulizumab during the entire treatment period (Table 2; refer to Section 5.1.6 for study drug dosage and administration and SoA (FIG. 2) for dosing schedules.

TABLE 2

| Study Drug. | |
| --- | --- |
| Study drug Name | Ravulizumab |
| Type | Biologic |
| Dose Formulation | Ampule |
| Physical Description | Clear to translucent, slight whitish color, practically free from particles |
| Unit Dose Strength(s) | 300 mg (10 mg/mL concentrated solution) |
| Dosage Level(s)$^a$ | Weight-based dose, starting 2 weeks after the initial loading dose, then maintenance dose q8w |

TABLE 2-continued

| Study Drug. | |
|---|---|
| Route of Administration | IV infusion |
| Use | Experimental |
| IMP and N IMP | IMP |
| Sourcing | Provided centrally by the Sponsor or contracted manufacturing organization |
| Packaging and Labeling | Study drug will be provided in glass vials and stoppered with a butyl rubber stopper with an aluminum overseal and a flip-off cap. Study drug will be supplied in kits and labeled as required per country requirement. |

IMP = investigational medicinal product;
IV = intravenous;
NIMP = non-investigational medicinal product;
q8w = once every 8 weeks
Detailed information of study drug dose administration is provided in Section 5.1.6

3.2. Preparation/Handling/Storage/Accountability

Upon arrival of the study drug at the study site, the study drug kits are removed from the shipping container and stored in their original cartons under refrigerated conditions at 2° C. to 8° C. (35° F. to 47° F.) and protected from light. Ravulizumab is not frozen. Study drug is stored in a secure, limited-access storage area with temperature monitored daily.

Infusions of study drug should be prepared using aseptic technique. Ravulizumab is further diluted in a 1:1 ratio with compatible diluent. Ravulizumab is filtered with a 0.2 micron filter during infusion. In addition, the infusion of study drug follows the following rules:

The investigator or designee confirms appropriate temperature conditions have been maintained during transit for all study drug received and any discrepancies are reported and resolved before use of the study drug.

Only patients enrolled in the study may receive study drug and only authorized site staff may supply or administer study drug. All study drug is stored in a secure, environmentally controlled, and monitored (manual or automated) area in accordance with the labeled storage conditions with access limited to the investigator and authorized site staff.

The investigator, institution, or the head of the medical institution (where applicable) is responsible for study drug accountability, reconciliation, and record maintenance (e.g., receipt, reconciliation, and final disposition records).

Further guidance and information for the final disposition of unused study drugs are provided in the Pharmacy Manual.

3.3. Measures to Minimize Bias: Randomization and Blinding

This is a single-arm, open-label study. All study patients, site personnel, Sponsor staff, Sponsor designees, and all staff directly associated with the conduct of the trial are unblinded to patient treatment assignments.

To minimize potential for bias in this open-label study, operational measures are employed regarding the efficacy endpoints and adjudication process. The trial database is monitored according to prespecified guidelines to confirm that all potential relapses are collected and analyzed. An independent Relapse Adjudication Committee evaluated each On-Trial Relapse and confirmed whether it meets the protocol defined criteria for an NMOSD relapse (Section 5.2.3.2). Additionally, while the EDSS Raters are aware that all patients are on ravulizumab, the EDSS Raters are blinded to all trial data when making their assessments.

3.4. Study Drug Compliance

The infusion of study drug into patients is under the supervision of the Investigator or their designee to ensure that the patients receive the appropriate dose at the appropriate timepoints during the study.

The date and time of each dose administered in the clinic are recorded in the source documents and recorded in the case report form (CRF).

The dose of study drug and study patient identification is confirmed at the time of dosing by a member of the study site staff other than the person administering the study drug.

3.5. Concomitant Therapy

Any medication (including over-the-counter or prescription medicines, vitamins, minerals, and/or herbal supplements) or vaccine that the patient is receiving at the time of enrollment or receives during the study is recorded in the patient's source document/medical chart and electronic case report form (eCRF) along with:

Reason for use

Dates of administration including start and end dates

Dosage information including dose and frequency

Any changes in concomitant medications is also recorded in the patient's source document/medical chart and eCRF. When possible, concomitant medications are recorded from the first infusion of ravulizumab until the patient discontinues or completes the study.

Information regarding the use of ISTs including steroids is collected. Meningococcal vaccination and antibiotics administered for prophylaxis of meningococcal infection (if applicable) are also recorded.

Any concomitant medication deemed necessary for the patient's care during the study, or for the treatment of any AE, along with any other medications, other than those listed as disallowed medications in Section 3.5.2, may be given at the discretion of the Investigator. It is the responsibility of the Investigator, however, to ensure that details regarding all medications are recorded in full in the patient's source document/medical chart and eCRF.

The Medical Monitor is contacted if there are any questions regarding concomitant or prior therapy.

3.5.1. Allowed Medications and Therapies

The following concomitant medications and therapies are allowed in this study.

3.5.1.1. Palliative and Supportive Care

Palliative and supportive care is permitted during the course of the trial for underlying conditions.

3.5.1.2. Immunosuppressive Agents

The supportive immunosuppressive therapies (ISTs) for relapse prevention, either in combination or monotherapy, are permitted at the discretion of the Investigator, such as:

corticosteroids
azathioprine (AZA)
mycophenolate mofetil (MMF)
methotrexate (MTX)
tacrolimus (TAC)
cyclosporine
cyclophosphamide If a patient receives supportive ISTs prior to the study and continues to receive stable maintenance therapy during the study, referred to inclusion criteria (Section 2.1) for the requirements on ISTs to ensure that the patient is on a stable dose within limits required for this study as described in study criteria (Section 2).

For each patient, no adjustment in IST dosage and no new ISTs are permitted for the first 106 weeks, unless the patient experiences a relapse or a safety event, and a change in IST dose or regimen is deemed necessary by the Investigator to guarantee the patient's safety.

Any changes in immunosuppressive therapy are recorded in the source documents and eCRF page for concomitant medication.

3.5.1.3. Standardized Treatment for Relapse

The treatment of relapse is at the discretion of the Treating Physician. The following standardized treatment regimen for a confirmed On-Trial Relapse (Section 5.2.3.2) is recommended, in accordance with expert opinion.

One gram (1 g) intravenous methylprednisolone (IVMP) administered daily for 3-5 days followed by oral prednisone tapering.

If the patient improves, then continue the trial assessments as per schedule of this protocol.

If there is no or minimal response to IVMP, PE/PP will be allowed at the discretion of the treating neurologist. Five cycles of PE, each removing 1.0-1.5 volumes of circulating plasma, are recommended for treatment of attacks that do not respond to IVMP.

If a patient undergoes PE/PP for an On-Trial Relapse during the Treatment Period, a supplemental dose of study drug should be administered after each PE/PP as described under Supplemental Dose in Section 5.1.6.2. After receiving the supplemental dose, the patient will continue on the protocol-specified dosing schedule in the SoA (FIG. 2).

3.5.2. Disallowed Medications and Therapies

The following medications and therapies are prohibited during the study.

Mitoxantrone
Rituximab or other biologics such as tocilizumab
Immunomodulatory therapies, including interferon beta-1b; interferon beta-1a, glatiramer acetate, natalizumab, alemtuzumab, dimethyl fumarate, teriflunomide, siponimod, and fingolimod.
IVIg for relapse prevention
PE for relapse prevention 3.6. Dose Modification Dose modification is not permitted for this study.

3.7. Intervention after the End of the Study

Ravulizumab is not provided to the patients after the last scheduled dosing (FIGS. 2 and 3). All patients are followed for safety for an additional 8 weeks after the last dose of study drug or early discontinuation.

4. Discontinuation of Study Drug and Patient Discontinuation or Withdrawal 4.1. Discontinuation of Study Drug In rare instances, it may be necessary for a patient to permanently discontinue (definitive discontinuation) the study drug. If the study drug is definitively discontinued, the patient will remain in the study to be evaluated for safety follow up. See the SoA (FIGS. 2 and 3) for data to be collected at the time of discontinuation of the study drug and follow-up and for any further evaluations that needs to be completed.

Patients are considered for discontinuation from the study drug if any of the following occurred during the study:

Serious hypersensitivity reaction;
Severe uncontrolled infection;
Use of disallowed medication as defined in Section 3.5.2
Pregnancy or planned pregnancy; or
Sponsor or the Investigator deems it is necessary for the patient.

4.2. Patient Discontinuation/Withdrawal from the Study

All efforts should be made to ensure patients are willing to comply with study participation prior to conducting the screening procedures. The study staff should notify the Sponsor and their site monitor of all trial withdrawals as soon as possible. The reason for patient discontinuation is recorded in the source documents and eCRF.

A patient may withdraw from the study at any time at his/her own request, or may be withdrawn at any time at the discretion of the investigator for safety, behavioral compliance, or administrative reasons. This is expected to be uncommon.

At the time of discontinuing from the study, if possible, an early discontinuation visit will be conducted, as shown in the SoA (FIG. 2). Patients who discontinue early are followed for safety for an additional 8 weeks and for any further evaluations that need to be completed.

The patient is permanently discontinued both from the study drug and from the study at that time.

If the patient withdraws consent for disclosure of future information, the sponsor may retain and continue to use any data collected before such a withdrawal of consent.

4.3. Lost to Follow Up

If a patient fails to return, or is otherwise unavailable, for a scheduled visit within the acceptable visit window (FIG. 2), the site study staff will make a reasonable attempt to contact the patient to determine the reason for missing the appointment.

Patients who fail to return for a scheduled visit will be contacted by the site's study staff to determine the reason for missing the appointment. As it is vital to obtain any patient's missing visit information to ensure the missed appointment is not due to an AE or potential relapse, every effort will be made to undertake protocol-specified safety follow-up procedures.

In the exceptional circumstance where a patient cannot or does not come to the study site for examination, the patient will be instructed to see his or her local neurologist or physician. In this event, if possible, the Treating Physician or designee will contact the local neurologist or physician to obtain as much information as possible about the patient's medical and neurological condition, and provide clinical guidance, if needed. The study site will obtain relevant medical records as documentation from the local physician's examination, and enter relevant data in the Relapse Evaluation Visit form or in the AE form as appropriate.

A patient is considered lost to follow-up if he or she repeatedly fails to return for scheduled visits and is unable to be contacted by the study site.

The following actions will be taken if a patient fails to return to the clinic for a required study visit:

The site attempts to contact the patient and reschedule the missed visit as soon as possible and counsel the patient on the importance of maintaining the assigned visit schedule and ascertain whether or not the patient wishes to and/or should continue in the study.

Before a patient is deemed lost to follow up, the investigator or designee makes every effort to regain contact with the patient (where possible, 3 telephone calls and, if necessary, a certified letter to the patient's last known mailing address or local equivalent methods). These contact attempts are documented in the patient's medical record.

Should the patient continue to be unreachable, he/she will be considered as lost to follow up.

5. Study Assessments and Procedures

Study procedures and their timing are summarized in the SoA (FIG. 2). Protocol waivers or exemptions are not allowed. Immediate safety concerns are discussed with the Sponsor immediately upon occurrence or awareness to determine if the patient should receive study drug. Adherence to the study design requirements, including those specified in the SoA, is essential and required for study conduct. All screening evaluations are completed and reviewed to confirm that potential patients meet all eligibility criteria. The investigator maintains a screening log to record details of all patients screened and to confirm eligibility or record reasons for screening failure, as applicable. Procedures conducted as part of the patient's routine clinical management (e.g., blood count) and obtained before signing of the ICF may be utilized for screening or baseline purposes provided the procedures meet the protocol-specified criteria and are performed within the time frame defined in the SoA.

5.1. General Assessments and Procedures 5.1.1. Informed Consent

The investigator or qualified designee obtains a signed and dated informed consent form from each patient prior to conducting any study procedures. All efforts are made to ensure patients are willing to comply with trial participation prior to conducting the screening procedures.

5.1.2. Treating Physician

The Treating Physician is the Principal Investigator (PI)/Sub-investigator for the study who is responsible for the overall patient management including patient eligibility evaluation, supervision of the study drug administration, recording and treating of AEs and monitoring of safety assessments.

At the time of a relapse, the Treating Physician performs a complete neurologic examination and determines if the patient's symptoms and signs meet the criteria for an On-Trial Relapse (Section 5.2.3.2). They may also treat the patient's relapse according to the recommended On-Trial Relapse Treatment regimen. Ultimately, treatment and treatment options for On-Trial Relapse as well as any changes in the ISTs following an On-Trial Relapse are at the discretion of the Treating Physician.

5.1.3. Medical History and NMOSD History

The investigator reviews the patient's history and diagnosis and documented the following at the Screening Visit:

NMOSD diagnosis date as well as prior Magnetic Resonance Imaging (MRIs) that contributes to the diagnosis. Confirmation of the NMOSD diagnosis as defined by the International Panel for NMO Diagnosis (IPND) criteria (Section 7.1), including the specific criteria the patient meets for the diagnosis. Only patients who are both anti-AQP4 Ab-positive and otherwise meet the 2015 IPND criteria are be eligible for participation.

All available information about relapses that occur before screening and that meets the protocol definition of Historical Relapse (Section 5.2.3.1) will be recorded, including The number of relapses (onset dates)

The clinical presentation of each relapse (e.g., optic neuritis [ON], transverse myelitis [TM], brainstem, area postrema, or other)

Acute and maintenance treatments and dosing regimens, and

Any disability measurements such as EDSS scores.

5.1.4. Vaccine and Antibiotic Prophylaxis

As with any terminal complement antagonist, the use of ravulizumab increases the patient's susceptibility to meningococcal infection (*N. meningitidis*). To reduce the risk of meningococcal infection, all patients are vaccinated against meningococcal infections within the 3 years before or at the time of initiating study drug.

Patients who initiate study drug less than 2 weeks after receiving a meningococcal vaccine will receive treatment with appropriate prophylactic antibiotics until 2 weeks after vaccination.

Patients are vaccinated or revaccinated according to current national vaccination guidelines or local practice for vaccination use with complement inhibitors (e.g., eculizumab, ravulizumab).

Vaccines against serotypes A, C, Y, W135, and B, where available, are recommended to prevent common pathogenic meningococcal serotypes.

Vaccination may not be sufficient to prevent meningococcal infection. Consideration is given per official guidance and local practice on the appropriate use of antibacterial agents.

All patients are monitored for early signs of meningococcal infection, evaluated immediately if infection is suspected, and treated with appropriate antibiotics, if necessary.

5.1.5. Inclusion/Exclusion Criteria

All inclusion (Section 2.1) and exclusion (Section 2.2) criteria are reviewed by the investigator or qualified designee to ensure the patient qualifies for study participation. Both the Investigator and the Sponsor must approve patient eligibility before enrollment.

5.1.6. Study Drug Administration

This section describes the dosage regimen of study drugs. At the scheduled dosing visits (FIG. 2), study drug administration is performed after all other tests and procedures are completed, excluding the post dose blood sampling for PK and free C5.

5.1.6.1. Ravulizumab

Patients receive a weight-based loading dose of ravulizumab via IV infusion on Day 1, followed by a weight-based maintenance dose on Day 15 (Table 3), then once every 8 weeks (q8w) thereafter. The entire treatment duration is up to 4 years, when all patients complete the 2 year Long-Term Extension Period or until ravulizumab is approved and/or available (in accordance with country-specific regulations), whichever occurs first. Depending on when a relapse occurs, ravulizumab scheduled dosing visits may or may not overlap with the Relapse Evaluation Visit and/or Follow-Up Relapse Evaluation Visits. Ravulizumab dosing visits continue as scheduled during the Relapse Evaluation Period.

TABLE 3

| Weight-based Doses of Ravulizumab. | | |
| --- | --- | --- |
| | Body Weight (kg)[a] | Dose (mg) |
| Loading dose | ≥40 to < 60 | 2400 |
| | ≥60 to < 100 | 2700 |
| | ≥100 | 3000 |
| Maintenance dose | ≥40 to < 60 | 3000 |
| | ≥60 to < 100 | 3000 |
| | ≥100 | 3600 |

Dose regimen will be based on the last recorded study visit body weight.
If the study drug is prepared the night before a visit, the weight from die most recent study visit should be used.

5.1.6.2. Supplemental Dose

During the study, PE/PP is allowed at the discretion of the Treating Physician for On-Trial Relapse (Section 3.5.1.3). If PE/PP is administered on a non-dosing visit as specified in the SoA (FIG. 2), a supplemental dose will be administered within 4 hours after PE/PP is completed, and will be based on the most recently administered ravulizumab dose (Table 4). If PE/PP is administered on a scheduled dosing visit as specified in the SoA (FIG. 2), a ravulizumab supplemental dose will not be administered. Patients will receive their regular dose of ravulizumab (Section 5.1.6.1) 60-120 minutes after PE/PP is completed (Refer to Section 5.6.2 for PK and free C5 sample collection during On-Trial Relapse).

After receiving the supplemental dose, patients are to continue study drug infusion according to the protocol-specified dosing schedule (FIG. 2).

TABLE 4

| Supplemental Dose of Ravulizumab Administered at Nonscheduled Dosing Visits After PE/PP Treatment for On-Trial Relapse. | | |
| --- | --- | --- |
| Dose Name | Most Recently Scheduled Dose | Supplemental Dose (mg) |
| Loading dose | 2400 | 1200 |
| | 2700 | 1500 |
| | 3000 | 1500 |
| Maintenance dose | 3000 | 1500 |
| | 3300 | 1800 |
| | 3600 | 1800 |

5.2. Efficacy Assessments

5.2.1. Neurologic Examination

A complete general neurologic examination is performed at the scheduled visits (FIG. 2) by the Treating Physician (Section 5.1.2) who is a study investigator and has been properly trained as clinical evaluator, preferably the same Treating Physician, throughout the study.

The complete general neurologic examination includes assessments of the following systems: mental status, fundus examination, cranial nerves, deep tendon reflexes, plantar responses, power/strength, sensation, coordination, and gait/balance.

5.2.2. NMO Symptom Card and Evaluation

Before receiving the first dose of study drug at the Day 1 Visit, patients are given an NMO Symptom Card, which listed potential signs and symptoms of NMOSD relapse and contact information.

At each visit throughout the study, study staff ensures that the patient has the NMO Symptom Card. The Treating Physician reviews and assesses the patient for any signs or symptoms indicative of relapse.

5.2.3. Relapse

5.2.3.1. Historical Relapse

Historical relapses are the relapses that occurred before the Screening Visit, including the first NMOSD attack. For this protocol, historical relapse is defined as a new onset of neurologic symptoms or worsening of existing neurologic symptoms with an objective change on neurologic examination (clinical findings or MRI findings, or both) that persists for more than 24 hours. Events that occurs within a 30-day interval are considered as one relapse.

5.2.3.2. On-Trial Relapse

5.2.3.2.1 Definition of On-Trial Relapse

On-Trial Relapses are acute attacks that occur during the study treatment period. For this protocol, On-Trial Relapse is defined as a new onset of neurologic symptoms or worsening of existing neurologic symptoms with an objective change (clinical sign) on neurologic examination that persisted for more than 24 hours as confirmed by the Treating Physician (Section 5.1.2). The signs and symptoms must be attributed to NMOSD, i.e., not caused by an identifiable cause such as infection, excessive exercise, or excessively high ambient temperature. Isolated changes on MRI or other imaging investigation with no related clinical findings are not considered an On-Trial Relapse.

5.2.3.2.2 Evaluation of On-Trial Relapse

On-Trial Relapses are monitored throughout the study. The Investigator or a qualified designee reviews the signs and symptoms of a potential relapse with the patient in detail at each visit.

Patients are educated on the potential signs and symptoms of NMOSD relapse and are instructed to contact the study site at the first sign or symptom of a potential relapse.

Patients are evaluated within 24 hours (and no later than 48 hours) of notification of signs or symptoms suggestive of a potential relapse.

Evaluation of On-Trial Relapses includes the following:

Complete neurological examination to determine whether the clinical signs, symptoms and examination findings meet the definition of an On-Trial Relapse Assessment of relapse severity based on the OSIS (Section 5.2.8; FIG. 8). The OSIS Visual Acuity (VA) Subscale Scores are used to categorize the severity of ON. The OSIS Motor Subscale Scores and Sensory Subscale Scores are used to categorize the severity of TM.

Evaluation of the neurological functional systems based on the Kurtzke's Functional System Scores (FSS) and the disability level based on the EDSS score (Section 5.2.4).

Ambulatory function assessment using the HAI (Section 5.2.7).

Ophthalmological examination including VA, confrontational visual fields (VF), and color vision (Section 5.2.9).

MRI +/− gadolinium and/or ocular coherence tomography (OCT) examinations are performed to evaluate a potential relapse as determined by the investigator (Section 5.2.10).

Additional tests and the follow-up evaluation as specified in the SoA (FIG. 3)

5.2.3.2.3 Treatment for On-Trial Relapse

At the time of a suspected relapse, the Treating Physician (Section 5.1.2) performed a complete neurologic examination to determine if a patient is experiencing an On-Trial Relapse. If the event is determined as an On-Trial Relapse by the Treating Physician, treatment for relapse, as well as any changes in the ISTs following relapse, are at the discretion of the Investigator.

The recommended standardized treatment for On-Trial Relapse is provided in Section 3.5.1.

Refer to Section 5.1.6 for administration of ravulizumab supplemental dose during an On-Trial Relapse.

5.2.3.2.4 On-Trial Relapse Follow-up

Relapse Evaluation Visits to monitor the course of the relapse is performed according to the schedule specified in the SoA (FIG. 3). Additional (unscheduled) Follow-up Relapse Evaluation Visits outside the specified time points is made at the discretion of the investigator or the sub-investigator.

Following a relapse, a patient may continue in the trial if the patient and the investigator/sub-investigator decides that it is appropriate to continue to receive study drug.

All reports of possible relapses and actions taken for the possible relapse are documented in the patient's source documents and recorded in the eCRF.

5.2.3.2.5 Adjudication of On-Trial Relapse

On-Trial Relapses are independently reviewed by the Relapse Adjudication Committee (RAC), which consist of physicians who have particular expertise in NMOSD and conduct independent reviews of all On-Trial Relapses. The Committee decides by majority vote whether each reported On-Trial Relapse meets the objective criteria for an On-Trial Relapse. A separate Charter documents all adjudication criteria and procedures for this study.

5.2.4 Expanded Disability Status Scale (EDSS)

The 10-point Kurtzke EDSS (Section 7.2) is widely used and accepted as a valid tool for quantifying disability and monitoring changes in disability over time (Kurtzke, J., *Neurology*, 33:1444-52, 1983). The EDSS scale ranges from 0 to 10.0 in 0.5 unit increments.

5.2.4.1. Expanded Disability Status Scale

The total EDSS score is determined by 2 factors: gait and FSS (Section 5.2.4.2), as described below:

EDSS scores below 4.0 are determined by the FSS alone.

People with EDSS scores of 4.0 and above may have some degree of gait impairment.

EDSS scores between 4.0 and 9.5 are determined by both gait abilities and the FSS.

5.2.4.2. Functional Systems Scores

A functional system (FS) represents a network of neuronal systems responsible for particular tasks/functions. The EDSS assigns a severity score to the patient's clinical status using FSS that evaluate dysfunction in the following 8 FSs (Section 7.2). The FS of functional systems 1 through 7 are scored on a scale of 0 (low level of problems) to 5 or 6 (high level of problems) to best reflect the level of disability observed clinically. The "Other" category consists of any other neurologic findings attributed to NMOSD and is dichotomous, with 0 as none and 1 as any present.

5.2.4.3. EDSS and FSS Rater

The EDSS and FSS are administered in person by a trained rater. The EDSS Rater performs a complete Kurtzke neurologic examination and documents the FSS and the EDSS score. The following rules apply:

The EDSS Rater shall not be the PI and cannot be directly involved in the trial patient's management. When possible, the EDSS Rater should be a physician. If a non-physician EDSS Rater (e.g., specialized nurse) is used, the rater must be approved by the Sponsor before performing the assessments.

The EDSS Rater remains blinded to all other study data as well as all other patient clinical data.

The blinded EDSS Rater is responsible for performing the EDSS assessments throughout the study including at the time of a relapse. When possible, the same blinded rater performs the EDSS for each patient at visits specified in the SoA.

The EDSS Rater performed a complete Kurtzke neurologic examination, as described in Section 7.2 and documented the Functional Systems Scores (FSS) and the EDSS score (Kurtzke, 1983).

For specific requirements for EDSS Rater qualification, refer to the training materials provided by the Sponsor. Refer to Table 5 for the roles and responsibilities of Investigator and EDSS Rater.

TABLE 5

| Roles and Responsibilities of The Investigator/Treating Physician and EDSS Rater. | |
| --- | --- |
| Treating Physician | EDSS Rater |
| At protocol-specified timepoints: | At protocol-specified timepoints: |
| Determine patient eligibility for the study | Kurtzke neurological assessment |
| Overall patient management during the | Document FSS |
| study, including study drug administration | Record EDSS score |
| and safety assessments. | At the time of relapse: |
| At the time of relapse: | Perform the Kurtzke neurologic |
| Initial patient assessment | assessment |
| Have the EDSS Rater record FSS and | Document FSS |
| EDSS score[a] | Record EDSS score |
| Perform a complete neurologic | |
| examination | |
| Determine if the patient has experienced an | |
| On-Trial Relapse | |
| Determine relapse severity by OSIS | |
| Assess VA[a], confrontational visual fields, | |
| and color vision[a] | |

TABLE 5-continued

Roles and Responsibilities of The Investigator/Treating Physician and EDSS Rater.

| Treating Physician | EDSS Rater |
|---|---|
| Assess ambulation by HAI[a] | |
| Have the patient complete the EQ-5D and | |
| SF-36 | |
| Treat relapse | |

EDSS = Expanded Disability Status Scale;
EQ-5D = Euro Quality of life-5 Dimensions;
FSS = functional systems score;
HAI = Hauser ambulation index;
OSIS = Optic spinal impairment score;
SF-36 = short form health survey;
VA = visual acuity.
[a]Can be performed by the Investigator or a designee.

5.2.5. EuroQoL 5 Dimensions (EQ-5D)

The Euro Quality of Life (EQ-5D) (FIG. 5) is a self-assessed, standardized instrument to measure health-related QoL, which has been used in a wide range of health conditions, including NMOSD (Schrag, A. et al., *J. Neurol. Neurosurg. Psychiatry,* 69:67-73, 2000). The EQ-5D consists of 2 pages: the EQ-5D descriptive system and the EQ visual analogue scale (EQ VAS) (FIG. 5). EQ-5D is administered prior to other study procedures at each visit.

5.2.5.1. EQ-51D Descriptive System

The descriptive system is a 5-component scale including mobility, self-care, usual activities, pain/discomfort, and anxiety/depression. Each level is rated on a scale that describes the degree of problems in that area.

5.2.5.2. EQ Visual Analogue Scale

The EQ-5D VAS is an overall health state scale where the patient selects a number between 0-100 to describe the condition of their health, with 100 being 'The best health state you can imagine' and 0 being 'The worst health state you can imagine.'

This information can be used as a quantitative measure of health outcome as judged by the individual respondents. Previously published studies by EuroQol Group members show preliminary evidence of the instrument's feasibility, reliability and validity.

5.2.6. Short Form Health Survey (SF-36)

The SF-36 is a 36-item self-report of health-related quality of life (Stewart, A. L., & Ware, J. E., Jr. (Eds.). (1992). Measuring functioning and well-being: The medical outcomes study approach. Durham, N.C.: Duke University Press; Ware, J. E., Jr. (1988). How to score the revised MOS short-form health scales. Boston: Institute for the Improvement of Medical Care and Health, New England Medical Center). It contains 8 subscales measuring different domains of health-related quality of life: physical functioning, role limitations due to physical problems, bodily pain, general health perceptions, vitality, social functioning, role-limitations due to emotional problems, and mental health. The two summary scores are the physical component summary and the mental component summary. There is no single overall score for the SF-36.

5.2.7. Hauser Ambulation Index (HAI)

The HAI is a rating scale developed to assess mobility by evaluating the time and degree of assistance required to walk 25 feet (FIG. 7). The Treating Physician or an appropriately trained designee performs the HAI test at the protocol specified visits (FIG. 3), as briefly described below.

Patients are asked to walk a marked 25-foot course as quickly and safely as possible.

The examiner records the time and type of assistance (e.g., cane, walker, crutches) needed. The rating scale also has categories for patients who are unable to walk.

Although the patient's walking is timed, the time is not used directly but is utilized in conjunction with other factors to rate the patient on an ordinal scale with 11 gradations (Bethoux, F. and Bennett, S., *Int. J. Care,* 13:4-14, 2011). This assessment is performed for all patients in this study.

5.2.8. Optic Spinal Impairment Score (OSIS)

The OSIS is a scoring system for evaluating the severity of a relapse (FIG. 8). The OSIS VA Subscale Scores are used to categorize the severity of ON. The OSIS Motor Subscale Scores and Sensory Subscale Sc ores are used to categorize the severity of TM. The OSIS is assessed at baseline and at the time of On-Trial Relapse by the Treating Physician Further instruction on OSIS evaluation of On-Trial Relapse is provided in Section 5.2.3.2.

5.2.9. Ophthalmologic Examination

5.2.9.1. Confrontational Visual Fields

Confrontational VF is evaluated by the Treating Physician. It is critical for these assessments that the baseline ophthalmologic status be known so that changes in the examination can be used to evaluate prior or ongoing ON. Central scotomas are common in patients experiencing ON; however, visual field deficits can present with a broad spectrum of patterns (Keltner, J. et al., *Am. J. Ophthalmol.,* 128:543-53, 1999).

5.2.9.2. Color Vision

Color vision is assessed by the Treating Physician or any appropriately trained designee using Ishihara Plates. Loss of color vision can be a marker of ON and is therefore an important assessment tool in NMOSD.

5.2.9.3. Visual Acuity

Visual acuity is usually affected by ON, progressing over a period of hours to days. The Landolt C ring chart is used to assess VA.

The Landolt C consists of a ring that has a gap, thus looking similar to the letter C. The gap can be at various positions (usually left, right, bottom, top and the 450 positions in between) and the task of the tested person is to decide on which side the gap is. The size of the C and its gap are reduced until the patient makes a specified rate of errors. The minimum perceivable angle of the gap is taken as measure of the visual acuity.

The Treating Physician or an appropriately trained designee performs the VA test at the protocol specified visits (FIG. 3), as described below.

The test is performed at a standard distance, typically 6 meters or 20 feet.

The Landolt chart is typically recorded as acuity ratio distance (6 meters or 20 feet), so for normal VA it will be recorded as 20/20 or 6/6. Sometimes this is entered as the denominator of the Landolt fraction (in US) or as a decimal (ex-US).

The test is always done with the best possible correction (e.g., wearing glasses) as needed and each eye is tested independently.

5.2.10 Magnetic Resonance Imaging and Ocular Coherence Tomography

Baseline MRI of brain, cervical spine, and thoracic spine (contrast is optional) and OCT examinations are performed. Exceptions may be granted (e.g., based on a recent historical result being available for the study) if approved by the Alexion Medical Monitor.

At the time of relapse, MRI of brain, cervical spine, and/or thoracic spine (contrast is optional) and/or OCT are performed to evaluate a potential relapse at the discretion of the Investigator when deemed clinically relevant.

Follow-up assessments are performed promptly after On-Trial Relapse if the investigator decides these are indicated (Section 5.2.3).

5.3. Safety Assessments

Planned time points for all safety assessments are provided in the SoA (FIGS. 2 and 3).

5.3.1. Physical Examinations

A complete physical examination includes, at a minimum, assessments of the following organs/body systems: skin, head, ears, eyes, nose, throat, neck, lymph nodes, pulse, chest, heart, abdomen, extremities and musculoskeletal. A targeted physical examination includes, at a minimum, a body-system relevant examination based upon Investigator judgment and patient symptoms.

Investigators pay special attention to clinical signs related to previous serious illnesses. For consistency, all efforts are made to have the physical examination performed by the same qualified study staff at each study visit. Additional Physical Examinations can be performed as medically indicated during the study at the Investigator's discretion.

5.3.2. Height and Weight

Body weight is measured in pounds or kilograms. Height is measured in inches or centimeters.

5.3.3. Vital Signs

Oral temperature (° C. or ° F.), pulse rate, respiratory rate (RR), and systolic and diastolic blood pressure (BP) (mm Hg) are assessed. Blood pressure and pulse measurements are assessed seated with a completely automated device. Manual techniques are used only if an automated device is not available. Blood pressure and pulse measurements are preceded by at least 5 minutes of rest for the patient in a quiet setting without distractions (e.g., television, cell phones). Ideally, the same arm for each patient is used for measurements.

5.3.4. Electrocardiograms

Single 12-lead ECG is performed at protocol specified visits in the SoA (FIGS. 2 and 3) using an ECG machine to obtain heart rate and measures of PR, QRS, QT and QTc intervals. Patients are supine for approximately 5-10 minutes before ECG collection and remain supine but awake during ECG collection. The Investigator or qualified designee is responsible for reviewing the ECG to assess whether the ECG is within normal limits and determine the clinical significance of the results. These assessments are recorded in the source documents and the eCRF.

5.3.5. Patient Safety Card

Before the first dose of study drug, a Patient Safety Card is provided to study patients to carry with them at all times.

The card is provided to increase patient awareness of the risk of infections, especially meningococcal infection and promote quick recognition and disclosure of any potential signs or symptoms of infection experienced by study patients during the course of the study and to inform patients on what actions must be taken if they are experiencing signs or symptoms of infection.

At each visit throughout the study, the study staff ensures that the patient has the Patient Safety Card.

5.3.6. Prior and Concomitant Medical Review

It is important for investigators or a qualified designee to review each medication the patient is taking before starting the study and at each visit.

5.3.6.1. Prior Medications

Prior medications and/or vaccines (including vitamins, herbal preparations, and those discussed in the exclusion criteria Section 2.2) and procedures (any therapeutic intervention, such as surgery/biopsy or physical therapy) that the patient takes or undergoes within 30 days before the start of Screening or during the Screening Period before the first dose of ravulizumab, as well as any meningococcal vaccine administered within the last 3 years, will be recorded in the patient's eCRF. Additionally, all medications or therapies ever used for relapse prevention or acute treatment of NMOSD (including steroids) before the first dose of ravulizumab will be collected.

5.3.6.2. Concomitant Medications

Use of concomitant medications and non-drug therapies (Section 6.5) is evaluated during the study. At each visit, patients are questioned about any new medication or non-drug therapies or changes to concomitant medications and non-drug therapies since the last visit. Concomitant medications and non-drug therapies are recorded in the source documents and the patient's eCRF.

5.3.7. Clinical Safety Laboratory Assessments

The investigator reviews the laboratory report, documents this review, and records any clinically relevant changes occurring during the study in the AE section of the CRF. The laboratory reports are filed with the source documents. Clinically significant abnormal laboratory findings are those that are not associated with the underlying disease, unless judged by the investigator to be more severe than expected for the patient's condition.

All laboratory tests with values considered clinically significantly abnormal during participation in the study or within 8 weeks after the last dose of study drug are repeated until the values return to normal or baseline or are no longer considered clinically significant by the investigator or medical monitor. If such values do not return to normal/baseline within a period of time judged reasonable by the investigator, the etiology is identified and the sponsor notified. All protocol-required laboratory assessments, as defined in Appendix 2, are conducted in accordance with the Laboratory Manual and the SoA. If laboratory values from non-protocol specified laboratory assessments performed at the institution's local laboratory required a change in patient management or are considered clinically significant by the investigator (e.g., or AE or dose modification), then the results are recorded in the CRF.

5.3.8. Suicidal Ideation and Behavior Risk Monitoring

As the study drug is being evaluated for a neurologic indication, patients being treated with the study drug are monitored appropriately and observed closely for suicidal ideation or behavior or any other unusual changes in behavior, especially at the beginning and end of the course of study drug, or at the time of dose changes.

Baseline assessment of suicidal ideation and behavior as well as intervention-emergent suicidal ideation and behavior are monitored during this study using the Columbia-suicide severity rating scale (C-SSRS).

There are 2 types of C-SSRS assessments that are conducted during the study: C-SSRS at Baseline (FIG. 10) and C-SSRS-Since Last Visit (FIG. 11). C-SSRS is performed by the Treating Physician or an appropriately trained designee at visits specified in the SoA to ensure that patients who are experiencing suicidal thoughts or behavior are properly recognized and adequately managed or referred for further evaluation. Additional C-SSRS assessments are permitted as needed.

5.4. Adverse Events and Serious Adverse Events

Adverse events are reported to the Investigator by the patient (or, when appropriate, by a caregiver, surrogate, or the patient's legally authorized representative).

The investigator and any qualified designees are responsible for detecting, documenting, and recording events that meet the definition of an AE or SAE and remains responsible for following up AEs that are serious, considered related to the study drug or study procedures, or that causes the patient to discontinue the study drug (see Section 4).

For this trial, information about relapses that do not meet the SAE criteria is recorded in source documents and in the eCRF as part of the Relapse Evaluation Visits and not reported as AEs.

5.4.1. Time Period and Frequency for Collecting Adverse Event and Serious Adverse Event In-formation All AEs and SAEs are collected from the signing of the ICF until the last visit at the time points specified in the SoA (FIGS. 2 and 3).

All SAEs are recorded and reported to the sponsor or designee immediately and under no circumstance is this exceed 24 hours, as indicated in FIGS. 2 and 3. The investigator will submit any updated SAE data to the sponsor within 24 hours of awareness.

Investigators are not obligated to actively seek AE or SAE after conclusion of the study participation. If, however, the investigator learns of any SAE, including a death, at any time after a patient has been discharged from the study, and he/she considers the event to be reasonably related to the study drug or study participation, the investigator must promptly notify the sponsor.

5.4.2. Method of Detecting AEs and SAEs

Care will be taken not to introduce bias when detecting AEs and/or SAEs. Open-ended and non-leading verbal questioning of the patient is the preferred method to inquire about AE occurrences.

5.4.3. Follow-up of AEs and SAEs

After the initial AE/SAE report, the investigator is required to proactively follow each patient at subsequent visits/contacts. All SAEs and AEs of special interest (AESI; as defined in Section 5.4.6), are followed until resolution, stabilization, the event is otherwise explained, or the patient is lost to follow-up (as defined in Section 4.3). Every effort is made to undertake protocol-specified safety follow-up procedures.

5.4.4. Regulatory Reporting Requirements for SAEs

Prompt notification by the investigator to the sponsor of a SAE is essential so that legal obligations and ethical responsibilities towards the safety of patients and the safety of a study drug under clinical investigation are met.

The sponsor has a legal responsibility to notify both the local regulatory authority and other regulatory agencies about the safety of a study drug under clinical investigation. The sponsor complies with country-specific regulatory requirements relating to safety reporting to the regulatory authority, Institutional Review Boards (IRB)/Independent Ethics Committees (IEC), and investigators.

Suspected unexpected serious adverse reactions (SUSAR) is reported according to local regulatory requirements and sponsor policy and forwarded to investigators as necessary.

An investigator who receives an investigator safety report describing a SAE or other specific safety information (e.g., summary or listing of SAEs) from the sponsor reviews and then files it along with the Investigator's Brochure and notifies the IRB/IEC, if appropriate according to local requirements.

5.4.5. Pregnancy

Pregnancy testing is performed on all WOCBP at protocol-specified timepoints in the SoA (FIGS. 2 and 3). Pregnancy tests (urine or serum) may also be performed at any time during the study at the Investigator's discretion.

A negative pregnancy test is required for WOCBP before study drug administration. The following rules apply:

Details of all pregnancies in female patients and, if indicated, female partners of male patients are collected after the start of study drug and until the termination of the pregnancy.

If a pregnancy is reported, the investigator will inform the sponsor within 24 hours of learning of the pregnancy.

Abnormal pregnancy outcomes (e.g., spontaneous abortion, fetal death, stillbirth, congenital anomalies, ectopic pregnancy) are considered SAEs. Pregnancy alone is not considered an AE If a patient becomes pregnant, the study drug will be immediately discontinued, and the Sponsor will be notified. Each pregnancy is followed to term and the Sponsor notified regarding the outcome.

5.4.6. Adverse Events of Special Interest

Meningococcal infections are collected as adverse events of special interest (AESI).

5.5. Treatment of Overdose

For this study, any dose of study drug greater than that specified in the protocol is considered an overdose.

Accidental overdose without any association with laboratory abnormalities or clinical symptoms is not considered as an AE. Overdose is reported by the investigator within 24 hours to the Sponsor regardless of its association with or without an AE.

The sponsor does not recommend specific treatment for an overdose.

In the event of an overdose, the investigator will:

Contact the Medical Monitor immediately.

Closely monitor the patient for any AE/SAE.

Obtain a plasma sample for PK analysis if requested by the Medical Monitor (determined on a case-by-case basis).

Document the quantity of the excess dose as well as the timing of the overdose in the CRF.

Decisions regarding dose interruptions will be made by the investigator in consultation with the Medical Monitor based on the clinical evaluation of the patient.

5.6. Pharmacokinetics and Pharmacodynamics

Blood samples for determination of serum drug concentrations and PD assessments will be collected before and after administration of study drug at the time points as specified in the SoA (FIGS. 2 and 3). Cerebrospinal fluid (CSF) samples for PK and PD assessments are optional at protocol specified timepoints (FIGS. 2 and 3) and will only be obtained from patients who consent to CSF collection. Instructions for the collection and handling of biological samples will be provided by the sponsor. The actual date and time (24-hour clock time) of each sample will be recorded on the eCRF and the central laboratory requisition form. Additional information on sample collection, including blood volume requirements, is provided in the Laboratory Manual.

5.6.1 Sample Collection During the Study Period

Baseline (B) and trough (T) PK and PD blood samples will be collected at pre-dose, within 90 minutes before administering study drug at visits specified in the SoA (Section 1.3). The pre-dose blood sample may be drawn through the venous access created for the dose infusion, prior to administration of the dose. Post-dose (P) PK and PD blood samples will be collected post-dose, within 120 minutes after completing study drug infusion. The post-dose blood samples will be drawn from the patient's opposite, non-infused arm. Blood samples at a non-dosing visit can be collected at any time. In the event of an unscheduled visit, PK and PD blood sample will be collected as soon as possible.

5.6.2 Sample Collection During the Study Period

Blood sample for PK and PD analyses will be collected at any time during the scheduled Relapse Evaluation Visit. If the relapse-associated blood sample collection schedule coincides with a regular sample collection specified in the SoA (FIGS. 2 and 3), however, the directions for regular PK and PD sample collection during the study (Section 5.6.1) should be followed.

During On-Trial Relapse, if the patient receives PE/PP and a supplemental dose of ravulizumab at the Relapse Evaluation Visit, 3 blood samples for PK and PD should be collected at the following intervals:

1. Approximately 5 to 90 minutes prior to PE/PP
2. After PE/PP and before study drug infusion
3. At least 60 minutes after the completion of study drug infusion If a patient receives PE/PP at any visit other than the Relapse-Evaluation Visit, blood samples for PK and PD will be collected immediately before and after each session of PE/PP. A post dose sample, (e.g., 1 hour after completion of supplemental study drug infusion), will also be collected.

5.7. Genetics

There are no prespecified genetic analyses in this study.

5.8. Biomarker Research 5.8.1. Exploratory Biomarker Research

Blood samples for biomarker research will be collected from all patients at timepoints specified in the SoA (FIGS. 2 and 3): CSF samples are optional samples for biomarker research and should only be collected from patients who have consented to CSF sample collection. Biomarkers will be measured and include, but are not limited to, assessments of the following:

AQP4-Ab at protocol-specified time points (Section 1.3 SoA), including during the Relapse Evaluation Period (see Section 5.2.3.2 for details).

Complement products

Markers of neuroinflammation, such as interleukin 6 (IL-6)

Markers of neural injury, such as neurofilament light chain (NfL)

5.8.2. Future Biomarker Research

DNA and RNA sample collection is optional. DNA and RNA blood samples must only be collected from patients that consent to it. Future DNA and RNA testing on these samples including, but not limited to, specific candidate genes/genome-wide analysis.

Remaining samples from pharmacokinetic, pharmacodynamic, immunogenicity, and biomarker testing will be stored for future biomarker research. Analyses may be performed on biomarker variants thought to play a role in NMOSD activity/progression or treatment response to ravulizumab. These samples may also be used to develop methods, assays, prognostics and/or companion diagnostics related to the study drug target, disease process, pathways associated with disease state, and/or mechanism of action of the study drug.

Samples may be stored for a maximum duration according to local regulations following the last patient's last visit for the study at a facility selected by the sponsor to enable further analyses.

5.9. Immunogenicity Assessments

Anti-drug antibodies (ADAs) to ravulizumab will be evaluated in serum samples collected pre-dose (within 5-90 minutes prior to the start of infusion of study drug) from all patients according to the SoA (FIGS. 2 and 3).

Additionally, serum samples should also be collected at the final visit from patients who discontinued study drug or were withdrawn from the study.

Serum samples will be screened for antibodies binding to ravulizumab and the titer of confirmed positive samples will be reported. Other analyses may be performed to verify the stability of antibodies to ravulizumab and/or further characterize the immunogenicity of ravulizumab.

The detection and characterization of antibodies to ravulizumab will be performed using a validated assay method by or under the supervision of the sponsor. Samples may be further characterized to determine the titer and the presence of neutralizing antibodies if deemed necessary. Samples may be stored for a maximum duration according to local regulations following the last patient's last visit for the study at a facility selected by the sponsor to enable further analysis of immune responses to ravulizumab.

5.10. Medical Resource Utilization and Health Economics

Medical resource utilization and health economics data, associated with medical encounters, will be collected in the CRF by the investigator and study-site personnel for all patients throughout the study. Protocol-mandated procedures, tests, and encounters are excluded.

The data collected may be used to conduct exploratory economic analyses and will include:

Number of surgeries, and other selected procedures (inpatient and outpatient)

Duration of hospitalization

Number and type of diagnostic and therapeutic tests and procedures

6. Statistical Considerations 6.1. Statistical Hypotheses

The time to first adjudicated On-Trial Relapse will be evaluated using the log-rank test; the null hypothesis will be that there is no difference in the survival curves of the ravulizumab and the placebo treatment groups. The alternative hypothesis will be that there is a difference between the two survival curves, and ravulizumab is superior to placebo.

The adjudicated ARR will be presented with a 95% confidence interval (CI) to provide an estimate of the adjudicated ARR rate for patients treated with ravulizumab. While a formal hypothesis test of the adjudicated ARR will not be performed, we expect that patients treated with ravulizumab will have a low ARR and that the upper bound of the 95% CI will not exceed 0.25 relapse/patient-year.

For HAI the null hypothesis will be that the odds of a better outcome are the same between the ravulizumab arm and the placebo arm. The alternative hypothesis will be that there is a difference in the odds of a better outcome between the treatment arms and that ravulizumab has higher odds of a better outcome.

For the EQ-5D index and the EQ-5D VAS, the null hypothesis will be that there is no difference between the distribution of the ravulizumab arm and the placebo arm. The alternative hypothesis will be that there is a difference between the distribution of the treatment arms and that ravulizumab is superior to placebo.

For the EDSS the null hypothesis will be that the odds of a worse outcome are the same between the ravulizumab arm and the placebo arm. The alternative hypothesis will be that there is a difference in the odds of a worse outcome between the treatment arms and that the odds of a worse outcome are higher in the placebo arm.

6.2. Sample Size Determination

This is an open-label, external placebo-controlled study to evaluate ravulizumab in NMOSD patients with the primary endpoint of time to first adjudicated On-Trial Relapse. The placebo treatment arm in Study NCT01892345 will serve as the external control.

The sample size and power calculation assumptions for this study using the primary endpoint, time to first relapse, are as follows:

Log-rank test for comparison of ravulizumab to placebo 47 patients in the placebo treatment group Power 90%

Two-sided 5% level of significance

Drop-out rate 2-10%

Relapse-free rate of 92% for the ravulizumab arm at 12 months

Relapse-free rate of 63% for the placebo arm at 12 months

With these assumptions, a maximum sample size of approximately 55 patients in the ravulizumab treatment group provides at least 90% power to detect a treatment difference in time to first positively adjudicated relapse.

6.3. Populations for Analyses

For purposes of analysis, the following populations are defined as shown in Table 6.

TABLE 6

Populations for analysis.

| Population | Description |
|---|---|
| Full analysis set (FAS) | All patients who receive at least 1 dose of study drug. |
| Safety set | All patients who receive at least 1 dose of study drug. |
| Per protocol set (PPS) | The PPS is a subset of the FAS, excluding patients with major protocol deviations. The PP population will include all patients who: Have no major protocol deviations or key inclusion/exclusion criteria deviations that might potentially affect efficacy. Patients who took at least 80% of the required treatment doses while they were in the treatment period. Further details will be provided in the statistical analysis plan (SAP). |
| Pharmacokinetic analysis set (PKS) | All patients who receive at least 1 dose of study drug and who have evaluable pharmacokinetic data |

6.4. Statistical Analyses

The primary analysis will be conducted when all patients have completed the Primary Treatment Period. This analysis will include all efficacy, safety, and PK/PD study data for regulatory submission purposes and will be the final analysis of the Primary Treatment Period. The SAP to support the primary analysis will be developed and finalized shortly after the protocol is final. If necessary, a final SAP will be developed prior to the completion of the long-term extension period to describe any additional long-term efficacy and safety analyses. This section is a summary of the planned statistical analyses of the primary and secondary efficacy endpoints and the safety analyses.

Summary statistics will be computed and displayed by treatment group and by visit, where applicable. Descriptive statistics for continuous variables will minimally include the number of patients, mean, standard deviation, minimum, median, and maximum. For categorical variables, frequencies, and percentages will be presented. Graphical displays will be provided as appropriate. All statistical analyses will be performed based on a 2-sided Type I error of 5% unless noted otherwise. Missing data will not be imputed.

Analyses will be performed using the SAS® software Version 9.4 or higher.

6.4.1. Efficacy Analyses

To account for potential differences in baseline characteristics between the ravulizumab group and the external placebo control, efficacy analyses will include covariate adjustment methodologies, as warranted. Details will be provided in the SAP.

6.4.1.1. Primary Endpoint

The primary efficacy endpoint is time to first adjudicated On-Trial Relapse. The trial will be considered to have met its primary efficacy objective if a statistically significant difference (e.g., p-value <0.05) is observed between the ravulizumab treatment group and the placebo group for the primary endpoint of the time to first adjudicated On-Trial Relapse. The comparison of the treatment groups for the primary endpoint will use a log-rank test. Hazard ratio and risk reduction will be summarized from a Cox proportional hazards model. Confidence intervals (95%) will be presented for the estimated proportion of patients that are relapse-free at various timepoints (e.g., Week 26, Week 50) based on the complementary log-log transformation. Kaplan-Meier curves for both treatment groups will be produced.

Sensitivity analyses of the primary endpoint will be described in the SAP.

6.4.1.2. Secondary Endpoint(s)

6.4.1.2.1. Adjudicated On-Trial ARR

The adjudicated On-Trial ARR will be presented descriptively showing the ravulizumab treatment group estimate and 95% CI from a Poisson regression model in which the log of time in the study period will be used as the offset variable and historical ARR will be a covariate in the model. This endpoint will be considered to be statistically significant if the upper bound of the 95% CI is <=0.25 relapses per year.

6.4.1.2.2. EuroQoL 5 Dimension (EQ-5D) Index Score and EQ-5D VAS

The change from baseline in the EQ-5D index score to the 6-week post-relapse/End of Primary Treatment Period time point (i.e. for the placebo arm: 6 weeks post-relapse for the patients who have relapses, or Study NCT01892345 end of study (EOS) for patients who did not have relapses; for the ravulizumab arm: the 6 week post-relapse visit for the first observed relapse for the patients who have relapses and the EQ-5D index score from the End of Primary Treatment Period visit for patients who did not have a relapse) will be analyzed using a nonparametric analysis of covariance (ANCOVA) adjusted for baseline EQ-5D index score. Baseline is defined as the last available assessment prior to treatment for all patients regardless of their treatment group.

The changes from baseline to the 6-week post-relapse/EOPT Period time point in EQ-5D VAS will be analyzed as described for the change in EQ-5D index score, using the nonparametric ANCOVA adjusted for baseline EQ-5D VAS.

6.4.1.2.3. Expanded Disability Status Scale (EDSS)

The change from baseline in the EDSS score to the 6-week post-relapse/EOPT Period analysis time point will be calculated as described for the EQ-5D endpoints. For the EDSS, this change from baseline will be categorized into clinically important worsening (no worsening, clinical worsening). This endpoint will be analyzed using a logistic regression model including treatment group and baseline EDSS as a covariate. Details will be provided in the SAP.

6.4.1.2.4. Hauser Ambulation Index (HAI)

The change from baseline in the HAI score to the 6-week post-relapse/EOPT Period analysis time point will be calculated as described for the EQ-5D endpoints. For the HAI, this change from baseline will be categorized into clinically important changes (clinical improvement, stable, clinical worsening). This 3-level endpoint will be analyzed using a proportional odds model including treatment group and baseline HAI as a covariate. Details will be provided in the SAP.

6.4.1.2.5. Accounting for multiple comparisons

A closed testing procedure will be applied to control the type I error for the analyses of the primary and secondary endpoints. If the primary endpoint is statistically significant in favor of ravulizumab, the secondary endpoints will be evaluated according to the following rank order:

1. Adjudicated On-Trial ARR
2. Clinically important changes from baseline in ambulatory function as measured by HAI
3. Change from baseline in EQ-5D index score
4. Change from baseline in EQ-5D VAS score
5. Clinically important worsening from baseline in EDSS score The hypothesis testing will proceed from highest rank (#1) the adjudicated On-Trial ARR to the lowest rank (#5) EDSS score, and if statistical significance is not achieved at an endpoint (p>=0.05 or the upper CI of the ARR is >0.25), then endpoints of lower rank will not be considered to be statistically significant. Confidence intervals and p-values will be presented for all secondary efficacy endpoints for descriptive purposes, regardless of the outcome of the closed testing procedure.

6.4.1.3. Tertiary/Exploratory Endpoint(s)

Summaries and analyses of tertiary and exploratory endpoints will be described in the SAP.

6.4.2. Safety Analyses

All safety data will be summarized using the Safety Set.

6.4.2.1. Analysis of Adverse Events

The analysis and reporting of AEs will be based on treatment-emergent adverse events (TEAEs), defined as AEs with onset on or after the first dose of ravulizumab. The incidence of TEAEs will be summarized by system organ class (SOC) and preferred term, with additional summaries showing severity, relationship to study drug, TEAEs leading to study drug discontinuation, and TEAEs resulting in death. Summaries of TESAEs will also be summarized by SOC and preferred term, with an additional summary showing relationship to study drug. These summaries will be presented by treatment group (ravulizumab, placebo).

6.4.2.2. Analysis of Clinical Laboratory Parameters, Vital Sign Measurements and Electrocardiogram Parameters Laboratory measurements as well as their changes from Baseline at each visit and shift from baseline, if applicable, will be summarized. ECGs, including ECG interpretation heart rate, PR, QRS, QT, and QTc intervals, and vital signs will also be summarized.

6.4.2.3. Other Safety Analyses

The number and percentage of patients in each of the C-SSRS categories as well as shifts from baseline will be presented.

6.4.3. Demographics and Baseline Characteristics

Patient demographic and baseline characteristics will be summarized by treatment group, using the Safety Set. Summary statistics will be presented. No formal hypothesis testing will be performed.

6.4.4. Patient Disposition

The number of patients screened, treated, completing the study, discontinued the study, reasons for discontinuation, and those included in each analysis set will be summarized. Major protocol deviations will be summarized by prespecified deviation categories.

6.4.5. Medical/Surgical History and Neuromyelitis Optica Spectrum Disorder History The medical and surgical history will be summarized by the Medical Dictionary for Regulatory (MedDRA) Activities, Version 21.0, or later by SOC and PT. NMOSD History will also be summarized.

6.4.6. Prior and Concomitant Medications

Any medication taken prior to first dose of study drug will be considered as prior medications; and any medication taken on or after the first dose of study drug will be considered as concomitant medications. Prior and concomitant medications will be summarized for all patients in the Safety Analysis Set, including ISTs for relapse prevention and acute relapse treatment. Medications will be coded using the World Health Organization Drug Dictionary (WHODrug; the most current version available at the time of the analyses).

6.4.7. Pharmacokinetic, Pharmacodynamic, and Anti-Drug Antibody Analyses

Individual serum concentration data for all patients who receive at least 1 dose of ravulizumab and who have evaluable PK data will be used to derive PK parameters for ravulizumab.

Graphs of mean serum concentration-time profiles will be constructed. Graphs of serum concentration-time profiles for individual patients may also be provided. Actual dose administration and sampling times will be used for all calculations. Descriptive statistics will be calculated for serum concentration data at each sampling time, as appropriate. Assessment of population-PK may be considered using data from this study or in combination with data from other studies.

Pharmacodynamic analyses will be performed for all patients who receive at least 1 dose of ravulizumab and who have evaluable PD data.

Descriptive statistics will be presented for all ravulizumab PD endpoints at each sampling time (Section 1.3). The PD effects of ravulizumab will be evaluated by assessing the absolute values and changes and percentage changes from baseline in free C5 serum concentrations over time, as appropriate. Assessments of ravulizumab PK/PD relationships may be explored using data from this study or in combination with data from other studies.

For assessment of immunogenicity, the presence of confirmed positive ADAs will be summarized. Additionally, following confirmation of positive ADAs, samples will be assessed for ADA titer and presence of neutralizing antibodies.

6.5. Interim Analysis

The primary analysis will be conducted when all patients have completed the Primary Treatment Period. This analysis will include all efficacy, safety, and PK/PD study data for regulatory submission purposes and will be the final analysis of the Primary Treatment Period. This analysis will not be considered an interim analysis. Interim analyses that include data collected during the Long-term Extension may be performed to support submission requirements.

6.6. Data Monitoring Committee (DMC)

This study will not include a DMC.

7. Supporting Documentation and Operational Considerations 7.1. Appendix 1: Diagnostic Criteria for Neuromyelitis Optica Spectrum Disorder International Panel for NMO Diagnosis Diagnostic Criteria for NMOSD with AQP4-IgG (Wingerchuk, D. et al., *Neurology*, 85:177-89, 2015)—all 3 criteria below must be met for a diagnosis of NMOSD in this study:

1. At least 1 core clinical characteristic:

Optic neuritis

Acute myelitis

Area postrema syndrome: episode of otherwise unexplained hiccups or nausea and vomiting Acute brainstem syndrome Symptomatic narcolepsy or acute diencephalic clinical syndrome with NMOSD-typical diencephalic MRI lesions Symptomatic cerebral syndrome with NMOSD-typical brain lesions visualized on MRI 2. Positive test for anti-AQP4 Ab using best available detection method (cell-based assay required in this study)

3. Exclusion of alternative diagnosis 7.2. Appendix 2: Expanded Disability Status Scale (EDSS)

The Kurtzke EDSS is a method of quantifying disability in Multiple Sclerosis (MS). The EDSS replaced the previous Disability Status Scales used in MS. The EDSS quantifies disability in 8 Functional Systems (FS) and allows neurologists to assign a Functional System Score (FSS) in each of these. The FS are:

pyramidal cerebellar brainstem sensory bowel and bladder visual cerebral other

EDSS steps 1.0 to 4.5 refer to people with MS who are fully ambulatory; EDSS steps 5.0 to 9.5 are defined by the impairment to ambulation, as shown in FIG. 4.

TABLE 7

| Abbreviations. | |
| --- | --- |
| Abbreviation | Definition |
| Ab | antibody |
| ADA | antidrug antibody |
| AE | adverse event |
| AESI | adverse event of special interest |
| aHUS | atypical hemolytic uremic syndrome |
| ANCOVA | analysis of covariance |
| AQP4 | aquaporin-4 |
| ARR | annualized relapse rate |
| AZA | azathioprine |
| B | baseline (sample) |
| BP | blood pressure |
| C5 | complement component 5 |
| CFR | Code of Federal Regulations |
| CI | Confidence interval |
| CIOMS | Council for international Organizations of Medical Sciences |
| CNS | central nervous system |
| CRF | case report form |
| CSF | cerebrospinal fluid |
| C-SSRS | Columbia-suicide severity rating scale |
| CTCAE | Common Terminology Criteria for Adverse Events |
| D | day |
| DMC | Data Monitoring Committee |
| ECG | electrocardiogram |
| eCRF | electronic case report form |
| ED | early discontinuation |
| EDC | electronic data capture |
| EDSS | expanded disability status scale |
| EOPT | End of Primary Treatment |
| EOS | End of Study |
| EOT | End of Treatment |
| EQ-5D | European Quality of Life Health 5-item questionnaire |
| EQ VAS | European Quality of Life Visual Analog Scale |
| EuroQoL | EuroQoL European Quality of Life |
| FAS | full analysis set |
| FDA | Food and Ding Administration |
| FS | functional system |
| FSS | functional system scores |
| FU | Follow-up |
| GCP | Good Clinical Practice |
| gMG | generalized myasthenia gravis |
| HAI | Hauser Ambulation Index |
| HIPAA | Health Insurance Portability and Accountability Act |
| HIV | human immunodeficiency virus |
| HRT | hormonal replacement therapy |
| ICF | informed consent form |
| ICH | International Conference on Harmonisation |
| IEC | Independent Ethics Committee |
| IgG | immunoglobulin G |
| IL-6 | interleukin 6 |
| IMP | Investigational medicinal product |
| IPND | International Panel for NMO Diagnosis |
| IRB | Institutional Review Board |
| IST | immunosuppressive therapy |
| IV | intravenous |
| IVIg | intravenous immunoglobulin |
| IVMP | intravenous methylprednisolone |
| L | low |
| MAA | marketing authorization application |
| mAb | monoclonal antibody |
| MCV | mean corpuscular volume |
| MedDRA | Medical Dictionary for Regulatory Activities |
| MMF | mycophenolate mofetil |
| MRC | Medical Research Council |
| MRI | magnetic resonance imaging |
| MS | multiple sclerosis |
| MTX | methotrexate |
| N | normal |
| NA | not applicable |
| NfL | neurofilament light chain |
| NMO | neuromyelitis optica |
| NMOSD | neuromyelitis optica spectrum disorder |
| OCT | Ocular Coherence Tomography |
| ON | optic neuritis |
| OSIS | Optic Spinal Impairment Score |
| P | postdose (sample) |
| PD | Pharmacodynamic(s) |

TABLE 7-continued

Abbreviations.

| Abbreviation | Definition |
| --- | --- |
| PE | plasma exchange |
| PI | Principal Investigator |
| PK | Pharmacokinetic(s) |
| PNH | paroxysmal nocturnal hemoglobinuria |
| PP | plasmapheresis |
| PT | primary treatment |
| q2w | every two weeks |
| q8w | every eight weeks |
| QoL | quality of life |
| QT | interval between the start of the Q wave and the end of the T wave in an ECG |
| QTc | corrected QT interval |
| RAC | Relapse Adjudication Committee |
| RBC | red blood cell |
| RD | relapse day |
| RND | ribonucleic acid |
| RR | respiratory rate |
| SAE | serious adverse event |
| SAP | statistical analysis plan |
| SF | short form health survey |
| SoA | schedule of activities |
| SOC | System Organ Class |
| SUSAR | suspected unexpected serious adverse reactions |
| T | Trough |
| TAC | tacrolimus |
| TEAE | treatment-emergent adverse event |
| TESAE | treatment-emergent serious adverse event |
| TFR | Time to First Relapse |
| TM | transverse myelitis |
| UMN | upper motor neuron |
| USPI | United States Prescribing Information |
| VA | visual acuity |
| VAS | visual analogue scale |
| VF | Visual Fields |
| W | week(s) |
| WBC | white blood cell |
| WHODrug | World Health Organization Drug Dictionary |
| WOCBP | woman of child-bearing potential |

```
SEQUENCE SUMMARY
                              SEQ ID NO: 1
GYIFSNYWIQ

SEQ ID NO: 2
EILPGSGSTEYTENFKD

SEQ ID NO: 3
YFFGSSPNWYFDV

SEQ ID NO: 4
GASENIYGALN

SEQ ID NO: 5
GATNLAD

SEQ ID NO: 6
QNVLNTPLT

SEQ ID NO: 7
QVQLVQSGAEVKKPGASVKVSCKASGYIFSNYWIQWVRQAPGQGLEWM

GEILPGSGSTEYTENFKDRVTMTRDTSTSTVYMELSSLRSEDTAVYYC

ARYFFGSSPNWYFDVWGQGTLVTVSS

SEQ ID NO: 8
DIQMTQSPSSLSASVGDRVTITCGASENIYGALNWYQQKPGKAPKLLIYGA

TNLADGVPSRFSGSGSGTDFTLTISSLQPEDFATYYCQNVLNTPLTFGQGT

KVEIK
```

-continued

```
                              SEQ ID NO: 9
ASTKGPSVFPLAPCSRSTSESTAALGCLVKDYFPEPVTVSWNSGALTSGVH

TFPAVLQSSGLYSLSSVVTVPSSNFGTQTYTCNVDHKPSNTKVDKTVERKC

CVECPPCPAPPVAGPSVFLFPPKPKDTLMISRTPEVTCVVVDVSQEDPEVQ

FNWYVDGVEVHNAKTKPREEQFNSTYRVVSVLTVLHQDWLNGKEYKCKVSN

KGLPSSIEKTISKAKGQPREPQVYTLPPSQEEMTKNQVSLTCLVKGFYPSD

IAVEWESNGQPENNYKTTPPVLDSDGSFFLYSRLTVDKSRWQEGNVFSCSV

MHEALHNHYTQKSLSLSLGK

SEQ ID NO: 10
QVQLVQSGAEVKKPGASVKVSCKASGYIFSNYWIQWVRQAPGQGLEWM

GEILPGSGSTEYTENFKDRVTMTRDTSTSTVYMELSSLRSEDTAVYYC

ARYFFGSSPNWYFDVWGQGTLVTVSSASTKGPSVFPLAPCSRSTSEST

AALGCLVKDYFPEPVTVSWNSGALTSGVHTFPAVLQSSGLYSLSSVVT

VPSSNFGTQTYTCNVDHKPSNTKVDKTVERKCCVECPPCPAPPVAGPS

VFLFPPKPKDTLMISRTPEVTCVVVDVSQEDPEVQFNWYVDGVEVHNA

KTKPREEQFNSTYRVVSVLTVLHQDWLNGKEYKCKVSNKGLPSSIEKT

ISKAKGQPREPQVYTLPPSQEEMTKNQVSLTCLVKGFYPSDIAVEWES

NGQPENNYKTTPPVLDSDGSFFLYSRLTVDKSRWQEGNVFSCSVMHEA

LHNHYTQKSLSLSLGK

SEQ ID NO: 11
DIQMTQSPSSLSASVGDRVTITCGASENIYGALNWYQQKPGKAPKLLIYG

ATNLADGVPSRISGSGSGTDFTLTISSLQPEDFATYYCQNVLNTPLTFGQ

GYKVEIKRTVAAPSYFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

SEQ ID NO: 12
QVQLVQSGAEVKKPGASVKVSCKASGHIFSNYWIQWVRQAPGQGLEWM

GEILPGSGHTEYTENFKDRVTMTRDTSTSTVYMELSSLRSEDTAVYYC

ARYFFGSSPNWYFDVWGQGTLVTVSS

SEQ ID NO: 13
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSQEDP

EVQFNWYVDGVEVHNAKTKPREEQFNSTYRVVSVLTVLHQDWLNGKEYKC

KVSNKGLPSSIEKTISKAKGQPREPQVYTLPPSQEEMTKNQVSLTCLVKG

FYPSDIAVEWESNGQPENNYKTTPPVLDSDGSFFLYSRLTVDKSRWQEGN

VFSCSVLHEALHSHYTQKSLSLSLGK

SEQ ID NO: 14
QVQLVQSGAEVKKPGASVKVSCKASGHIFSNYWIQWVRQAPGQGLEWM

GEILPGSGHTEYTENFKDRVTMTRDTSTSTVYMELSSLRSEDTAVYYC

ARYFFGSSPNWYFDVWGQGTLVTVSS ASTKGPSVFPLAPCSRSTSES

TEAALGCLVKDYFPEPVTVSWNSGALTSGVHTFPAVLQSSGLYSLSSV

VTVPSSNFGTQTYTCNVDHKPSNTKVDKTVERKCCVECPPCPAPPVAG

PSFFLFPPKPKDTIMISRTPEVTCVVVDVSQEDPEVQFNWYVDGVEVH
```

NAKTKPREEQFNSTYRVVSVLTVLHQDWLNGKEYKCKVSNKGLPSSIE

KTISKAKGQPREPQVYTLPPSQEEMTKNQVSLTCPVKGFYPSDIAVEW

ESNGQPENNYKTTPPVLDSDGSFFLYSRLTVDKSRWQEGNVFSCSVLH

EALHSHYTQKSLSLSLGK

SEQ ID NO: 15

ASTKGPSVFPLAPCSRSTSESTAALGCLVKDYFPEPVTVSWNSGALTS

GVHTFPAVLQSSGLYSLSSVVTVTSSNFGTQTYTCNVDHKPSNTKVDK

TVERKCCVECPPCPAPPVAGPSVFLFPPKPKDTLYITREPEVTCVVVD

VSHEDPEVQFNWYVDGMEVHNAKTKPREEQFNSTFRVVSVLTVVHQDW

LNGKEYKCKVSNKGLPAPIEKTISKTKGQPREPQVYTLPPSREEMTKN

SQVSLTCLVKGFYPDIAVEWESNGQPENNYKTTPPMLDSDGSFFLYSK

LTVDKSRWQQGNVFSCSVMHEALHNHYTQKSLSLSPGK

SEQ ID NO: 16

QVQLVQSGAEVKKPGASVKVSCKASGYIFSNYWIQWVRQAPGQGLEWM

GEILPGSGSTEYTENFKDRVTMTRDTSTSTVYMELSSLRSEDTAVYYCAR

YFFGSSPNWYFDVWGQGTLVTVSSASTKGPSVFPLAPCSRSTSESTAALG

CLVKDYFPEPVTVSWNSGALTSGVHTFPAVLQSSGLYSLSSVVTVTSSNF

GTQTYTCNVDHKPSNTKVDKTVERKCCVECPPCPAPPVAGPSVFLFPPKP

KDTLYITREPEVTCVVVDVSHEDPEVQFNWYVDGMEVHNAKTKPREEQ

FNSTFRVVSVLTVVHQDWLNGKEYKCKVSNKGLPAPIEKTISKTKGQPRE

PQVYTLPPSREEMTKNQVSLTCLVKGFYPSDIAVEWESNGQPENNYKTTP

PMLDSDGSFFLYSKLTVDKSRWQQGNVFSCSVMHEALHNHYTQKSLSLS

PGK

SEQ ID NO: 17

GASENIYHALN

SEQ ID NO: 18

EILPGSGHTEYTENFKD

SEQ ID NO: 19

GHIFSNYWIQ

SEQ ID NO: 20

QVQLVQSGAEVKKPGASVKVSCKASGHIFSNYWIQWVRQAPGQGLEW

MGEILPGSGHTEYTENFKDRVTMTRDTSTSTVYMELSSLRSEDTAVYYC

ARYFFGSSPNWYFDVWGQGTLVTVSSASTKGPSFFPLAPCSRSTSESTA

ALGCLVKDYFPEPVWSWNSGALTSGVHTFPAVLQSSGLYSLSSVVTVPS

SNFGTQTYTCNVDHKPSNTKVDKTVERKCCVECPPCPAPPVAGPSVFLF

PPKPKDTLMISRTPEVTCVVVDVSQEDPEVQFNWYVDGVEVHNAKTKPR

EEQFNSTYRVVSVLTVLHQDWLNGKEYKCKVSNKGLPSSIEKTISKAKG

QPREPQVYTLPPSQEEMTKNQVSLTCLVKGFYPSDIAVEWESNGQPENN

YKTTPPVLDSDGSFFLYSRLTVDKSRWQEGNVFSCSVMHEALHNHYTGK

SLSLSLGK

SEQ ID NO: 21

SYAIS

SEQ ID NO: 22

GIGPFFGTANYAQKFQG

SEQ ID NO: 23

DTPYEDY

SEQ ID NO: 24

SGDSIPNYYVY

SEQ ID NO: 25

DDSNRPS

SEQ ID NO: 26

QSFDSSLNAEV

SEQ ID NO: 27

QVQLVQSGAEVKKPGSSVKVSCKASGGTFSSYAISVWRQAPGQGLEWMG

GIGPFFGTANYAQKFQGRVTITADESTSTAYMELSSLRSEDTAVYYCAR

DTPYFDYWGQGTLVTVSS

SEQ ID NO: 28

DIELTQPPSVSVAPGQTARISCSGDSIPNYYVYWYQQKPGQAPVLVIYD

DSNRPSGIPERFSGSNSGNTATLTISGTQAEDEADYYCQSFDSSLNAEV

FGGGTKLTVL

SEQ ID NO: 29

NYIS

SEQ ID NO: 30

IIDPDDSYTEYSPSFQG

SEQ ID NO: 31

YEYGGFDI

SEQ ID NO: 32

SGDNIGNSYVH

SEQ ID NO: 33

KDNDRPS

SEQ ID NO: 34

GTYDIESYV

SEQ ID NO: 35

EVQLVQSGAEVKKPGESLKISCKGSGYSFTNYISWVRQMPGKGLEWMGIID

PDDSYTEYSPSFQGQVTISADKSISTAYLQWSSLKASDTAMYYCARYEYGG

FDIWGQGTLVTVSS

SEQ ID NO: 36

SYELTQPPSVSVAPGQTARISCSGDNIGNSYVHWYQQKPGQAPVLVIYKD

NDRPSGIPERFSGSNSGNT ATLTISGTQAEDEADYYCGTYDIESYVFG

GGTKLTV L

SEQ ID NO: 37

SSYVA

SEQ ID NO: 38

AIYTGSGATYKASWAKG

SEQ ID NO: 39

DGGYDYPTHAMHY

SEQ ID NO: 40

QASQNIGSSLA

SEQ ID NO: 41

GASKTHS

SEQ ID NO: 42

QSTKVGSSYGNH

SEQ ID NO: 43

QVQLVESGGGLVQPGGSLRLSCAASGFTSHSSYYVAWVRQAPGKGLEWV

GAIYTGSGATYKASWAKGRFTISKDTSKNQVVLTMTNMDPVDTATYYCA

SDGGYDYPTHAMHYWGQGTLVTVSS

SEQ ID NO: 44

DVVMTQSPSSLSASVGDRVTITCQASQNIGSSLAWYQQKPGQAPRLLIY

GASKTHSGVPSRFSGSGSGTDFTLTISSLQPEDVATYYCQSTKVGSSYG

NHFGGGTKVEIK

SEQ ID NO: 45

QVQLVESGGGLVQPGRSLRLSCAASGFTVHSSYYMAWVRQAPGKGLEW

VGAIFTGSGAEYKAEWAKGRVTISKDTSKNQWLTMTNMDPVDTATYYC

ASDAGYDYPTHAMHYWGQGTLVTVSSASTKGPSVFPLAPSSKSTSGGT

AALGCLVKDYFPEPVTVSWNSGALTSGVHTFPAVLQSSGLYSLSSVVT

VPSSSLGTQTYICNVNHKPSNTKVDKKVEPKSCDKTHTCPPCPAPELR

RGPKVFLFPPKPKDTLMISRTPEVTCVVVDVSHEDPEVKFNWYVDGVE

VHNAKTKPREEQYNSTYRVVSVLTVLHQDWLNGKEYKCKVSNKGLPSS

IEKTISKAKGQPREPQVYTLPPSREEMTKNQVSLTCLVKGFYPSDIAV

EWESNGQPENNYKTTPPVLDSDGSFFLYSKLTVDKSRWQQGNVFSCSV

LHEALHAHYTRKELSLSP

SEQ ID NO: 46

DIQMTQSPSSLSASVGDRVTITCRASQGISSSLAWYQQKPGKAPKLLI

YGASETESGVPSRFSGSGSGTDFTLTISSLQPEDFATYYCQNTKVGSS

YGNTFGGGTKVEIKRTVAAPSVFIFPPSDEQLKSGTASVVCLLNNFYP

REAKVQWKVDNALQSGNSQESVTEQDSKDSTYSLSSTLTLSKADYEKH

KVYACEVTHQGLSSPVTKSFNRGEC

SEQ ID NO: 47

QVQLQESGPGLVKPSETLSLTCTVSGDSVSSSYWTWIRQPPGKGLEWI

GYIYYSGSSNYNPSLKSRATISVDTSKNQFSLKLSSVTAADTAVYYCA

REGNVDTTMIFDYWGQGTLVTVSS

SEQ ID NO: 48

AIQMTQSPSSLSASVGDRVTITCRASQGIRNDLGWYQQKPGKAPKLLI

YAASSLQSGVPSRFAGRGSGTDFTLTISSLQPEDFATYYCLQDFNYPW

TFGQGTKVEIK

SEQ ID NO: 49

QVQLQESGPGLVKPSETLSLTCTVSGDSVSSSYWTWIRQPPGKGLEWIG

YIYYSGSSNYNPSLKSRATISVDTSKNQFSLKLSSVTAADTAVYYCAR

EGNVDTTMIFDYWGQGTLVTVSSASTKGPSVFPLAPCSRSTSESTAAL

GCLVKDYFPEPVTVSWNSGALTSGVIUFPAVLQSSGLYSLSSVVTVPS

SSLGTKTYTCNVDHKPSNTKVDKRVESKYGPPCPPCPAPEFLGGPSVF

LFPPKPKDTLMISRTPEVTCVVVDVSQEDPEVQFNWYVDGVEVHNAKT

KPREEQFNSTYRVVSVLTVLHQDWLNGKEYKCKVSNKGLPSSIEKTIS

KAKGQPREPQVYTLPPSQEEMTKNQVSLTCLVKGFYPSDIAVEWESNG

QPENNYKTTPPVLDSDGSFFLYSRLTVDKSRWQEGNVFSCSVMHEALH

NHYTQKSLSLSLGK

SEQ ID NO: 50

AIQMTQSPSSLSASVGDRVTITCRASQGIRNDLGWYQQKPGKAPKLLI

YAASSLQSGVPSRFAGRGSGTDFTLTISSLQPEDFATYYCLQDFNYPW

TFGQGTKVEIKRTVAAPSVFIFPPSDEQLKSGTASVVCLLNNFYPREA

KVQWKVDNALQSGNSQESVTEQDSKDSTYSLSSTLTLSKADYEKHKVY

ACEVTHQGLSSPVTKSFNRGEC

---

The invention claimed is:

1. A method of treating neuromyelitis optica spectrum disorder (NMOSD) in a human subject in need thereof, comprising administering to the human subject an anti-C5 antibody or antigen binding thereof, wherein the anti-C5 antibody or antigen binding fragment thereof:

comprises CDR1, CDR2 and CDR3 heavy chain sequences as set forth in SEQ ID NOs:19, 18 and 3, respectively, and CDR1, CDR2 and CDR3 light chain sequences as set forth in SEQ ID NOs:4, 5 and 6, respectively, comprises an Fc region comprising the amino acid sequence set forth in SEQ ID NO:13, wherein the amino acid sequence comprises at most four amino acid substitutions in the amino acid sequence set forth in SEQ ID NO:13, and wherein the amino acid substitutions do not include leucine 307 and serine 313; and is administered in an administration cycle comprising:

(a) once on day 1 at a loading dose of:
(i) 2400 mg to a subject weighing ≥40 and <60 kg;
(ii) 2700 mg to a subject weighing ≥60 and <100 kg;
(iii) 3000 mg to a subject weighing ≥100 kg;

(b) on day 15 and every eight weeks thereafter at a maintenance dose of:
(i) 3000 mg to a subject weighing ≥40 and <60 kg;
(ii) 3300 mg to a subject weighing ≥60 and <100 kg;
(iii) 3600 mg to a subject weighing ≥100 kg.

2. The method of claim 1, wherein the anti-C5 antibody or antigen-binding fragment thereof comprises:

(a) a heavy chain variable region depicted in SEQ ID NO:12 and a light chain variable region depicted in SEQ ID NO:8;

(b) a heavy chain constant region depicted in SEQ ID NO:13; or (c) a heavy chain polypeptide comprising the amino acid sequence of SEQ ID NO:14 and a light chain polypeptide comprising the amino acid sequence of SEQ ID NO:11.

3. The method of claim 1, wherein the anti-C5 antibody or antigen-binding fragment thereof binds to human C5 at pH 7.4 and 25° C. with an affinity dissociation constant $(K_D)$ that is in the range 0.1 nM≤$K_D$≤1 nM or binds to human C5 at pH 6.0 and 25° C. with a $K_D$≥10 nM.

4. The method of claim 1, wherein the subject:

(a) is 18 years old or older in age;

(b) is positive for anti-AQP4 antibody;

(c) has at least one attack or relapse in the past 12 months;

(d) has an Expanded Disability Status Scale (EDSS) score≤7;

(e) weighs at least 40 kg; or (f) shows at least one symptom of NMOSD.

5. The method of claim 1, wherein the anti-C5 antibody is administered without additional immunosuppressive therapies (ISTs).

6. The method of claim 1, wherein the anti-C5 antibody is administered with at least one immunosuppressive therapy (IST).

7. The method of claim 6, wherein the at least one IST is selected from the group consisting of a corticosteroid, azathioprine (AZA), mycophenolate mofetil (MMF), methotrexate (MTX), and tacrolimus (TAC).

8. The method of claim 1, wherein the treatment maintains a serum trough concentration of the anti-C5 antibody or antigen binding fragment thereof of 100 µg/mL or greater during the administration cycle.

9. The method of claim 1, wherein the treatment maintains a serum trough concentration of the anti-C5 antibody or antigen binding fragment thereof of 200 µg/mL or greater during the administration cycle.

10. The method of claim 1, wherein the treatment maintains a free C5 concentration of 0.309 to 0.5 µg/mL or lower.

11. The method of claim 1, wherein the anti-C5 antibody or antigen binding fragment thereof is administered at a dose of 3000 mg, 3300 mg or 3600 mg every eight weeks after the administration cycle for up to two years.

12. The method of claim 1, wherein the anti-C5 antibody or antigen binding fragment thereof is formulated for intravenous administration.

13. The method of claim 1, wherein the human subject has not previously been treated with a complement inhibitor.

14. The method of claim 1, wherein the administration cycle is a total of 26 weeks of treatment.

15. The method of claim 1, wherein the treatment results in terminal complement inhibition.

16. The method of claim 1, wherein the subject receives plasma exchange (PE)/plasmapheresis (PP).

17. The method of claim 16, wherein the subject receives a supplemental dose of ravulizumab within 4 hours after PE/PP is completed, wherein the supplemental dose is between 1200-1800 mg of anti-C5 antibody.

18. The method of claim 1, wherein the human subject experiences a clinically meaningful improvement in one or more clinical markers for NMOSD progression after administration of ravulizumab.

19. The method of claim 18, wherein clinical markers for NMOSD progression are selected from a group consisting of time to first adjudicated on-trial relapse and relapse risk reduction, adjudicated On-Trial ARR, EDSS score, EQ-5D, SF-36, HAI and OSIS.

20. The method of claim 1, wherein the anti-C5 antibody is ravulizumab.

* * * * *

SEQUENCE LISTING

<160> NUMBER OF SEQ ID NOS: 50

<210> SEQ ID NO 1
<211> LENGTH: 10
<212> TYPE: PRT
<213> ORGANISM: Artificial Sequence
<220> FEATURE:
<223> OTHER INFORMATION: Heavy chain CDR sequence 1

<400> SEQUENCE: 1

Gly Tyr Ile Phe Ser Asn Tyr Trp Ile Gln
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Heavy chain CDR sequence 2

<400> SEQUENCE: 2

-continued

```
Glu Ile Leu Pro Gly Ser Gly Ser Thr Glu Tyr Thr Glu Asn Phe Lys
1               5                   10                  15

Asp

<210> SEQ ID NO 3
<211> LENGTH: 13
<212> TYPE: PRT
<213> ORGANISM: Artificial Sequence
<220> FEATURE:
<223> OTHER INFORMATION: Heavy chain CDR sequence 3

<400> SEQUENCE: 3

Tyr Phe Phe Gly Ser Ser Pro Asn Trp Tyr Phe Asp Val
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Light chain CDR sequence 1

<400> SEQUENCE: 4

Gly Ala Ser Glu Asn Ile Tyr Gly Ala Leu Asn
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Light chain CDR sequence 2

<400> SEQUENCE: 5

Gly Ala Thr Asn Leu Ala Asp
1               5

<210> SEQ ID NO 6
<211> LENGTH: 9
<212> TYPE: PRT
<213> ORGANISM: Artificial Sequence
<220> FEATURE:
<223> OTHER INFORMATION: Light chain CDR sequence 3

<400> SEQUENCE: 6

Gln Asn Val Leu Asn Thr Pro Leu Thr
1               5

<210> SEQ ID NO 7
<211> LENGTH: 122
<212> TYPE: PRT
<213> ORGANISM: Artificial Sequence
<220> FEATURE:
<223> OTHER INFORMATION: Heavy chain variable region sequence

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly Ser Thr Glu Tyr Thr Glu Asn Phe
    50                  55                  60
```

-continued

```
Lys Asp Arg Val Thr Met Thr Arg Asp Thr Ser Thr Ser Thr Val Tyr
65              70              75              80

Met Glu Leu Ser Ser Leu Arg Ser Glu Asp Thr Ala Val Tyr Tyr Cys
                85              90              95

Ala Arg Tyr Phe Phe Gly Ser Ser Pro Asn Trp Tyr Phe Asp Val Trp
            100             105             110

Gly Gln Gly Thr Leu Val Thr Val Ser Ser
            115             120
```

```
<210> SEQ ID NO 8
<211> LENGTH: 107
<212> TYPE: PRT
<213> ORGANISM: Artificial Sequence
<220> FEATURE:
<223> OTHER INFORMATION: Light chain variable region sequence

<400> SEQUENCE: 8

Asp Ile Gln Met Thr Gln Ser Pro Ser Ser Leu Ser Ala Ser Val Gly
1               5               10              15

Asp Arg Val Thr Ile Thr Cys Gly Ala Ser Glu Asn Ile Tyr Gly Ala
            20              25              30

Leu Asn Trp Tyr Gln Gln Lys Pro Gly Lys Ala Pro Lys Leu Leu Ile
            35              40              45

Tyr Gly Ala Thr Asn Leu Ala Asp Gly Val Pro Ser Arg Phe Ser Gly
        50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Asn Val Leu Asn Thr Pro Leu
                85              90              95

Thr Phe Gly Gln Gly Thr Lys Val Glu Ile Lys
            100             105
```

```
<210> SEQ ID NO 9
<211> LENGTH: 326
<212> TYPE: PRT
<213> ORGANISM: Artificial Sequence
<220> FEATURE:
<223> OTHER INFORMATION: Heavy chain constant region sequence

<400> SEQUENCE: 9

Ala Ser Thr Lys Gly Pro Ser Val Phe Pro Leu Ala Pro Cys Ser Arg
1               5               10              15

Ser Thr Ser Glu Ser Thr Ala Ala Leu Gly Cys Leu Val Lys Asp Tyr
            20              25              30

Phe Pro Glu Pro Val Thr Val Ser Trp Asn Ser Gly Ala Leu Thr Ser
            35              40              45

Gly Val His Thr Phe Pro Ala Val Leu Gln Ser Ser Gly Leu Tyr Ser
        50              55              60

Leu Ser Ser Val Val Thr Val Pro Ser Ser Asn Phe Gly Thr Gln Thr
65              70              75              80

Tyr Thr Cys Asn Val Asp His Lys Pro Ser Asn Thr Lys Val Asp Lys
                85              90              95

Thr Val Glu Arg Lys Cys Cys Val Glu Cys Pro Pro Cys Pro Ala Pro
            100             105             110

Pro Val Ala Gly Pro Ser Val Phe Leu Phe Pro Pro Lys Pro Lys Asp
            115             120             125

Thr Leu Met Ile Ser Arg Thr Pro Glu Val Thr Cys Val Val Val Asp
        130             135             140
```

-continued

```
Val Ser Gln Glu Asp Pro Glu Val Gln Phe Asn Trp Tyr Val Asp Gly
145             150             155             160

Val Glu Val His Asn Ala Lys Thr Lys Pro Arg Glu Glu Gln Phe Asn
                165             170             175

Ser Thr Tyr Arg Val Val Ser Val Leu Thr Val Leu His Gln Asp Trp
            180             185             190

Leu Asn Gly Lys Glu Tyr Lys Cys Lys Val Ser Asn Lys Gly Leu Pro
            195             200             205

Ser Ser Ile Glu Lys Thr Ile Ser Lys Ala Lys Gly Gln Pro Arg Glu
        210             215             220

Pro Gln Val Tyr Thr Leu Pro Pro Ser Gln Glu Glu Met Thr Lys Asn
225             230             235             240

Gln Val Ser Leu Thr Cys Leu Val Lys Gly Phe Tyr Pro Ser Asp Ile
                245             250             255

Ala Val Glu Trp Glu Ser Asn Gly Gln Pro Glu Asn Asn Tyr Lys Thr
            260             265             270

Thr Pro Pro Val Leu Asp Ser Asp Gly Ser Phe Phe Leu Tyr Ser Arg
        275             280             285

Leu Thr Val Asp Lys Ser Arg Trp Gln Glu Gly Asn Val Phe Ser Cys
        290             295             300

Ser Val Met His Glu Ala Leu His Asn His Tyr Thr Gln Lys Ser Leu
305             310             315             320

Ser Leu Ser Leu Gly Lys
                325
```

```
<210> SEQ ID NO 10
<211> LENGTH: 448
<212> TYPE: PRT
<213> ORGANISM: Artificial Sequence
<220> FEATURE:
<223> OTHER INFORMATION: Heavy chain sequence

<400> SEQUENCE: 10

Gln Val Gln Leu Val Gln Ser Gly Ala Glu Val Lys Lys Pro Gly Ala
1               5               10              15

Ser Val Lys Val Ser Cys Lys Ala Ser Gly Tyr Ile Phe Ser Asn Tyr
                20              25              30

Trp Ile Gln Trp Val Arg Gln Ala Pro Gly Gln Gly Leu Glu Trp Met
            35              40              45

Gly Glu Ile Leu Pro Gly Ser Gly Ser Thr Glu Tyr Thr Glu Asn Phe
        50              55              60

Lys Asp Arg Val Thr Met Thr Arg Asp Thr Ser Thr Ser Thr Val Tyr
65              70              75              80

Met Glu Leu Ser Ser Leu Arg Ser Glu Asp Thr Ala Val Tyr Tyr Cys
                85              90              95

Ala Arg Tyr Phe Phe Gly Ser Ser Pro Asn Trp Tyr Phe Asp Val Trp
            100             105             110

Gly Gln Gly Thr Leu Val Thr Val Ser Ser Ala Ser Thr Lys Gly Pro
            115             120             125

Ser Val Phe Pro Leu Ala Pro Cys Ser Arg Ser Thr Ser Glu Ser Thr
        130             135             140

Ala Ala Leu Gly Cys Leu Val Lys Asp Tyr Phe Pro Glu Pro Val Thr
145             150             155             160

Val Ser Trp Asn Ser Gly Ala Leu Thr Ser Gly Val His Thr Phe Pro
                165             170             175
```

-continued

```
Ala Val Leu Gln Ser Ser Gly Leu Tyr Ser Leu Ser Ser Val Val Thr
              180                 185                 190

Val Pro Ser Ser Asn Phe Gly Thr Gln Thr Tyr Thr Cys Asn Val Asp
              195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
              245                 250                 255

Thr Pro Glu Val Thr Cys Val Val Val Asp Val Ser Gln Glu Asp Pro
              260                 265                 270

Glu Val Gln Phe Asn Trp Tyr Val Asp Gly Val Glu Val His Asn Ala
              275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
              325                 330                 335

Ile Ser Lys Ala Lys Gly Gln Pro Arg Glu Pro Gln Val Tyr Thr Leu
              340                 345                 350

Pro Pro Ser Gln Glu Glu Met Thr Lys Asn Gln Val Ser Leu Thr Cys
              355                 360                 365

Leu Val Lys Gly Phe Tyr Pro Ser Asp Ile Ala Val Glu Trp Glu Ser
              370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
              405                 410                 415

Arg Trp Gln Glu Gly Asn Val Phe Ser Cys Ser Val Met His Glu Ala
              420                 425                 430

Leu His Asn His Tyr Thr Gln Lys Ser Leu Ser Leu Ser Leu Gly Lys
              435                 440                 445
```

```
<210> SEQ ID NO 11
<211> LENGTH: 214
<212> TYPE: PRT
<213> ORGANISM: Artificial Sequence
<220> FEATURE:
<223> OTHER INFORMATION: Light chain sequence

<400> SEQUENCE: 11
```

```
Asp Ile Gln Met Thr Gln Ser Pro Ser Ser Leu Ser Ala Ser Val Gly
1                 5                  10                 15

Asp Arg Val Thr Ile Thr Cys Gly Ala Ser Glu Asn Ile Tyr Gly Ala
              20                 25                 30

Leu Asn Trp Tyr Gln Gln Lys Pro Gly Lys Ala Pro Lys Leu Leu Ile
              35                 40                 45

Tyr Gly Ala Thr Asn Leu Ala Asp Gly Val Pro Ser Arg Phe Ser Gly
    50                 55                 60

Ser Gly Ser Gly Thr Asp Phe Thr Leu Thr Ile Ser Ser Leu Gln Pro
65                 70                 75                 80

Glu Asp Phe Ala Thr Tyr Tyr Cys Gln Asn Val Leu Asn Thr Pro Leu
              85                 90                 95
```

-continued

```
Thr Phe Gly Gln Gly Thr Lys Val Glu Ile Lys Arg Thr Val Ala Ala
            100                 105             110

Pro Ser Val Phe Ile Phe Pro Pro Ser Asp Glu Gln Leu Lys Ser Gly
            115                 120             125

Thr Ala Ser Val Val Cys Leu Leu Asn Asn Phe Tyr Pro Arg Glu Ala
            130                 135             140

Lys Val Gln Trp Lys Val Asp Asn Ala Leu Gln Ser Gly Asn Ser Gln
145                 150             155                 160

Glu Ser Val Thr Glu Gln Asp Ser Lys Asp Ser Thr Tyr Ser Leu Ser
                165             170             175

Ser Thr Leu Thr Leu Ser Lys Ala Asp Tyr Glu Lys His Lys Val Tyr
                180             185             190

Ala Cys Glu Val Thr His Gln Gly Leu Ser Ser Pro Val Thr Lys Ser
            195                 200             205

Phe Asn Arg Gly Glu Cys
    210
```

```
<210> SEQ ID NO 12
<211> LENGTH: 122
<212> TYPE: PRT
<213> ORGANISM: Artificial Sequence
<220> FEATURE:
<223> OTHER INFORMATION: Heavy chain variable region sequence

<400> SEQUENCE: 12

Gln Val Gln Leu Val Gln Ser Gly Ala Glu Val Lys Lys Pro Gly Ala
1               5               10              15

Ser Val Lys Val Ser Cys Lys Ala Ser Gly His Ile Phe Ser Asn Tyr
            20              25              30

Trp Ile Gln Trp Val Arg Gln Ala Pro Gly Gln Gly Leu Glu Trp Met
            35              40              45

Gly Glu Ile Leu Pro Gly Ser Gly His Thr Glu Tyr Thr Glu Asn Phe
    50              55              60

Lys Asp Arg Val Thr Met Thr Arg Asp Thr Ser Thr Ser Thr Val Tyr
65              70              75              80

Met Glu Leu Ser Ser Leu Arg Ser Glu Asp Thr Ala Val Tyr Tyr Cys
                85              90              95

Ala Arg Tyr Phe Phe Gly Ser Ser Pro Asn Trp Tyr Phe Asp Val Trp
            100                 105             110

Gly Gln Gly Thr Leu Val Thr Val Ser Ser
            115                 120
```

```
<210> SEQ ID NO 13
<211> LENGTH: 326
<212> TYPE: PRT
<213> ORGANISM: Artificial Sequence
<220> FEATURE:
<223> OTHER INFORMATION: Heavy chain constant region sequence

<400> SEQUENCE: 13

Ala Ser Thr Lys Gly Pro Ser Val Phe Pro Leu Ala Pro Cys Ser Arg
1               5               10              15

Ser Thr Ser Glu Ser Thr Ala Ala Leu Gly Cys Leu Val Lys Asp Tyr
            20              25              30

Phe Pro Glu Pro Val Thr Val Ser Trp Asn Ser Gly Ala Leu Thr Ser
            35              40              45

Gly Val His Thr Phe Pro Ala Val Leu Gln Ser Ser Gly Leu Tyr Ser
```

```
              50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
            130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
                180                 185                 190

Leu Asn Gly Lys Glu Tyr Lys Cys Lys Val Ser Asn Lys Gly Leu Pro
            195                 200                 205

Ser Ser Ile Glu Lys Thr Ile Ser Lys Ala Lys Gly Gln Pro Arg Glu
        210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
                260                 265                 270

Thr Pro Pro Val Leu Asp Ser Asp Gly Ser Phe Phe Leu Tyr Ser Arg
                275                 280                 285

Leu Thr Val Asp Lys Ser Arg Trp Gln Glu Gly Asn Val Phe Ser Cys
            290                 295                 300

Ser Val Leu His Glu Ala Leu His Ser His Tyr Thr Gln Lys Ser Leu
305                 310                 315                 320

Ser Leu Ser Leu Gly Lys
                325
```

```
<210> SEQ ID NO 14
<211> LENGTH: 448
<212> TYPE: PRT
<213> ORGANISM: Artificial Sequence
<220> FEATURE:
<223> OTHER INFORMATION: Heavy chain sequence

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Ser Asn Tyr
                20                  25                  30

Trp Ile Gln Trp Val Arg Gln Ala Pro Gly Gln Gly Leu Glu Trp Met
            35                  40                  45

Gly Glu Ile Leu Pro Gly Ser Gly His Thr Glu Tyr Thr Glu Asn Phe
        50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
```

-continued

```
                    85              90              95

Ala Arg Tyr Phe Phe Gly Ser Ser Pro Asn Trp Tyr Phe Asp Val Trp
            100             105             110

Gly Gln Gly Thr Leu Val Thr Val Ser Ser Ala Ser Thr Lys Gly Pro
            115             120             125

Ser Val Phe Pro Leu Ala Pro Cys Ser Arg Ser Thr Ser Glu Ser Thr
            130             135             140

Ala Ala Leu Gly Cys Leu Val Lys Asp Tyr Phe Pro Glu Pro Val Thr
145             150             155             160

Val Ser Trp Asn Ser Gly Ala Leu Thr Ser Gly Val His Thr Phe Pro
                165             170             175

Ala Val Leu Gln Ser Ser Gly Leu Tyr Ser Leu Ser Ser Val Val Thr
                180             185             190

Val Pro Ser Ser Asn Phe Gly Thr Gln Thr Tyr Thr Cys Asn Val Asp
                195             200             205

His Lys Pro Ser Asn Thr Lys Val Asp Lys Thr Val Glu Arg Lys Cys
            210             215             220

Cys Val Glu Cys Pro Pro Cys Pro Ala Pro Pro Val Ala Gly Pro Ser
225             230             235             240

Val Phe Leu Phe Pro Pro Lys Pro Lys Asp Thr Leu Met Ile Ser Arg
                245             250             255

Thr Pro Glu Val Thr Cys Val Val Val Asp Val Ser Gln Glu Asp Pro
                260             265             270

Glu Val Gln Phe Asn Trp Tyr Val Asp Gly Val Glu Val His Asn Ala
            275             280             285

Lys Thr Lys Pro Arg Glu Glu Gln Phe Asn Ser Thr Tyr Arg Val Val
            290             295             300

Ser Val Leu Thr Val Leu His Gln Asp Trp Leu Asn Gly Lys Glu Tyr
305             310             315             320

Lys Cys Lys Val Ser Asn Lys Gly Leu Pro Ser Ser Ile Glu Lys Thr
                325             330             335

Ile Ser Lys Ala Lys Gly Gln Pro Arg Glu Pro Gln Val Tyr Thr Leu
                340             345             350

Pro Pro Ser Gln Glu Glu Met Thr Lys Asn Gln Val Ser Leu Thr Cys
                355             360             365

Leu Val Lys Gly Phe Tyr Pro Ser Asp Ile Ala Val Glu Trp Glu Ser
            370             375             380

Asn Gly Gln Pro Glu Asn Asn Tyr Lys Thr Thr Pro Pro Val Leu Asp
385             390             395             400

Ser Asp Gly Ser Phe Phe Leu Tyr Ser Arg Leu Thr Val Asp Lys Ser
                405             410             415

Arg Trp Gln Glu Gly Asn Val Phe Ser Cys Ser Val Leu His Glu Ala
            420             425             430

Leu His Ser His Tyr Thr Gln Lys Ser Leu Ser Leu Ser Leu Gly Lys
            435             440             445
```

```
<210> SEQ ID NO 15
<211> LENGTH: 326
<212> TYPE: PRT
<213> ORGANISM: Artificial Sequence
<220> FEATURE:
<223> OTHER INFORMATION: Heavy chain constant region sequence

<400> SEQUENCE: 15

Ala Ser Thr Lys Gly Pro Ser Val Phe Pro Leu Ala Pro Cys Ser Arg
```

```
1               5                    10                   15

Ser Thr Ser Glu Ser Thr Ala Ala Leu Gly Cys Leu Val Lys Asp Tyr
             20                    25                   30

Phe Pro Glu Pro Val Thr Val Ser Trp Asn Ser Gly Ala Leu Thr Ser
             35                    40                   45

Gly Val His Thr Phe Pro Ala Val Leu Gln Ser Ser Gly Leu Tyr Ser
       50                    55                   60

Leu Ser Ser Val Val Thr Val Thr Ser Ser Asn Phe Gly Thr Gln Thr
65                    70                   75                   80

Tyr Thr Cys Asn Val Asp His Lys Pro Ser Asn Thr Lys Val Asp Lys
                 85                   90                   95

Thr Val Glu Arg Lys Cys Cys Val Glu Cys Pro Pro Cys Pro Ala Pro
                100                  105                  110

Pro Val Ala Gly Pro Ser Val Phe Leu Phe Pro Pro Lys Pro Lys Asp
                115                  120                  125

Thr Leu Tyr Ile Thr Arg Glu Pro Glu Val Thr Cys Val Val Val Asp
       130                  135                  140

Val Ser His Glu Asp Pro Glu Val Gln Phe Asn Trp Tyr Val Asp Gly
145                  150                  155                  160

Met Glu Val His Asn Ala Lys Thr Lys Pro Arg Glu Glu Gln Phe Asn
                165                  170                  175

Ser Thr Phe Arg Val Val Ser Val Leu Thr Val Val His Gln Asp Trp
                180                  185                  190

Leu Asn Gly Lys Glu Tyr Lys Cys Lys Val Ser Asn Lys Gly Leu Pro
                195                  200                  205

Ala Pro Ile Glu Lys Thr Ile Ser Lys Thr Lys Gly Gln Pro Arg Glu
       210                  215                  220

Pro Gln Val Tyr Thr Leu Pro Pro Ser Arg Glu Glu Met Thr Lys Asn
225                  230                  235                  240

Gln Val Ser Leu Thr Cys Leu Val Lys Gly Phe Tyr Pro Ser Asp Ile
                245                  250                  255

Ala Val Glu Trp Glu Ser Asn Gly Gln Pro Glu Asn Asn Tyr Lys Thr
                260                  265                  270

Thr Pro Pro Met Leu Asp Ser Asp Gly Ser Phe Phe Leu Tyr Ser Lys
                275                  280                  285

Leu Thr Val Asp Lys Ser Arg Trp Gln Gln Gly Asn Val Phe Ser Cys
       290                  295                  300

Ser Val Met His Glu Ala Leu His Asn His Tyr Thr Gln Lys Ser Leu
305                  310                  315                  320

Ser Leu Ser Pro Gly Lys
             325
```

<210> SEQ ID NO 16
<211> LENGTH: 448
<212> TYPE: PRT
<213> ORGANISM: Artificial Sequence
<220> FEATURE:
<223> OTHER INFORMATION: Heavy chain sequence

<400> SEQUENCE: 16

```
Gln Val Gln Leu Val Gln Ser Gly Ala Glu Val Lys Lys Pro Gly Ala
1               5                    10                   15

Ser Val Lys Val Ser Cys Lys Ala Ser Gly Tyr Ile Phe Ser Asn Tyr
             20                    25                   30

Trp Ile Gln Trp Val Arg Gln Ala Pro Gly Gln Gly Leu Glu Trp Met
```

-continued

```
              35                    40                    45
Gly Glu Ile Leu Pro Gly Ser Gly Ser Thr Glu Tyr Thr Glu Asn Phe
    50                  55                  60
Lys Asp Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Tyr Phe Phe Gly Ser Ser Pro Asn Trp Tyr Phe Asp Val Trp
            100                 105                 110
Gly Gln Gly Thr Leu Val Thr Val Ser Ser Ala Ser Thr Lys Gly Pro
            115                 120                 125
Ser Val Phe Pro Leu Ala Pro Cys Ser Arg Ser Thr Ser Glu Ser Thr
    130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Thr Ser Ser Asn Phe Gly Thr Gln Thr Tyr Thr Cys Asn Val Asp
            195                 200                 205
His Lys Pro Ser Asn Thr Lys Val Asp Lys Thr Val Glu Arg Lys Cys
    210                 215                 220
Cys Val Glu Cys Pro Pro Cys Pro Ala Pro Pro Val Ala Gly Pro Ser
225                 230                 235                 240
Val Phe Leu Phe Pro Pro Lys Pro Lys Asp Thr Leu Tyr Ile Thr Arg
                245                 250                 255
Glu Pro Glu Val Thr Cys Val Val Val Asp Val Ser His Glu Asp Pro
            260                 265                 270
Glu Val Gln Phe Asn Trp Tyr Val Asp Gly Met Glu Val His Asn Ala
            275                 280                 285
Lys Thr Lys Pro Arg Glu Glu Gln Phe Asn Ser Thr Phe Arg Val Val
    290                 295                 300
Ser Val Leu Thr Val Val His Gln Asp Trp Leu Asn Gly Lys Glu Tyr
305                 310                 315                 320
Lys Cys Lys Val Ser Asn Lys Gly Leu Pro Ala Pro Ile Glu Lys Thr
                325                 330                 335
Ile Ser Lys Thr Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
            355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Met Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
            435                 440                 445
```

<210> SEQ ID NO 17

-continued

```
<211> LENGTH: 11
<212> TYPE: PRT
<213> ORGANISM: Artificial Sequence
<220> FEATURE:
<223> OTHER INFORMATION: Light chain CDR sequence 1

<400> SEQUENCE: 17

Gly Ala Ser Glu Asn Ile Tyr His Ala Leu Asn
1               5                   10

<210> SEQ ID NO 18
<211> LENGTH: 17
<212> TYPE: PRT
<213> ORGANISM: Artificial Sequence
<220> FEATURE:
<223> OTHER INFORMATION: Heavy chain CDR sequence 2

<400> SEQUENCE: 18

Glu Ile Leu Pro Gly Ser Gly His Thr Glu Tyr Thr Glu Asn Phe Lys
1               5                   10                  15

Asp

<210> SEQ ID NO 19
<211> LENGTH: 10
<212> TYPE: PRT
<213> ORGANISM: Artificial Sequence
<220> FEATURE:
<223> OTHER INFORMATION: Heavy chain CDR sequence 1

<400> SEQUENCE: 19

Gly His Ile Phe Ser Asn Tyr Trp Ile Gln
1               5                   10

<210> SEQ ID NO 20
<211> LENGTH: 448
<212> TYPE: PRT
<213> ORGANISM: Artificial Sequence
<220> FEATURE:
<223> OTHER INFORMATION: Heavy chain sequence

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly His Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
                100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160
```

```
Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
            195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Val Ala Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
            405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445
```

```
<210> SEQ ID NO 21
<211> LENGTH: 5
<212> TYPE: PRT
<213> ORGANISM: Artificial Sequence
<220> FEATURE:
<223> OTHER INFORMATION: Heavy chain CDR sequence 1

<400> SEQUENCE: 21

Ser Tyr Ala Ile Ser
1               5

<210> SEQ ID NO 22
<211> LENGTH: 17
<212> TYPE: PRT
<213> ORGANISM: Artificial Sequence
<220> FEATURE:
<223> OTHER INFORMATION: Heavy chain CDR sequence 2

<400> SEQUENCE: 22

Gly Ile Gly Pro Phe Phe Gly Thr Ala Asn Tyr Ala Gln Lys Phe Gln
1               5                   10                  15
```

-continued

Gly

```
<210> SEQ ID NO 23
<211> LENGTH: 7
<212> TYPE: PRT
<213> ORGANISM: Artificial Sequence
<220> FEATURE:
<223> OTHER INFORMATION: Heavy chain CDR sequence 3

<400> SEQUENCE: 23

Asp Thr Pro Tyr Phe Asp Tyr
1               5

<210> SEQ ID NO 24
<211> LENGTH: 11
<212> TYPE: PRT
<213> ORGANISM: Artificial Sequence
<220> FEATURE:
<223> OTHER INFORMATION: Light chain CDR sequence 1

<400> SEQUENCE: 24

Ser Gly Asp Ser Ile Pro Asn Tyr Tyr Val Tyr
1               5                   10

<210> SEQ ID NO 25
<211> LENGTH: 7
<212> TYPE: PRT
<213> ORGANISM: Artificial Sequence
<220> FEATURE:
<223> OTHER INFORMATION: Light chain CDR sequence 2

<400> SEQUENCE: 25

Asp Asp Ser Asn Arg Pro Ser
1               5

<210> SEQ ID NO 26
<211> LENGTH: 11
<212> TYPE: PRT
<213> ORGANISM: Artificial Sequence
<220> FEATURE:
<223> OTHER INFORMATION: Light chain CDR sequence 3

<400> SEQUENCE: 26

Gln Ser Phe Asp Ser Ser Leu Asn Ala Glu Val
1               5                   10

<210> SEQ ID NO 27
<211> LENGTH: 116
<212> TYPE: PRT
<213> ORGANISM: Artificial Sequence
<220> FEATURE:
<223> OTHER INFORMATION: Heavy chain variable region sequence

<400> SEQUENCE: 27

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Val Trp Arg Gln Ala Pro Gly Gln Gly Leu Glu Trp Met
        35                  40                  45

Gly Gly Ile Gly Pro Phe Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80
```

```
Met Glu Leu Ser Ser Leu Arg Ser Glu Asp Thr Ala Val Tyr Tyr Cys
                    85                  90                  95

Ala Arg Asp Thr Pro Tyr Phe Asp Tyr Trp Gly Gln Gly Thr Leu Val
                100                 105                 110

Thr Val Ser Ser
        115

<210> SEQ ID NO 28
<211> LENGTH: 108
<212> TYPE: PRT
<213> ORGANISM: Artificial Sequence
<220> FEATURE:
<223> OTHER INFORMATION: Light chain variable region sequence

<400> SEQUENCE: 28

Asp Ile Glu Leu Thr Gln Pro Pro Ser Val Ser Val Ala Pro Gly Gln
1               5                   10                  15

Thr Ala Arg Ile Ser Cys Ser Gly Asp Ser Ile Pro Asn Tyr Tyr Val
                20                  25                  30

Tyr Trp Tyr Gln Gln Lys Pro Gly Gln Ala Pro Val Leu Val Ile Tyr
            35                  40                  45

Asp Asp Ser Asn Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Phe Asp Ser Ser Leu Asn Ala
                85                  90                  95

Glu Val Phe Gly Gly Gly Thr Lys Leu Thr Val Leu
                100                 105

<210> SEQ ID NO 29
<211> LENGTH: 4
<212> TYPE: PRT
<213> ORGANISM: Artificial Sequence
<220> FEATURE:
<223> OTHER INFORMATION: Heavy chain CDR sequence 1

<400> SEQUENCE: 29

Asn Tyr Ile Ser
1

<210> SEQ ID NO 30
<211> LENGTH: 17
<212> TYPE: PRT
<213> ORGANISM: Artificial Sequence
<220> FEATURE:
<223> OTHER INFORMATION: Heavy chain CDR sequence 2

<400> SEQUENCE: 30

Ile Ile Asp Pro Asp Asp Ser Tyr Thr Glu Tyr Ser Pro Ser Phe Gln
1               5                   10                  15

Gly

<210> SEQ ID NO 31
<211> LENGTH: 8
<212> TYPE: PRT
<213> ORGANISM: Artificial Sequence
<220> FEATURE:
<223> OTHER INFORMATION: Heavy chain CDR sequence 3

<400> SEQUENCE: 31
```

-continued

```
Tyr Glu Tyr Gly Gly Phe Asp Ile
1               5

<210> SEQ ID NO 32
<211> LENGTH: 11
<212> TYPE: PRT
<213> ORGANISM: Artificial Sequence
<220> FEATURE:
<223> OTHER INFORMATION: Light chain CDR sequence 1

<400> SEQUENCE: 32

Ser Gly Asp Asn Ile Gly Asn Ser Tyr Val His
1               5                   10

<210> SEQ ID NO 33
<211> LENGTH: 7
<212> TYPE: PRT
<213> ORGANISM: Artificial Sequence
<220> FEATURE:
<223> OTHER INFORMATION: Light chain CDR sequence 2

<400> SEQUENCE: 33

Lys Asp Asn Asp Arg Pro Ser
1               5

<210> SEQ ID NO 34
<211> LENGTH: 9
<212> TYPE: PRT
<213> ORGANISM: Artificial Sequence
<220> FEATURE:
<223> OTHER INFORMATION: Light chain CDR sequence 3

<400> SEQUENCE: 34

Gly Thr Tyr Asp Ile Glu Ser Tyr Val
1               5

<210> SEQ ID NO 35
<211> LENGTH: 116
<212> TYPE: PRT
<213> ORGANISM: Artificial Sequence
<220> FEATURE:
<223> OTHER INFORMATION: Heavy chain variable region sequence

<400> SEQUENCE: 35

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Ile Ser Trp Val Arg Gln Met Pro Gly Lys Gly Leu Glu Trp Met Gly
        35                  40                  45

Ile Ile Asp Pro Asp Asp Ser Tyr Thr Glu Tyr Ser Pro Ser Phe Gln
    50                  55                  60

Gly Gln Val Thr Ile Ser Ala Asp Lys Ser Ile Ser Thr Ala Tyr Leu
65                  70                  75                  80

Gln Trp Ser Ser Leu Lys Ala Ser Asp Thr Ala Met Tyr Tyr Cys Ala
                85                  90                  95

Arg Tyr Glu Tyr Gly Gly Phe Asp Ile Trp Gly Gln Gly Thr Leu Val
            100                 105                 110

Thr Val Ser Ser
        115

<210> SEQ ID NO 36
<211> LENGTH: 106
```

```
<212> TYPE: PRT
<213> ORGANISM: Artificial Sequence
<220> FEATURE:
<223> OTHER INFORMATION: Light chain variable region sequence

<400> SEQUENCE: 36

Ser Tyr Glu Leu Thr Gln Pro Pro Ser Val Ser Val Ala Pro Gly Gln
1               5                   10                  15

Thr Ala Arg Ile Ser Cys Ser Gly Asp Asn Ile Gly Asn Ser Tyr Val
            20                  25                  30

His Trp Tyr Gln Gln Lys Pro Gly Gln Ala Pro Val Leu Val Ile Tyr
        35                  40                  45

Lys Asp Asn Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gly Thr Tyr Asp Ile Glu Ser Tyr Val
                85                  90                  95

Phe Gly Gly Gly Thr Lys Leu Thr Val Leu
            100                 105

<210> SEQ ID NO 37
<211> LENGTH: 6
<212> TYPE: PRT
<213> ORGANISM: Artificial Sequence
<220> FEATURE:
<223> OTHER INFORMATION: Artificial sequence

<400> SEQUENCE: 37

Ser Ser Tyr Tyr Val Ala
1               5

<210> SEQ ID NO 38
<211> LENGTH: 17
<212> TYPE: PRT
<213> ORGANISM: Artificial Sequence
<220> FEATURE:
<223> OTHER INFORMATION: Artificial sequence

<400> SEQUENCE: 38

Ala Ile Tyr Thr Gly Ser Gly Ala Thr Tyr Lys Ala Ser Trp Ala Lys
1               5                   10                  15

Gly

<210> SEQ ID NO 39
<211> LENGTH: 13
<212> TYPE: PRT
<213> ORGANISM: Artificial Sequence
<220> FEATURE:
<223> OTHER INFORMATION: Artificial sequence

<400> SEQUENCE: 39

Asp Gly Gly Tyr Asp Tyr Pro Thr His Ala Met His Tyr
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Artificial sequence

<400> SEQUENCE: 40
```

```
Gln Ala Ser Gln Asn Ile Gly Ser Ser Leu Ala
1               5                   10

<210> SEQ ID NO 41
<211> LENGTH: 7
<212> TYPE: PRT
<213> ORGANISM: Artificial Sequence
<220> FEATURE:
<223> OTHER INFORMATION: Artificial sequence

<400> SEQUENCE: 41

Gly Ala Ser Lys Thr His Ser
1               5

<210> SEQ ID NO 42
<211> LENGTH: 12
<212> TYPE: PRT
<213> ORGANISM: Artificial Sequence
<220> FEATURE:
<223> OTHER INFORMATION: Artificial sequence

<400> SEQUENCE: 42

Gln Ser Thr Lys Val Gly Ser Ser Tyr Gly Asn His
1               5                   10

<210> SEQ ID NO 43
<211> LENGTH: 123
<212> TYPE: PRT
<213> ORGANISM: Artificial Sequence
<220> FEATURE:
<223> OTHER INFORMATION: Heavy chain variable region

<400> SEQUENCE: 43

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ser His Ser Ser
            20                  25                  30

Tyr Tyr Val Ala Trp Val Arg Gln Ala Pro Gly Lys Gly Leu Glu Trp
            35                  40                  45

Val Gly Ala Ile Tyr Thr Gly Ser Gly Ala Thr Tyr Lys Ala Ser Trp
        50                  55                  60

Ala Lys Gly Arg Phe Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Ser Asp Gly Gly Tyr Asp Tyr Pro Thr His Ala Met His Tyr
                100                 105                 110

Trp Gly Gln Gly Thr Leu Val Thr Val Ser Ser
        115                 120

<210> SEQ ID NO 44
<211> LENGTH: 110
<212> TYPE: PRT
<213> ORGANISM: Artificial Sequence
<220> FEATURE:
<223> OTHER INFORMATION: Light chain variable region

<400> SEQUENCE: 44

Asp Val Val Met Thr Gln Ser Pro Ser Ser Leu Ser Ala Ser Val Gly
1               5                   10                  15

Asp Arg Val Thr Ile Thr Cys Gln Ala Ser Gln Asn Ile Gly Ser Ser
            20                  25                  30
```

-continued

```
Leu Ala Trp Tyr Gln Gln Lys Pro Gly Gln Ala Pro Arg Leu Leu Ile
        35                  40                  45

Tyr Gly Ala Ser Lys Thr His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Ser Thr Lys Val Gly Ser Ser
                85                  90                  95

Tyr Gly Asn His Phe Gly Gly Gly Thr Lys Val Glu Ile Lys
            100                 105                 110

<210> SEQ ID NO 45
<211> LENGTH: 451
<212> TYPE: PRT
<213> ORGANISM: Artificial Sequence
<220> FEATURE:
<223> OTHER INFORMATION: Heavy chain sequence

<400> SEQUENCE: 45

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Val His Ser Ser
            20                  25                  30

Tyr Tyr Met Ala Trp Val Arg Gln Ala Pro Gly Lys Gly Leu Glu Trp
            35                  40                  45

Val Gly Ala Ile Phe Thr Gly Ser Gly Ala Glu Tyr Lys Ala Glu Trp
    50                  55                  60

Ala Lys Gly Arg Val Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Ser Asp Ala Gly Tyr Asp Tyr Pro Thr His Ala Met His Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Arg Arg Gly Pro Lys Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285
```

-continued

```
Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
                355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Leu His Glu Ala Leu His Ala His Tyr Thr Arg Lys Glu Leu Ser
    435                 440                 445

Leu Ser Pro
    450

<210> SEQ ID NO 46
<211> LENGTH: 217
<212> TYPE: PRT
<213> ORGANISM: Artificial Sequence
<220> FEATURE:
<223> OTHER INFORMATION: Light chain sequence

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ser
                20                  25                  30

Leu Ala Trp Tyr Gln Gln Lys Pro Gly Lys Ala Pro Lys Leu Leu Ile
            35                  40                  45

Tyr Gly Ala Ser Glu Thr Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Thr Lys Val Gly Ser Ser
                85                  90                  95

Tyr Gly Asn Thr Phe Gly Gly Gly Thr Lys Val Glu Ile Lys Arg Thr
                100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
        130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190
```

-continued

```
Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 47
<211> LENGTH: 120
<212> TYPE: PRT
<213> ORGANISM: Artificial Sequence
<220> FEATURE:
<223> OTHER INFORMATION: VH sequence

<400> SEQUENCE: 47

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Val Ser Ser Ser
        20                  25                  30

Tyr Trp Thr Trp Ile Arg Gln Pro Pro Gly Lys Gly Leu Glu Trp Ile
        35                  40                  45

Gly Tyr Ile Tyr Tyr Ser Gly Ser Ser Asn Tyr Asn Pro Ser Leu Lys
    50                  55                  60

Ser Arg Ala Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Gly Asn Val Asp Thr Thr Met Ile Phe Asp Tyr Trp Gly Gln
            100                 105                 110

Gly Thr Leu Val Thr Val Ser Ser
        115                 120

<210> SEQ ID NO 48
<211> LENGTH: 107
<212> TYPE: PRT
<213> ORGANISM: Artificial Sequence
<220> FEATURE:
<223> OTHER INFORMATION: VL sequence

<400> SEQUENCE: 48

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
        20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ala Gly
    50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Phe Asn Tyr Pro Trp
                85                  90                  95

Thr Phe Gly Gln Gly Thr Lys Val Glu Ile Lys
            100                 105

<210> SEQ ID NO 49
<211> LENGTH: 447
<212> TYPE: PRT
<213> ORGANISM: Artificial Sequence
<220> FEATURE:
<223> OTHER INFORMATION: Heavy chain sequence
```

```
<400> SEQUENCE: 49

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Val Ser Ser Ser
            20                  25                  30

Tyr Trp Thr Trp Ile Arg Gln Pro Pro Gly Lys Gly Leu Glu Trp Ile
        35                  40                  45

Gly Tyr Ile Tyr Tyr Ser Gly Ser Ser Asn Tyr Asn Pro Ser Leu Lys
    50                  55                  60

Ser Arg Ala Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Gly Asn Val Asp Thr Thr Met Ile Phe Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415
```

-continued

```
Trp Gln Glu Gly Asn Val Phe Ser Cys Ser Val Met His Glu Ala Leu
            420                 425             430

His Asn His Tyr Thr Gln Lys Ser Leu Ser Leu Ser Leu Gly Lys
        435                 440                 445

<210> SEQ ID NO 50
<211> LENGTH: 214
<212> TYPE: PRT
<213> ORGANISM: Artificial Sequence
<220> FEATURE:
<223> OTHER INFORMATION: Light chain sequence

<400> SEQUENCE: 50

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ala Gly
    50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Phe Asn Tyr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```